US008859507B2

(12) United States Patent
Lee

(10) Patent No.: US 8,859,507 B2
(45) Date of Patent: Oct. 14, 2014

(54) PROTEIN COMPLEX FOR INTRACELLULAR DELIVERY AND USES THEREOF

(75) Inventor: Jae-il Lee, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 13/587,719

(22) Filed: Aug. 16, 2012

(65) Prior Publication Data

US 2013/0123199 A1 May 16, 2013

(30) Foreign Application Priority Data

Aug. 16, 2011 (KR) ........................ 10-2011-0081160

(51) Int. Cl.

*A61K 47/42* (2006.01)
*C07K 14/47* (2006.01)
*A61K 45/06* (2006.01)
*A61K 38/00* (2006.01)

(52) U.S. Cl.

CPC ................. *A61K 47/42* (2013.01); *A61K 38/00* (2013.01); *C07K 14/47* (2013.01); *A61K 45/06* (2013.01)

USPC .......................... 514/21.2; 435/375; 435/69.7

(58) Field of Classification Search

None

See application file for complete search history.

(56) References Cited

U.S. PATENT DOCUMENTS 6,267,964 B1 * 7/2001 Nygren et al. ........... 424/197.11
2011/0135596 A1 * 6/2011 Lee et al. ..................... 424/85.2

FOREIGN PATENT DOCUMENTS

EP 1 362 917 A2 11/2003
JP 2000-007576 1/2000
KR 100887266 B1 2/2009
KR 1020090103957 A 10/2009
KR 1020110062997 A 6/2011

OTHER PUBLICATIONS

Bailon et al (Expert Opin Drug Deliv. Jan. 2009;6(1):1-16).*

English translation of KR 10-2011-0062997 (publication of Korean application 10-2009-0119912).*

Bowie et al. (Science, 1990, 247:1306-1310).*

Burgess et al. (J. Cell Biol. 111:2129-2138, 1990).*

Lazar et al. (Mol. Cell. Biol., 8:1247-1252, 1988).*

Carter et al., “C-Terminal Modifications Regulate MDM2 Dissociation,” Nature Cell Biology, Apr. 2007, 428-435,-9-4,Nature Publishing Group.

Lin et al., “Inhibition of Nuclear Translocation of Transcription Factor NF-κB by a Synthetic Peptide Containing a Cell Membranepermeable Motif and Nuclear Localization Sequence,” The Journal of Biological Chemistry, Jun. 1995, 270, 14255-14258, doi: 10.1074/jbc.270.24.14255, The American Society for Biochemistry and Molecular Biology, Inc.

* cited by examiner

*Primary Examiner* — Brian J Gangle

*Assistant Examiner* — Andrea McCollum

(74) *Attorney, Agent, or Firm* — Leydig, Voit & Mayer, Ltd.

(57) ABSTRACT

A protein complex comprising an in vitro stabilization protein, a membrane translocation sequence domain, a biologically active molecule, and an in vivo stabilization protein, as well as methods for the use and production thereof.

7 Claims, 6 Drawing Sheets

SEQUENCE LISTING

```
<160> NUMBER OF SEQ ID NOS: 103

<210> SEQ ID NO 1
<211> LENGTH: 16
<212> TYPE: PRT
<213> ORGANISM: Artificial Sequence
<220> FEATURE:
<223> OTHER INFORMATION: Synthetic (membrane translocation sequence
      domain)

<400> SEQUENCE: 1

Ala Ala Val Ala Leu Leu Pro Ala Val Leu Leu Ala Leu Leu Ala Pro
1               5                   10                  15


<210> SEQ ID NO 2
<211> LENGTH: 12
<212> TYPE: PRT
<213> ORGANISM: Artificial Sequence
<220> FEATURE:
<223> OTHER INFORMATION: Synthetic (membrane translocation sequence
      domain)

<400> SEQUENCE: 2

Ala Ala Val Leu Leu Pro Val Leu Leu Ala Ala Pro
1               5                   10


<210> SEQ ID NO 3
<211> LENGTH: 11
<212> TYPE: PRT
<213> ORGANISM: Artificial Sequence
<220> FEATURE:
<223> OTHER INFORMATION: Synthetic (membrane translocation sequence
      domain)

<400> SEQUENCE: 3

Leu Leu His Leu Ser Leu Leu Ala Leu Ala Pro
1               5                   10


<210> SEQ ID NO 4
<211> LENGTH: 15
<212> TYPE: PRT
<213> ORGANISM: Artificial Sequence
<220> FEATURE:
<223> OTHER INFORMATION: Synthetic (membrane translocation sequence
      domain)

<400> SEQUENCE: 4

Leu Ala Val Ala Leu Leu Ala Ala Phe Leu Ile Ser Ala Ala Pro
1               5                   10                  15


<210> SEQ ID NO 5
<211> LENGTH: 13
<212> TYPE: PRT
<213> ORGANISM: Artificial Sequence
<220> FEATURE:
<223> OTHER INFORMATION: Synthetic (membrane translocation sequence
```

domain)

<400> SEQUENCE: 5

Ala Leu Leu Ala Ala Leu Leu Ala Ala Pro Gly Ala Ala
1 5 10

<210> SEQ ID NO 6
<211> LENGTH: 8
<212> TYPE: PRT
<213> ORGANISM: Artificial Sequence
<220> FEATURE:
<223> OTHER INFORMATION: Synthetic (membrane translocation sequence domain)

<400> SEQUENCE: 6

Leu Ile Ile Leu Leu Pro Val Val
1 5

<210> SEQ ID NO 7
<211> LENGTH: 16
<212> TYPE: PRT
<213> ORGANISM: Artificial Sequence
<220> FEATURE:
<223> OTHER INFORMATION: Synthetic (membrane translocation sequence domain)

<400> SEQUENCE: 7

Ala Ile Gly Leu Leu Trp Leu Leu Pro Leu Leu Leu Ser Thr Ala Ala
1 5 10 15

<210> SEQ ID NO 8
<211> LENGTH: 9
<212> TYPE: PRT
<213> ORGANISM: Artificial Sequence
<220> FEATURE:
<223> OTHER INFORMATION: Synthetic (membrane translocation sequence domain)

<400> SEQUENCE: 8

Leu Leu Leu Pro Ile Leu Ser Ser Ala
1 5

<210> SEQ ID NO 9
<211> LENGTH: 11
<212> TYPE: PRT
<213> ORGANISM: Artificial Sequence
<220> FEATURE:
<223> OTHER INFORMATION: Synthetic (membrane translocation sequence domain)

<400> SEQUENCE: 9

Leu Leu Leu Leu Leu Leu Leu Pro Leu Leu Gly
1 5 10

<210> SEQ ID NO 10
<211> LENGTH: 13
<212> TYPE: PRT
<213> ORGANISM: Artificial Sequence
<220> FEATURE:
<223> OTHER INFORMATION: Synthetic (membrane translocation sequence domain)

<400> SEQUENCE: 10

Leu Gly Ala Ala Leu Leu Leu Leu Pro Leu Leu Ala Ala
1 5 10

<210> SEQ ID NO 11

<211> LENGTH: 11
<212> TYPE: PRT
<213> ORGANISM: Artificial Sequence
<220> FEATURE:
<223> OTHER INFORMATION: Synthetic (membrane translocation sequence domain)

<400> SEQUENCE: 11

Leu Leu Ser Val Leu Leu Leu Pro Leu Leu Gly
1 5 10

<210> SEQ ID NO 12
<211> LENGTH: 11
<212> TYPE: PRT
<213> ORGANISM: Artificial Sequence
<220> FEATURE:
<223> OTHER INFORMATION: Synthetic (membrane translocation sequence domain)

<400> SEQUENCE: 12

Leu Leu Leu Leu Pro Leu Leu Leu Leu Pro Ala
1 5 10

<210> SEQ ID NO 13
<211> LENGTH: 16
<212> TYPE: PRT
<213> ORGANISM: Artificial Sequence
<220> FEATURE:
<223> OTHER INFORMATION: Synthetic (membrane translocation sequence domain)

<400> SEQUENCE: 13

Leu Leu Leu Ala Gly Leu Ala Ser Leu Leu Leu Pro Gly Ser Ala Ala
1 5 10 15

<210> SEQ ID NO 14
<211> LENGTH: 20
<212> TYPE: PRT
<213> ORGANISM: Artificial Sequence
<220> FEATURE:
<223> OTHER INFORMATION: Synthetic (membrane translocation sequence domain)

<400> SEQUENCE: 14

Gly Ala Ala Ala Ala Pro Leu Leu Val Ala Val Ala Ala Leu Leu Leu
1 5 10 15

Gly Ala Ala Gly
20

<210> SEQ ID NO 15
<211> LENGTH: 9
<212> TYPE: PRT
<213> ORGANISM: Artificial Sequence
<220> FEATURE:
<223> OTHER INFORMATION: Synthetic (membrane translocation sequence domain)

<400> SEQUENCE: 15

Gly Gly Gln Leu Pro Leu Leu Val Val
1 5

<210> SEQ ID NO 16
<211> LENGTH: 5
<212> TYPE: PRT
<213> ORGANISM: Artificial Sequence
<220> FEATURE:
<223> OTHER INFORMATION: Synthetic (nucleus localization signal domain)

<400> SEQUENCE: 16

```
Lys Lys Lys Arg Lys
1               5
```

<210> SEQ ID NO 17
<211> LENGTH: 7
<212> TYPE: PRT
<213> ORGANISM: Artificial Sequence
<220> FEATURE:
<223> OTHER INFORMATION: Synthetic (nucleus localization signal domain)

<400> SEQUENCE: 17

```
Pro Lys Lys Lys Arg Lys Val
1               5
```

<210> SEQ ID NO 18
<211> LENGTH: 16
<212> TYPE: PRT
<213> ORGANISM: Artificial Sequence
<220> FEATURE:
<223> OTHER INFORMATION: Synthetic (nucleous localization signal domain)

<400> SEQUENCE: 18

```
Lys Arg Pro Ala Ala Thr Lys Lys Ala Gly Gln Ala Lys Lys Lys Lys
1               5                   10                  15
```

<210> SEQ ID NO 19
<211> LENGTH: 76
<212> TYPE: PRT
<213> ORGANISM: Artificial Sequence
<220> FEATURE:
<223> OTHER INFORMATION: Synthetic (Ubiquitin wild type protein (Homo sapiens))

<400> SEQUENCE: 19

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```

<210> SEQ ID NO 20
<211> LENGTH: 479
<212> TYPE: DNA
<213> ORGANISM: Artificial Sequence
<220> FEATURE:
<223> OTHER INFORMATION: Synthetic

<400> SEQUENCE: 20

```
catatgagag gatcgcatca ccatcaccat cacgattacg atatcccaac gaccgaaaac      60

ctgtattttc agggatccgg tggtggtggt atgcagattt tcgtgagaac ccttacgggg     120

aggaccatca ccctcgaagt tgaaccctcg gatacgatag aaaatgtaag ggccagaatc     180

caggataggg aaggaatacc tcctgatcag cagagactga tctttgctgg caggcagctg     240

gaagatggac gtactttgtc tgactacaat attcaaaggg agtctactct tcatcttgtg     300

ttgagacttc gtggtgctgg tggtgccgcg gtagcgctgc tcccggcggt cctgctggcc     360
```

ttgctggcgc ccggtggtaa aaagaagaga aagggtggtg gtggaggtag tgatatctgt 420
ctgcctcgtt ggggttgtct gtgggaagat taactcgagc accaccacca ccaccactg 479

<210> SEQ ID NO 21
<211> LENGTH: 524
<212> TYPE: DNA
<213> ORGANISM: Artificial Sequence
<220> FEATURE:
<223> OTHER INFORMATION: Synthetic

<400> SEQUENCE: 21
catatgagag gatcgcatca ccatcaccat cacgattacg atatcccaac gaccgaaaac 60
ctgtattttc agggatccgg tggtggtggt atgcagattt tcgtgagaac ccttacgggg 120
aggaccatca ccctcgaagt tgaaccctcg gatacgatag aaaatgtaag ggccagaatc 180
caggataggg aaggaatacc tcctgatcag cagagactga tctttgctgg caggcagctg 240
gaagatggac gtactttgtc tgactacaat attcaaaggg agtctactct tcatcttgtg 300
ttgagacttc gtggtgctgg tggtgccgcg gtagcgctgc tcccggcggt cctgctggcc 360
ttgctggcgc ccggtggtga aacattttca gacctatgga aactacttcc tgaaaacggt 420
ggtaaaaaga agagaaaggg tggtggtgga ggtagtgata tctgtctgcc tcgttggggt 480
tgtctgtggg aagattaact cgagcaccac caccaccacc actg 524

<210> SEQ ID NO 22
<211> LENGTH: 470
<212> TYPE: DNA
<213> ORGANISM: Artificial Sequence
<220> FEATURE:
<223> OTHER INFORMATION: Synthetic

<400> SEQUENCE: 22
catatgagag gatcgcatca ccatcaccat cacgattacg atatcccaac gaccgaaaac 60
ctgtattttc agggatccgg tggtggtggt atgcagattt tcgtgagaac ccttacgggg 120
aggaccatca ccctcgaagt tgaaccctcg gatacgatag aaaatgtaag ggccagaatc 180
caggataggg aaggaatacc tcctgatcag cagagactga tctttgctgg caggcagctg 240
gaagatggac gtactttgtc tgactacaat attcaaaggg agtctactct tcatcttgtg 300
ttgagacttc gtggtgctgg tggtgaaaca ttttcagacc tatggaaact acttcctgaa 360
aacggtggta aaaagaagag aaagggtggt ggtggaggta gtgatatctg tctgcctcgt 420
tggggttgtc tgtgggaaga ttaactcgag caccaccacc accaccactg 470

<210> SEQ ID NO 23
<211> LENGTH: 989
<212> TYPE: DNA
<213> ORGANISM: Artificial Sequence
<220> FEATURE:
<223> OTHER INFORMATION: Synthetic

<400> SEQUENCE: 23
catatgagag gatcgcatca ccatcaccat cacgattacg atatcccaac gaccgaaaac 60
ctgtattttc agggatccgg tggtggtggt atgcagattt tcgtgagaac ccttacgggg 120
aggaccatca ccctcgaagt tgaaccctcg gatacgatag aaaatgtaag ggccagaatc 180
caggataggg aaggaatacc tcctgatcag cagagactga tctttgctgg caggcagctg 240
gaagatggac gtactttgtc tgactacaat attcaaaggg agtctactct tcatcttgtg 300
ttgagacttc gtggtgctgg tggtgccgcg gtagcgctgc tcccggcggt cctgctggcc 360

```
ttgctggcgc ccggtggtat ggccgagcct tgggggaacg agttggcgtc cgcagctgcc    420

aggggggacc tagagcaact tactagtttg ttgcaaaata atgtaaacgt caatgcacaa    480

aatggatttg gaaggactgc gctgcaggtt atgaaacttg gaaatcccga gattgccagg    540

agactgctac ttagaggtgc taatcccgat ttgaaagacc gaactggtaa tgctgtcatt    600

catgatgcgg ccagagcagg tttcctggac actttacaga ctttgctgga gtttcaagct    660

gatgttaaca tcgaggataa tgaagggaac ctgcccttgc acttggctgc caaagaaggc    720

cacctccggg tggtggagtt cctggtgaag cacacggcca gcaatgtggg gcatcggaac    780

cataaggggg acaccgcctg tgatttggcc aggctctatg ggaggaatga ggttgttagc    840

ctgatgcagg caaacggggc tgggggagcc acaaatcttc aaggtggtaa aaagaagaga    900

aagggtggtg gtggaggtag tgatatctgt ctgcctcgtt ggggttgtct gtgggaagat    960

taactcgagc accaccacca ccaccactg                                      989
```

<210> SEQ ID NO 24
<211> LENGTH: 935
<212> TYPE: DNA
<213> ORGANISM: Artificial Sequence
<220> FEATURE:
<223> OTHER INFORMATION: Synthetic

<400> SEQUENCE: 24

```
catatgagag gatcgcatca ccatcaccat cacgattacg atatcccaac gaccgaaaac     60

ctgtattttc agggatccgg tggtggtggt atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctgg tggtatggcc gagccttggg ggaacgagtt ggcgtccgca    360

gctgccaggg gggacctaga gcaacttact agtttgttgc aaaataatgt aaacgtcaat    420

gcacaaaatg gatttggaag gactgcgctg caggttatga aacttggaaa tcccgagatt    480

gccaggagac tgctacttag aggtgctaat cccgatttga aagaccgaac tggtaatgct    540

gtcattcatg atgcggccag agcaggtttc ctggacactt tacagacttt gctggagttt    600

caagctgatg ttaacatcga ggataatgaa gggaacctgc ccttgcactt ggctgccaaa    660

gaaggccacc tccgggtggt ggagttcctg gtgaagcaca cggccagcaa tgtggggcat    720

cggaaccata agggggacac cgcctgtgat ttggccaggc tctatgggag gaatgaggtt    780

gttagcctga tgcaggcaaa cggggctggg ggagccacaa atcttcaagg tggtaaaaag    840

aagagaaagg gtggtggtgg aggtagtgat atctgtctgc ctcgttgggg ttgtctgtgg    900

gaagattaac tcgagcacca ccaccaccac cactg                               935
```

<210> SEQ ID NO 25
<211> LENGTH: 945
<212> TYPE: DNA
<213> ORGANISM: Artificial Sequence
<220> FEATURE:
<223> OTHER INFORMATION: Synthertic

<400> SEQUENCE: 25

```
catatgagag gatcgcatca ccatcaccat cacgattacg atatcccaac gaccgaaaac     60

ctgtattttc agggatccgg tagtggaagc atgcagattt tcgtgagaac ccttacgggg    120
```

-continued aggaccatca ccctcgaagt tgaaccctcg gatacgatag aaaatgtaag ggccagaatc 180
caggataggg aaggaatacc tcctgatcag cagagactga tctttgctgg caggcagctg 240
gaagatggac gtactttgtc tgactacaat attcaaaggg agtctactct tcatcttgtg 300
ttgagacttc gtggtgctga attcgccgcg gtagcgctgc tcccggcggt cctgctggcc 360
ttgctggcgc ccgaaacatt ttcagaccta tggaaactac ttcctgaaaa caagcttatg 420
gccgagcctt gggggaacga gttggcgtcc gcagctgcca ggggggacct agagcaactt 480
actagtttgt tgcaaaataa tgtaaacgtc aatgcacaaa atggatttgg aaggactgcg 540
ctgcaggtta tgaaacttgg aaatcccgag attgccagga gactgctact tagaggtgct 600
aatcccgatt tgaaagaccg aactggtaat gctgtcattc atgatgcggc cagagcaggt 660
ttcctggaca ctttacagac tttgctggag tttcaagctg atgttaacat cgaggataat 720
gaagggaacc tgcccttgca cttggctgcc aaagaaggcc acctccgggt ggtggagttc 780
ctggtgaagc acacggccag caatgtgggg catcggaacc ataaggggga caccgcctgt 840
gatttggcca ggctctatgg gaggaatgag gttgttagcc tgatgcaggc aaacggggct 900
gggggagcca caaatcttca aaaaaagaag agaaagtaac tcgag 945

<210> SEQ ID NO 26
<211> LENGTH: 996
<212> TYPE: DNA
<213> ORGANISM: Artificial Sequence
<220> FEATURE:
<223> OTHER INFORMATION: Synthetic

<400> SEQUENCE: 26
catatgagag gatcgcatca ccatcaccat cacgattacg atatcccaac gaccgaaaac 60
ctgtattttc agggatccgg tagtggaagc atgcagattt tcgtgagaac ccttacgggg 120
aggaccatca ccctcgaagt tgaaccctcg gatacgatag aaaatgtaag ggccagaatc 180
caggataggg aaggaatacc tcctgatcag cagagactga tctttgctgg caggcagctg 240
gaagatggac gtactttgtc tgactacaat attcaaaggg agtctactct tcatcttgtg 300
ttgagacttc gtggtgctga attcgccgcg gtagcgctgc tcccggcggt cctgctggcc 360
ttgctggcgc ccgaaacatt ttcagaccta tggaaactac ttcctgaaaa caagcttatg 420
gccgagcctt gggggaacga gttggcgtcc gcagctgcca ggggggacct agagcaactt 480
actagtttgt tgcaaaataa tgtaaacgtc aatgcacaaa atggatttgg aaggactgcg 540
ctgcaggtta tgaaacttgg aaatcccgag attgccagga gactgctact tagaggtgct 600
aatcccgatt tgaaagaccg aactggtaat gctgtcattc atgatgcggc cagagcaggt 660
ttcctggaca ctttacagac tttgctggag tttcaagctg atgttaacat cgaggataat 720
gaagggaacc tgcccttgca cttggctgcc aaagaaggcc acctccgggt ggtggagttc 780
ctggtgaagc acacggccag caatgtgggg catcggaacc ataaggggga caccgcctgt 840
gatttggcca ggctctatgg gaggaatgag gttgttagcc tgatgcaggc aaacggggct 900
gggggagcca caaatcttca aaaaaagaag agaaagggtg gaggtagtga tatctgtctg 960
cctcgttggg gttgtctgtg ggaagattaa ctcgag 996

<210> SEQ ID NO 27
<211> LENGTH: 996
<212> TYPE: DNA
<213> ORGANISM: Artificial Sequence
<220> FEATURE:
<223> OTHER INFORMATION: Synthetic

<400> SEQUENCE: 27

```
catatgagag gatcgcatca ccatcaccat cacgattacg atatcccaac gaccgaaaac     60
ctgtattttc agggatccgg tagtggaagc atgcagattt tcgtgagaac ccttacgggg    120
aggaccatca ccctcgaagt tgaaccctcg gatacgatag aaaatgtaag ggccagaatc    180
caggataggg aaggaatacc tcctgatcag cagagactga tctttgctgg caggcagctg    240
gaagatggac gtactttgtc tgactacaat attcaaaggg agtctactct tcatcttgtg    300
ttgagacttc gtggtggtga attcgccgcg gtagcgctgc tcccggcggt cctgctggcc    360
ttgctggcgc ccgaaacatt ttcagaccta tggaaactac ttcctgaaaa caagcttatg    420
gccgagcctt gggggaacga gttggcgtcc gcagctgcca ggggggacct agagcaactt    480
actagtttgt tgcaaaataa tgtaaacgtc aatgcacaaa atggatttgg aaggactgcg    540
ctgcaggtta tgaaacttgg aaatcccgag attgccagga gactgctact tagaggtgct    600
aatcccgatt tgaaagaccg aactggtaat gctgtcattc atgatgcggc cagagcaggt    660
ttcctggaca ctttacagac tttgctggag tttcaagctg atgttaacat cgaggataat    720
gaagggaacc tgcccttgca cttggctgcc aaagaaggcc acctccgggt ggtggagttc    780
ctggtgaagc acacggccag caatgtgggg catcggaacc ataaggggga caccgcctgt    840
gatttggcca ggctctatgg gaggaatgag gttgttagcc tgatgcaggc aaacggggct    900
gggggagcca caaatcttca aaaaaagaag agaaagggtg gaggtagtga tatctgtctg    960
cctcgttggg gttgtctgtg ggaagattaa ctcgag                              996
```

<210> SEQ ID NO 28
<211> LENGTH: 897
<212> TYPE: DNA
<213> ORGANISM: Artificial Sequence
<220> FEATURE:
<223> OTHER INFORMATION: Synthetic

<400> SEQUENCE: 28

```
catatgagag gatcgcatca ccatcaccat cacgattacg atatcccaac gaccgaaaac     60
ctgtattttc agggatccgg tagtggaagc atgcagattt tcgtgagaac ccttacgggg    120
aggaccatca ccctcgaagt tgaaccctcg gatacgatag aaaatgtaag ggccagaatc    180
caggataggg aaggaatacc tcctgatcag cagagactga tctttgctgg caggcagctg    240
gaagatggac gtactttgtc tgactacaat attcaaaggg agtctactct tcatcttgtg    300
ttgagacttc gtggtgctga attcgaaaca ttttcagacc tatggaaact acttcctgaa    360
aacaagctta tggccgagcc ttgggggaac gagttggcgt ccgcagctgc caggggggac    420
ctagagcaac ttactagttt gttgcaaaat aatgtaaacg tcaatgcaca aaatggattt    480
ggaaggactg cgctgcaggt tatgaaactt ggaaatcccg agattgccag gagactgcta    540
cttagaggtg ctaatcccga tttgaaagac cgaactggta atgctgtcat tcatgatgcg    600
gccagagcag gtttcctgga cactttacag actttgctgg agtttcaagc tgatgttaac    660
atcgaggata atgaagggaa cctgcccttg cacttggctg ccaaagaagg ccacctccgg    720
gtggtggagt tcctggtgaa gcacacggcc agcaatgtgg ggcatcggaa ccataagggg    780
gacaccgcct gtgatttggc caggctctat gggaggaatg aggttgttag cctgatgcag    840
gcaaacgggg ctgggggagc cacaaatctt caaaaaaaga agagaaagta actcgag       897
```

<210> SEQ ID NO 29

```
<211> LENGTH: 948
<212> TYPE: DNA
<213> ORGANISM: Artificial Sequence
<220> FEATURE:
<223> OTHER INFORMATION: Synthetic

<400> SEQUENCE: 29

catatgagag gatcgcatca ccatcaccat cacgattacg atatcccaac gaccgaaaac     60

ctgtattttc agggatccgg tagtggaagc atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctga attcgaaaca ttttcagacc tatggaaact acttcctgaa    360

aacaagctta tggccgagcc ttgggggaac gagttggcgt ccgcagctgc caggggggac    420

ctagagcaac ttactagttt gttgcaaaat aatgtaaacg tcaatgcaca aaatggattt    480

ggaaggactg cgctgcaggt tatgaaactt ggaaatcccg agattgccag gagactgcta    540

cttagaggtg ctaatcccga tttgaaagac cgaactggta atgctgtcat tcatgatgcg    600

gccagagcag gtttcctgga cactttacag actttgctgg agtttcaagc tgatgttaac    660

atcgaggata atgaagggaa cctgcccttg cacttggctg ccaaagaagg ccacctccgg    720

gtggtggagt tcctggtgaa gcacacggcc agcaatgtgg ggcatcggaa ccataagggg    780

gacaccgcct gtgatttggc caggctctat gggaggaatg aggttgttag cctgatgcag    840

gcaaacgggg ctgggggagc cacaaatctt caaaaaaaga agagaaaggg tggaggtagt    900

gatatctgtc tgcctcgttg ggttgtctg tgggaagatt aactcgag                 948

<210> SEQ ID NO 30
<211> LENGTH: 897
<212> TYPE: DNA
<213> ORGANISM: Artificial Sequence
<220> FEATURE:
<223> OTHER INFORMATION: Synthetic

<400> SEQUENCE: 30

catatgagag gatcgcatca ccatcaccat cacgattacg atatcccaac gaccgaaaac     60

ctgtattttc agggatccgg tagtggaagc atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtggtga attcgaaaca ttttcagacc tatggaaact acttcctgaa    360

aacaagctta tggccgagcc ttgggggaac gagttggcgt ccgcagctgc caggggggac    420

ctagagcaac ttactagttt gttgcaaaat aatgtaaacg tcaatgcaca aaatggattt    480

ggaaggactg cgctgcaggt tatgaaactt ggaaatcccg agattgccag gagactgcta    540

cttagaggtg ctaatcccga tttgaaagac cgaactggta atgctgtcat tcatgatgcg    600

gccagagcag gtttcctgga cactttacag actttgctgg agtttcaagc tgatgttaac    660

atcgaggata atgaagggaa cctgcccttg cacttggctg ccaaagaagg ccacctccgg    720

gtggtggagt tcctggtgaa gcacacggcc agcaatgtgg ggcatcggaa ccataagggg    780

gacaccgcct gtgatttggc caggctctat gggaggaatg aggttgttag cctgatgcag    840

gcaaacgggg ctgggggagc cacaaatctt caaaaaaaga agagaaagta actcgag       897
```

<210> SEQ ID NO 31
<211> LENGTH: 425
<212> TYPE: DNA
<213> ORGANISM: Artificial Sequence
<220> FEATURE:
<223> OTHER INFORMATION: Synthetic

<400> SEQUENCE: 31

```
catatgagag gatcgcatca ccatcaccat cacgattacg atatcccaac gaccgaaaac     60
ctgtattttc agggatccgg tggtggtggt atgcagattt tcgtgagaac ccttacgggg    120
aggaccatca ccctcgaagt tgaaccctcg gatacgatag aaaatgtaag ggccagaatc    180
caggataggg aaggaatacc tcctgatcag cagagactga tctttgctgg caggcagctg    240
gaagatggac gtactttgtc tgactacaat attcaaaggg agtctactct tcatcttgtg    300
ttgagacttc gtggtgctgg tggtaaaaag aagagaaagg gtggtggtgg aggtagtgat    360
atctgtctgc ctcgttgggg ttgtctgtgg gaagattaac tcgagcacca ccaccaccac    420
cactg                                                                425
```

<210> SEQ ID NO 32
<211> LENGTH: 1043
<212> TYPE: DNA
<213> ORGANISM: Artificial Sequence
<220> FEATURE:
<223> OTHER INFORMATION: Synthetic

<400> SEQUENCE: 32

```
catatgagag gatcgcatca ccatcaccat cacgattacg atatcccaac gaccgaaaac     60
ctgtattttc agggatccgg tggtggtggt atgcagattt tcgtgagaac ccttacgggg    120
aggaccatca ccctcgaagt tgaaccctcg gatacgatag aaaatgtaag ggccagaatc    180
caggataggg aaggaatacc tcctgatcag cagagactga tctttgctgg caggcagctg    240
gaagatggac gtactttgtc tgactacaat attcaaaggg agtctactct tcatcttgtg    300
ttgagacttc gtggtgctgg tggtgccgcg gtagcgctgc tcccggcggt cctgctggcc    360
ttgctggcgc ccggtggtga aacattttca gacctatgga aactacttcc tgaaaacggt    420
ggtggtggtg gtatggccga gccttggggg aacgagttgg cgtccgcagc tgccaggggg    480
gacctagagc aacttactag tttgttgcaa aataatgtaa acgtcaatgc acaaaatgga    540
tttggaagga ctgcgctgca ggttatgaaa cttggaaatc ccgagattgc caggagactg    600
ctacttagag gtgctaatcc cgatttgaaa gaccgaactg gtaatgctgt cattcatgat    660
gcggccagag caggtttcct ggacacttta cagactttgc tggagtttca agctgatgtt    720
aacatcgagg ataatgaagg gaacctgccc ttgcacttgg ctgccaaaga aggccacctc    780
cgggtggtgg agttcctggt gaagcacacg gccagcaatg tggggcatcg gaaccataag    840
ggggacaccg cctgtgattt ggccaggctc tatgggagga atgaggttgt tagcctgatg    900
caggcaaacg gggctggggg agccacaaat cttcaaggtg gtaaaaagaa gagaaagggt    960
ggtggtggag gtagtgatat ctgtctgcct cgttggggtt gtctgtggga agattaactc   1020
gagcaccacc accaccacca ctg                                           1043
```

<210> SEQ ID NO 33
<211> LENGTH: 989
<212> TYPE: DNA
<213> ORGANISM: Artificial Sequence
<220> FEATURE:

<223> OTHER INFORMATION: Synthetic

<400> SEQUENCE: 33

```
catatgagag gatcgcatca ccatcaccat cacgattacg atatcccaac gaccgaaaac     60
ctgtattttc agggatccgg tggtggtggt atgcagattt tcgtgagaac ccttacgggg    120
aggaccatca ccctcgaagt tgaaccctcg gatacgatag aaaatgtaag ggccagaatc    180
caggataggg aaggaatacc tcctgatcag cagagactga tctttgctgg caggcagctg    240
gaagatggac gtactttgtc tgactacaat attcaaaggg agtctactct tcatcttgtg    300
ttgagacttc gtggtgctgg tggtgaaaca ttttcagacc tatggaaact acttcctgaa    360
aacggtggtg gtggtggtat ggccgagcct tgggggaacg agttggcgtc cgcagctgcc    420
aggggggacc tagagcaact tactagtttg ttgcaaaata atgtaaacgt caatgcacaa    480
aatggatttg gaaggactgc gctgcaggtt atgaaacttg gaaatcccga gattgccagg    540
agactgctac ttagaggtgc taatcccgat ttgaaagacc gaactggtaa tgctgtcatt    600
catgatgcgg ccagagcagg tttcctggac actttacaga ctttgctgga gtttcaagct    660
gatgttaaca tcgaggataa tgaagggaac ctgcccttgc acttggctgc caaagaaggc    720
cacctccggg tggtggagtt cctggtgaag cacacggcca gcaatgtggg gcatcggaac    780
cataaggggg acaccgcctg tgatttggcc aggctctatg ggaggaatga ggttgttagc    840
ctgatgcagg caaacggggc tgggggagcc acaaatcttc aaggtggtaa aaagaagaga    900
aagggtggtg gtggaggtag tgatatctgt ctgcctcgtt ggggttgtct gtgggaagat    960
taactcgagc accaccacca ccaccactg                                      989
```

<210> SEQ ID NO 34
<211> LENGTH: 1040
<212> TYPE: DNA
<213> ORGANISM: Artificial Sequence
<220> FEATURE:
<223> OTHER INFORMATION: Synthetic

<400> SEQUENCE: 34

```
catatgagag gatcgcatca ccatcaccat cacgattacg atatcccaac gaccgaaaac     60
ctgtattttc agggatccgg tggtggtggt atgcagattt tcgtgagaac ccttacgggg    120
aggaccatca ccctcgaagt tgaaccctcg gatacgatag aaaatgtaag ggccagaatc    180
caggataggg aaggaatacc tcctgatcag cagagactga tctttgctgg caggcagctg    240
gaagatggac gtactttgtc tgactacaat attcaaaggg agtctactct tcatcttgtg    300
ttgagacttc gtggtgctgg tggtgccgcg gtagcgctgc tcccggcggt cctgctggcc    360
ttgctggcgc ccggtggtga aaccttcgaa cactggtggt ctcagctgct gtctggtggt    420
ggtggtggta tggccgagcc ttgggggaac gagttggcgt ccgcagctgc caggggggac    480
ctagagcaac ttactagttt gttgcaaaat aatgtaaacg tcaatgcaca aaatggattt    540
ggaaggactg cgctgcaggt tatgaaactt ggaaatcccg agattgccag gagactgcta    600
cttagaggtg ctaatcccga tttgaaagac cgaactggta atgctgtcat tcatgatgcg    660
gccagagcag gtttcctgga cactttacag actttgctgg agtttcaagc tgatgttaac    720
atcgaggata atgaagggaa cctgcccttg cacttggctg ccaaagaagg ccacctccgg    780
gtggtggagt tcctggtgaa gcacacggcc agcaatgtgg ggcatcggaa ccataagggg    840
gacaccgcct gtgatttggc caggctctat gggaggaatg aggttgttag cctgatgcag    900
gcaaacgggg ctgggggagc cacaaatctt caaggtggta aaaagaagag aaagggtggt    960
```

ggtggaggta gtgatatctg tctgcctcgt tggggttgtc tgtgggaaga ttaactcgag 1020
caccaccacc accaccactg 1040

<210> SEQ ID NO 35
<211> LENGTH: 521
<212> TYPE: DNA
<213> ORGANISM: Artificial Sequence
<220> FEATURE:
<223> OTHER INFORMATION: Synthetic

<400> SEQUENCE: 35
catatgagag gatcgcatca ccatcaccat cacgattacg atatcccaac gaccgaaaac 60
ctgtattttc agggatccgg tggtggtggt atgcagattt tcgtgagaac ccttacgggg 120
aggaccatca ccctcgaagt tgaaccctcg gatacgatag aaaatgtaag ggccagaatc 180
caggataggg aaggaatacc tcctgatcag cagagactga tctttgctgg caggcagctg 240
gaagatggac gtactttgtc tgactacaat attcaaaggg agtctactct tcatcttgtg 300
ttgagacttc gtggtgctgg tggtgccgcg gtagcgctgc tcccggcggt cctgctggcc 360
ttgctggcgc ccggtggtga aaccttcgaa cactggtggt ctcagctgct gtctggtggt 420
aaaaagaaga gaaagggtgg tggtggaggt agtgatatct gtctgcctcg ttggggttgt 480
ctgtgggaag attaactcga gcaccaccac caccaccact g 521

<210> SEQ ID NO 36
<211> LENGTH: 1040
<212> TYPE: DNA
<213> ORGANISM: Artificial Sequence
<220> FEATURE:
<223> OTHER INFORMATION: Synthetic

<400> SEQUENCE: 36
catatgagag gatcgcatca ccatcaccat cacgattacg atatcccaac gaccgaaaac 60
ctgtattttc agggatccgg tggtggtggt atgcagattt tcgtgagaac ccttacgggg 120
aggaccatca ccctcgaagt tgaaccctcg gatacgatag aaaatgtaag ggccagaatc 180
caggataggg aaggaatacc tcctgatcag cagagactga tctttgctgg caggcagctg 240
gaagatggac gtactttgtc tgactacaat attcaaaggg agtctactct tcatcttgtg 300
ttgagacttc gtggtgctgg tggtgccgcg gtagcgctgc tcccggcggt cctgctggcc 360
ttgctggcgc ccggtggtac ctctttcgct gaatactgga acctgctgtc tccgggtggt 420
ggtggtggta tggccgagcc ttgggggaac gagttggcgt ccgcagctgc cagggggggac 480 ctagagcaac ttactagttt gttgcaaaat aatgtaaacg tcaatgcaca aaatggattt 540
ggaaggactg cgctgcaggt tatgaaactt ggaaatcccg agattgccag gagactgcta 600
cttagaggtg ctaatcccga tttgaaagac cgaactggta atgctgtcat tcatgatgcg 660
gccagagcag gtttcctgga cactttacag actttgctgg agtttcaagc tgatgttaac 720
atcgaggata atgaagggaa cctgcccttg cacttggctg ccaaagaagg ccacctccgg 780
gtggtggagt tcctggtgaa gcacacggcc agcaatgtgg ggcatcggaa ccataagggg 840
gacaccgcct gtgatttggc caggctctat gggaggaatg aggttgttag cctgatgcag 900
gcaaacgggg ctgggggagc cacaaatctt caaggtggta aaaagaagag aaagggtggt 960
ggtggaggta gtgatatctg tctgcctcgt tggggttgtc tgtgggaaga ttaactcgag 1020
caccaccacc accaccactg 1040

<210> SEQ ID NO 37
<211> LENGTH: 521
<212> TYPE: DNA
<213> ORGANISM: Artificial Sequence
<220> FEATURE:
<223> OTHER INFORMATION: Synthetic

<400> SEQUENCE: 37

```
catatgagag gatcgcatca ccatcaccat cacgattacg atatcccaac gaccgaaaac     60

ctgtattttc agggatccgg tggtggtggt atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctgg tggtgccgcg gtagcgctgc tcccggcggt cctgctggcc    360

ttgctggcgc ccggtggtac ctctttcgct gaatactgga acctgctgtc tccgggtggt    420

aaaaagaaga gaaagggtgg tggtggaggt agtgatatct gtctgcctcg ttggggttgt    480

ctgtgggaag attaactcga gcaccaccac caccaccact g                        521
```

<210> SEQ ID NO 38
<211> LENGTH: 1040
<212> TYPE: DNA
<213> ORGANISM: Artificial Sequence
<220> FEATURE:
<223> OTHER INFORMATION: Synthetic

<400> SEQUENCE: 38

```
catatgagag gatcgcatca ccatcaccat cacgattacg atatcccaac gaccgaaaac     60

ctgtattttc agggatccgg tggtggtggt atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctgg tggtgccgcg gtagcgctgc tcccggcggt cctgctggcc    360

ttgctggcgc ccggtggtga aaccttcgaa cactggtgga acctgctgtc tccgggtggt    420

ggtggtggta tggccgagcc ttgggggaac gagttggcgt ccgcagctgc caggggggac    480

ctagagcaac ttactagttt gttgcaaaat aatgtaaacg tcaatgcaca aaatggattt    540

ggaaggactg cgctgcaggt tatgaaactt ggaaatcccg agattgccag gagactgcta    600

cttagaggtg ctaatcccga tttgaaagac cgaactggta atgctgtcat tcatgatgcg    660

gccagagcag gtttcctgga cactttacag actttgctgg agtttcaagc tgatgttaac    720

atcgaggata atgaagggaa cctgcccttg cacttggctg ccaaagaagg ccacctccgg    780

gtggtggagt tcctggtgaa gcacacggcc agcaatgtgg ggcatcggaa ccataagggg    840

gacaccgcct gtgatttggc caggctctat gggaggaatg aggttgttag cctgatgcag    900

gcaaacgggg ctgggggagc cacaaatctt caaggtggta aaaagaagag aaagggtggt    960

ggtggaggta gtgatatctg tctgcctcgt tggggttgtc tgtgggaaga ttaactcgag   1020

caccaccacc accaccactg                                               1040
```

<210> SEQ ID NO 39
<211> LENGTH: 521
<212> TYPE: DNA
<213> ORGANISM: Artificial Sequence
<220> FEATURE:
<223> OTHER INFORMATION: Synthetic

<400> SEQUENCE: 39

```
catatgagag gatcgcatca ccatcaccat cacgattacg atatcccaac gaccgaaaac     60

ctgtattttc agggatccgg tggtggtggt atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctgg tggtgccgcg gtagcgctgc tcccggcggt cctgctggcc    360

ttgctggcgc ccggtggtga aaccttcgaa cactggtgga acctgctgtc tccgggtggt    420

aaaaagaaga gaaagggtgg tggtggaggt agtgatatct gtctgcctcg ttggggttgt    480

ctgtgggaag attaactcga gcaccaccac caccaccact g                        521
```

<210> SEQ ID NO 40
<211> LENGTH: 1634
<212> TYPE: DNA
<213> ORGANISM: Artificial Sequence
<220> FEATURE:
<223> OTHER INFORMATION: Synthetic

<400> SEQUENCE: 40

```
catatgagag gatcgcatca ccatcaccat cacgattacg atatcccaac gaccgaaaac     60

ctgtattttc agggatccgg tggtggtggt atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctgg tggtggtggt ggtatggaag acccgcaggg tgacgctgct    360

cagaaaaccg acacctctca ccacgaccag gaccacccga ccttcaacaa aatcaccccg    420

aacctggctg aattcgcttt ctctctgtac cgtcagctgg ctcaccagtc taactctacc    480

aacatcttct tctctccggt ttctatcgct accgctttcg ctatgctgtc tctgggtacc    540

aaagctgaca cccacgacga aatcctggaa ggtctgaact tcaacctgac cgaaatcccg    600

gaagctcaga tccacgaagg tttccaggaa ctgctgcgta ccctgaacca gccggactct    660

cagctgcagc tgaccaccgg taacttcctg ttcctgtctg aaggtctgaa actggttgac    720

aaattcctgg aagacgttaa aaaactgtac cactctgaag ctttcaccgt taacttcggt    780

gacaccgaag aagctaaaaa acagatcaac gactacgttg aaaaaggtac ccagggtaaa    840

atcgttgacc tggttaaaga actggaccgt gacaccgttt tcgctctggt taactacatc    900

ttcttcaaag gtaaatggga acgtccgttc gaagttaaag acaccgaaga agaagacttc    960

cacgttgacc aggttaccac cgttaaagtt ccgatgatga aacgtctggg tatgttcaac   1020

atccagcact gcaaaaaact gtcttcttgg gttctgctga tgaaatacct gggtaacgct   1080

accgctatct tcttcctgcc ggacgaaggt aaactgcagc acctggaaaa cgaactgacc   1140

cacgacatca tcaccaaatt cctggaaaac gaagaccgtc gttctgcttc tctgcacctg   1200

ccgaaactgt ctatcaccgg tacctacgac ctgaaatctg ttctgggtca gctgggtatc   1260

accaaagttt tctctaacgg tgctgacctg tctggtgtta ccgaagaagc tccgctgaaa   1320

ctgtctaaag ctgttcacaa agctgttctg accatcgacg aaaaaggtac cgaagctgct   1380
```

ggtgctatgt tcctggaagc tatcccgatg tctatcccgc cggaagttaa attcaacaaa 1440
ccgttcgttt tcctgatgat cgaacagaac accaaatctc cgctgttcat gggtaaagtt 1500
gttaacccga cccagaaaaa agacgaactg ggtggtgctg ctgttgctct gctgccggct 1560
gttctgctgg ctctgctggc tccgggtggt aaaaagaaga gaaagtaact cgagcaccac 1620
caccaccacc actg 1634

<210> SEQ ID NO 41
<211> LENGTH: 1580
<212> TYPE: DNA
<213> ORGANISM: Artificial Sequence
<220> FEATURE:
<223> OTHER INFORMATION: Synthetic

<400> SEQUENCE: 41
catatgagag gatcgcatca ccatcaccat cacgattacg atatcccaac gaccgaaaac 60
ctgtattttc agggatccgg tggtggtggt atgcagattt tcgtgagaac ccttacgggg 120
aggaccatca ccctcgaagt tgaaccctcg gatacgatag aaaatgtaag ggccagaatc 180
caggataggg aaggaatacc tcctgatcag cagagactga tctttgctgg caggcagctg 240
gaagatggac gtactttgtc tgactacaat attcaaaggg agtctactct tcatcttgtg 300
ttgagacttc gtggtgctgg tggtggtggt ggtatggaag acccgcaggg tgacgctgct 360
cagaaaaccg acacctctca ccacgaccag gaccacccga ccttcaacaa aatcaccccg 420
aacctggctg aattcgcttt ctctctgtac cgtcagctgg ctcaccagtc taactctacc 480
aacatcttct tctctccggt ttctatcgct accgctttcg ctatgctgtc tctgggtacc 540
aaagctgaca cccacgacga aatcctggaa ggtctgaact tcaacctgac cgaaatcccg 600
gaagctcaga tccacgaagg tttccaggaa ctgctgcgta ccctgaacca gccggactct 660
cagctgcagc tgaccaccgg taacttcctg ttcctgtctg aaggtctgaa actggttgac 720
aaattcctgg aagacgttaa aaaactgtac cactctgaag ctttcaccgt taacttcggt 780
gacaccgaag aagctaaaaa acagatcaac gactacgttg aaaaaggtac ccagggtaaa 840
atcgttgacc tggttaaaga actggaccgt gacaccgttt tcgctctggt taactacatc 900
ttcttcaaag gtaaatggga acgtccgttc gaagttaaag acaccgaaga agaagacttc 960
cacgttgacc aggttaccac cgttaaagtt ccgatgatga aacgtctggg tatgttcaac 1020
atccagcact gcaaaaaact gtcttcttgg gttctgctga tgaaatacct gggtaacgct 1080
accgctatct tcttcctgcc ggacgaaggt aaactgcagc acctggaaaa cgaactgacc 1140
cacgacatca tcaccaaatt cctggaaaac gaagaccgtc gttctgcttc tctgcacctg 1200
ccgaaactgt ctatcaccgg tacctacgac ctgaaatctg ttctgggtca gctgggtatc 1260
accaaagttt tctctaacgg tgctgacctg tctggtgtta ccgaagaagc tccgctgaaa 1320
ctgtctaaag ctgttcacaa agctgttctg accatcgacg aaaaaggtac cgaagctgct 1380
ggtgctatgt tcctggaagc tatcccgatg tctatcccgc cggaagttaa attcaacaaa 1440
ccgttcgttt tcctgatgat cgaacagaac accaaatctc cgctgttcat gggtaaagtt 1500
gttaacccga cccagaaaaa agacgaactg ggtggtaaaa agaagagaaa gtaactcgag 1560
caccaccacc accaccactg 1580

<210> SEQ ID NO 42
<211> LENGTH: 1679
<212> TYPE: DNA
<213> ORGANISM: Artificial Sequence
<220> FEATURE:
<223> OTHER INFORMATION: Synthetic

<400> SEQUENCE: 42
catatgagag gatcgcatca ccatcaccat cacgattacg atatcccaac gaccgaaaac 60
ctgtattttc agggatccgg tggtggtggt atgcagattt tcgtgagaac ccttacgggg 120
aggaccatca ccctcgaagt tgaaccctcg gatacgatag aaaatgtaag ggccagaatc 180
caggataggg aaggaatacc tcctgatcag cagagactga tctttgctgg caggcagctg 240
gaagatggac gtactttgtc tgactacaat attcaaaggg agtctactct tcatcttgtg 300
ttgagacttc gtggtgctgg tggtgaaaca ttttcagacc tatggaaact acttcctgaa 360
aacggtggtg gtggtggtat ggaagacccg cagggtgacg ctgctcagaa aaccgacacc 420
tctcaccacg accaggacca cccgaccttc aacaaaatca ccccgaacct ggctgaattc 480
gctttctctc tgtaccgtca gctggctcac cagtctaact ctaccaacat cttcttctct 540
ccggtttcta tcgctaccgc tttcgctatg ctgtctctgg gtaccaaagc tgacacccac 600
gacgaaatcc tggaaggtct gaacttcaac ctgaccgaaa tcccggaagc tcagatccac 660
gaaggtttcc aggaactgct gcgtaccctg aaccagccgg actctcagct gcagctgacc 720
accggtaact tcctgttcct gtctgaaggt ctgaaactgg ttgacaaatt cctggaagac 780
gttaaaaaac tgtaccactc tgaagctttc accgttaact tcggtgacac cgaagaagct 840
aaaaaacaga tcaacgacta cgttgaaaaa ggtacccagg gtaaaatcgt tgacctggtt 900
aaagaactgg accgtgacac cgttttcgct ctggttaact acatcttctt caaaggtaaa 960
tgggaacgtc cgttcgaagt taaagacacc gaagaagaag acttccacgt tgaccaggtt 1020
accaccgtta aagttccgat gatgaaacgt ctgggtatgt tcaacatcca gcactgcaaa 1080
aaactgtctt cttgggttct gctgatgaaa tacctgggta acgctaccgc tatcttcttc 1140
ctgccggacg aaggtaaact gcagcacctg gaaaacgaac tgacccacga catcatcacc 1200
aaattcctgg aaaacgaaga ccgtcgttct gcttctctgc acctgccgaa actgtctatc 1260
accggtacct acgacctgaa atctgttctg ggtcagctgg gtatcaccaa agttttctct 1320
aacggtgctg acctgtctgg tgttaccgaa gaagctccgc tgaaactgtc taaagctgtt 1380
cacaaagctg ttctgaccat cgacgaaaaa ggtaccgaag ctgctggtgc tatgttcctg 1440
gaagctatcc cgatgtctat cccgccggaa gttaaattca acaaaccgtt cgttttcctg 1500
atgatcgaac agaacaccaa atctccgctg ttcatgggta aagttgttaa cccgacccag 1560
aaaaaagacg aactgggtgg tgctgctgtt gctctgctgc cggctgttct gctggctctg 1620
ctggctccgg gtggtaaaaa gaagagaaag taactcgagc accaccacca ccaccactg 1679

<210> SEQ ID NO 43
<211> LENGTH: 1625
<212> TYPE: DNA
<213> ORGANISM: Artificial Sequence
<220> FEATURE:
<223> OTHER INFORMATION: Synthetic

<400> SEQUENCE: 43
catatgagag gatcgcatca ccatcaccat cacgattacg atatcccaac gaccgaaaac 60
ctgtattttc agggatccgg tggtggtggt atgcagattt tcgtgagaac ccttacgggg 120
aggaccatca ccctcgaagt tgaaccctcg gatacgatag aaaatgtaag ggccagaatc 180
caggataggg aaggaatacc tcctgatcag cagagactga tctttgctgg caggcagctg 240

```
gaagatggac gtactttgtc tgactacaat attcaaaggg agtctactct tcatcttgtg    300
ttgagacttc gtggtgctgg tggtgaaaca ttttcagacc tatggaaact acttcctgaa    360
aacggtggtg gtggtggtat ggaagacccg cagggtgacg ctgctcagaa aaccgacacc    420
tctcaccacg accaggacca cccgaccttc aacaaaatca ccccgaacct ggctgaattc    480
gctttctctc tgtaccgtca gctggctcac cagtctaact ctaccaacat cttcttctct    540
ccggtttcta tcgctaccgc tttcgctatg ctgtctctgg gtaccaaagc tgacacccac    600
gacgaaatcc tggaaggtct gaacttcaac ctgaccgaaa tcccggaagc tcagatccac    660
gaaggtttcc aggaactgct gcgtaccctg aaccagccgg actctcagct gcagctgacc    720
accggtaact tcctgttcct gtctgaaggt ctgaaactgg ttgacaaatt cctggaagac    780
gttaaaaaac tgtaccactc tgaagctttc accgttaact tcggtgacac cgaagaagct    840
aaaaaacaga tcaacgacta cgttgaaaaa ggtacccagg gtaaaatcgt tgacctggtt    900
aaagaactgg accgtgacac cgttttcgct ctggttaact acatcttctt caaaggtaaa    960
tgggaacgtc cgttcgaagt taaagacacc gaagaagaag acttccacgt tgaccaggtt   1020
accaccgtta aagttccgat gatgaaacgt ctgggtatgt tcaacatcca gcactgcaaa   1080
aaactgtctt cttgggttct gctgatgaaa tacctgggta acgctaccgc tatcttcttc   1140
ctgccggacg aaggtaaact gcagcacctg gaaaacgaac tgacccacga catcatcacc   1200
aaattcctgg aaaacgaaga ccgtcgttct gcttctctgc acctgccgaa actgtctatc   1260
accggtacct acgacctgaa atctgttctg ggtcagctgg gtatcaccaa agttttctct   1320
aacggtgctg acctgtctgg tgttaccgaa gaagctccgc tgaaactgtc taaagctgtt   1380
cacaaagctg ttctgaccat cgacgaaaaa ggtaccgaag ctgctggtgc tatgttcctg   1440
gaagctatcc cgatgtctat cccgccggaa gttaaattca acaaaccgtt cgttttcctg   1500
atgatcgaac agaacaccaa atctccgctg ttcatgggta aagttgttaa cccgacccag   1560
aaaaaagacg aactgggtgg taaaaagaag agaaagtaac tcgagcacca ccaccaccac   1620
cactg                                                               1625
```

<210> SEQ ID NO 44
<211> LENGTH: 2144
<212> TYPE: DNA
<213> ORGANISM: Artificial Sequence
<220> FEATURE:
<223> OTHER INFORMATION: Synthetic

<400> SEQUENCE: 44

```
catatgagag gatcgcatca ccatcaccat cacgattacg atatcccaac gaccgaaaac     60
ctgtattttc agggatccgg tggtggtggt atgcagattt tcgtgagaac ccttacgggg    120
aggaccatca ccctcgaagt tgaaccctcg gatacgatag aaaatgtaag ggccagaatc    180
caggataggg aaggaatacc tcctgatcag cagagactga tctttgctgg caggcagctg    240
gaagatggac gtactttgtc tgactacaat attcaaaggg agtctactct tcatcttgtg    300
ttgagacttc gtggtgctgg tggtatggct gaaccgtggg gtaacgaact ggcttctgct    360
gctgctcgtg gtgacctgga acagctgacc tctctgctgc agaacaacgt taacgttaac    420
gctcagaacg gtttcggtcg taccgctctg caggttatga aactgggtaa cccggaaatc    480
gctcgtcgtc tgctgctgcg tggtgctaac ccggacctga aagaccgtac cggtaacgct    540
gttatccacg acgctgctcg tgctggtttc ctggacaccc tgcagaccct gctggaattc    600
caggctgacg ttaacatcga agacaacgaa ggtaacctgc cgctgcacct ggctgctaaa    660
```

```
gaaggtcacc tgcgtgttgt tgaattcctg gttaaacaca ccgcttctaa cgttggtcac     720

cgtaaccaca aaggtgacac cgcttgcgac ctggctcgtc tgtacggtcg taacgaagtt     780

gtttctctga tgcaggctaa cggtgctggt ggtgctacca acctgcaggg tggtggtggt     840

ggtatggaag acccgcaggg tgacgctgct cagaaaaccg acacctctca ccacgaccag     900

gaccacccga ccttcaacaa aatcaccccg aacctggctg aattcgcttt ctctctgtac     960

cgtcagctgg ctcaccagtc taactctacc aacatcttct tctctccggt ttctatcgct    1020

accgctttcg ctatgctgtc tctgggtacc aaagctgaca cccacgacga aatcctggaa    1080

ggtctgaact tcaacctgac cgaaatcccg gaagctcaga tccacgaagg tttccaggaa    1140

ctgctgcgta ccctgaacca gccggactct cagctgcagc tgaccaccgg taacttcctg    1200

ttcctgtctg aaggtctgaa actggttgac aaattcctgg aagacgttaa aaaactgtac    1260

cactctgaag ctttcaccgt taacttcggt gacaccgaag aagctaaaaa acagatcaac    1320

gactacgttg aaaaaggtac ccagggtaaa atcgttgacc tggttaaaga actggaccgt    1380

gacaccgttt tcgctctggt taactacatc ttcttcaaag gtaaatggga acgtccgttc    1440

gaagttaaag acaccgaaga agaagacttc cacgttgacc aggttaccac cgttaaagtt    1500

ccgatgatga aacgtctggg tatgttcaac atccagcact gcaaaaaact gtcttcttgg    1560

gttctgctga tgaaatacct gggtaacgct accgctatct tcttcctgcc ggacgaaggt    1620

aaactgcagc acctggaaaa cgaactgacc cacgacatca tcaccaaatt cctggaaaac    1680

gaagaccgtc gttctgcttc tctgcacctg ccgaaactgt ctatcaccgg tacctacgac    1740

ctgaaatctg ttctgggtca gctgggtatc accaaagttt tctctaacgg tgctgacctg    1800

tctggtgtta ccgaagaagc tccgctgaaa ctgtctaaag ctgttcacaa agctgttctg    1860

accatcgacg aaaaaggtac cgaagctgct ggtgctatgt tcctggaagc tatcccgatg    1920

tctatcccgc cggaagttaa attcaacaaa ccgttcgttt tcctgatgat cgaacagaac    1980

accaaatctc cgctgttcat gggtaaagtt gttaacccga cccagaaaaa agacgaactg    2040

ggtggtgctg ctgttgctct gctgccggct gttctgctgg ctctgctggc tccgggtggt    2100

aaaaagaaga gaaagtaact cgagcaccac caccaccacc actg                     2144
```

<210> SEQ ID NO 45
<211> LENGTH: 2090
<212> TYPE: DNA
<213> ORGANISM: Artificial Sequence
<220> FEATURE:
<223> OTHER INFORMATION: Synthetic

<400> SEQUENCE: 45

```
catatgagag gatcgcatca ccatcaccat cacgattacg atatcccaac gaccgaaaac      60

ctgtattttc agggatccgg tggtggtggt atgcagattt tcgtgagaac ccttacgggg     120

aggaccatca ccctcgaagt tgaaccctcg gatacgatag aaaatgtaag ggccagaatc     180

caggataggg aaggaatacc tcctgatcag cagagactga tctttgctgg caggcagctg     240

gaagatggac gtactttgtc tgactacaat attcaaaggg agtctactct tcatcttgtg     300

ttgagacttc gtggtgctgg tggtatggct gaaccgtggg gtaacgaact ggcttctgct     360

gctgctcgtg gtgacctgga acagctgacc tctctgctgc agaacaacgt taacgttaac     420

gctcagaacg gtttcggtcg taccgctctg caggttatga aactgggtaa cccggaaatc     480

gctcgtcgtc tgctgctgcg tggtgctaac ccggacctga aagaccgtac cggtaacgct     540
```

```
gttatccacg acgctgctcg tgctggtttc ctggacaccc tgcagaccct gctggaattc    600

caggctgacg ttaacatcga agacaacgaa ggtaacctgc cgctgcacct ggctgctaaa    660

gaaggtcacc tgcgtgttgt tgaattcctg gttaaacaca ccgcttctaa cgttggtcac    720

cgtaaccaca aggtgacac cgcttgcgac ctggctcgtc tgtacggtcg taacgaagtt     780

gtttctctga tgcaggctaa cggtgctggt ggtgctacca acctgcaggg tggtggtggt    840

ggtatggaag acccgcaggg tgacgctgct cagaaaaccg acacctctca ccacgaccag    900

gaccacccga ccttcaacaa aatcaccccg aacctggctg aattcgcttt ctctctgtac    960

cgtcagctgg ctcaccagtc taactctacc aacatcttct tctctccggt ttctatcgct   1020

accgctttcg ctatgctgtc tctgggtacc aaagctgaca cccacgacga aatcctggaa   1080

ggtctgaact tcaacctgac cgaaatcccg gaagctcaga tccacgaagg tttccaggaa   1140

ctgctgcgta ccctgaacca gccggactct cagctgcagc tgaccaccgg taacttcctg   1200

ttcctgtctg aaggtctgaa actggttgac aaattcctgg aagacgttaa aaaactgtac   1260

cactctgaag ctttcaccgt taacttcggt gacaccgaag aagctaaaaa acagatcaac   1320

gactacgttg aaaaaggtac ccagggtaaa atcgttgacc tggttaaaga actggaccgt   1380

gacaccgttt tcgctctggt taactacatc ttcttcaaag gtaaatggga acgtccgttc   1440

gaagttaaag acaccgaaga agaagacttc cacgttgacc aggttaccac cgttaaagtt   1500

ccgatgatga aacgtctggg tatgttcaac atccagcact gcaaaaaact gtcttcttgg   1560

gttctgctga tgaaatacct gggtaacgct accgctatct tcttcctgcc ggacgaaggt   1620

aaactgcagc acctggaaaa cgaactgacc cacgacatca tcaccaaatt cctggaaaac   1680

gaagaccgtc gttctgcttc tctgcacctg ccgaaactgt ctatcaccgg tacctacgac   1740

ctgaaatctg ttctgggtca gctgggtatc accaaagttt tctctaacgg tgctgacctg   1800

tctggtgtta ccgaagaagc tccgctgaaa ctgtctaaag ctgttcacaa agctgttctg   1860

accatcgacg aaaaaggtac cgaagctgct ggtgctatgt tcctggaagc tatcccgatg   1920

tctatcccgc cggaagttaa attcaacaaa ccgttcgttt tcctgatgat cgaacagaac   1980

accaaatctc cgctgttcat gggtaaagtt gttaacccga cccagaaaaa agacgaactg   2040

ggtggtaaaa agaagagaaa gtaactcgag caccaccacc accaccactg              2090
```

```
<210> SEQ ID NO 46
<211> LENGTH: 2189
<212> TYPE: DNA
<213> ORGANISM: Artificial Sequence
<220> FEATURE:
<223> OTHER INFORMATION: Synthetic

<400> SEQUENCE: 46
```

```
catatgagag gatcgcatca ccatcaccat cacgattacg atatcccaac gaccgaaaac     60

ctgtattttc agggatccgg tggtggtggt atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctgg tggtgaaaca ttttcagacc tatggaaact acttcctgaa    360

aacggtggtg gtggtggtat ggctgaaccg tggggtaacg aactggcttc tgctgctgct    420

cgtggtgacc tggaacagct gacctctctg ctgcagaaca acgttaacgt taacgctcag    480

aacggtttcg gtcgtaccgc tctgcaggtt atgaaactgg gtaacccgga aatcgctcgt    540
```

```
cgtctgctgc tgcgtggtgc taacccggac ctgaaagacc gtaccggtaa cgctgttatc    600

cacgacgctg ctcgtgctgg tttcctggac accctgcaga ccctgctgga attccaggct    660

gacgttaaca tcgaagacaa cgaaggtaac ctgccgctgc acctggctgc taaagaaggt    720

cacctgcgtg ttgttgaatt cctggttaaa cacaccgctt ctaacgttgg tcaccgtaac    780

cacaaaggtg acaccgcttg cgacctggct cgtctgtacg gtcgtaacga agttgtttct    840

ctgatgcagg ctaacggtgc tggtggtgct accaacctgc agggtggtat ggaagacccg    900

cagggtgacg ctgctcagaa aaccgacacc tctcaccacg accaggacca cccgaccttc    960

aacaaaatca ccccgaacct ggctgaattc gctttctctc tgtaccgtca gctggctcac   1020

cagtctaact ctaccaacat cttcttctct ccggtttcta tcgctaccgc tttcgctatg   1080

ctgtctctgg gtaccaaagc tgacacccac gacgaaatcc tggaaggtct gaacttcaac   1140

ctgaccgaaa tcccggaagc tcagatccac gaaggtttcc aggaactgct gcgtaccctg   1200

aaccagccgg actctcagct gcagctgacc accggtaact tcctgttcct gtctgaaggt   1260

ctgaaactgg ttgacaaatt cctggaagac gttaaaaaac tgtaccactc tgaagctttc   1320

accgttaact tcggtgacac cgaagaagct aaaaaacaga tcaacgacta cgttgaaaaa   1380

ggtacccagg gtaaaatcgt tgacctggtt aaagaactgg accgtgacac cgttttcgct   1440

ctggttaact acatcttctt caaaggtaaa tgggaacgtc cgttcgaagt taaagacacc   1500

gaagaagaag acttccacgt tgaccaggtt accaccgtta aagttccgat gatgaaacgt   1560

ctgggtatgt tcaacatcca gcactgcaaa aaactgtctt cttgggttct gctgatgaaa   1620

tacctgggta acgctaccgc tatcttcttc ctgccggacg aaggtaaact gcagcacctg   1680

gaaaacgaac tgacccacga catcatcacc aaattcctgg aaaacgaaga ccgtcgttct   1740

gcttctctgc acctgccgaa actgtctatc accggtacct acgacctgaa atctgttctg   1800

ggtcagctgg gtatcaccaa agttttctct aacggtgctg acctgtctgg tgttaccgaa   1860

gaagctccgc tgaaactgtc taaagctgtt cacaaagctg ttctgaccat cgacgaaaaa   1920

ggtaccgaag ctgctggtgc tatgttcctg gaagctatcc cgatgtctat cccgccggaa   1980

gttaaattca acaaaccgtt cgttttcctg atgatcgaac agaacaccaa atctccgctg   2040

ttcatgggta aagttgttaa cccgacccag aaaaaagacg aactgggtgg tgctgctgtt   2100

gctctgctgc cggctgttct gctggctctg ctggctccgg gtggtaaaaa gaagagaaag   2160

taactcgagc accaccacca ccaccactg                                    2189
```

<210> SEQ ID NO 47
<211> LENGTH: 2135
<212> TYPE: DNA
<213> ORGANISM: Artificial Sequence
<220> FEATURE:
<223> OTHER INFORMATION: Synthetic

<400> SEQUENCE: 47

```
catatgagag gatcgcatca ccatcaccat cacgattacg atatcccaac gaccgaaaac     60

ctgtattttc agggatccgg tggtggtggt atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctgg tggtgaaaca ttttcagacc tatggaaact acttcctgaa    360
```

```
aacggtggtg gtggtggtat ggctgaaccg tggggtaacg aactggcttc tgctgctgct    420

cgtggtgacc tggaacagct gacctctctg ctgcagaaca acgttaacgt taacgctcag    480

aacggtttcg gtcgtaccgc tctgcaggtt atgaaactgg gtaacccgga aatcgctcgt    540

cgtctgctgc tgcgtggtgc taacccggac ctgaaagacc gtaccggtaa cgctgttatc    600

cacgacgctg ctcgtgctgg tttcctggac accctgcaga ccctgctgga attccaggct    660

gacgttaaca tcgaagacaa cgaaggtaac ctgccgctgc acctggctgc taaagaaggt    720

cacctgcgtg ttgttgaatt cctggttaaa cacaccgctt ctaacgttgg tcaccgtaac    780

cacaaaggtg acaccgcttg cgacctggct cgtctgtacg gtcgtaacga agttgtttct    840

ctgatgcagg ctaacggtgc tggtggtgct accaacctgc agggtggtat ggaagacccg    900

cagggtgacg ctgctcagaa aaccgacacc tctcaccacg accaggacca cccgaccttc    960

aacaaaatca ccccgaacct ggctgaattc gctttctctc tgtaccgtca gctggctcac   1020

cagtctaact ctaccaacat cttcttctct ccggtttcta tcgctaccgc tttcgctatg   1080

ctgtctctgg gtaccaaagc tgacacccac gacgaaatcc tggaaggtct gaacttcaac   1140

ctgaccgaaa tcccggaagc tcagatccac gaaggtttcc aggaactgct gcgtaccctg   1200

aaccagccgg actctcagct gcagctgacc accggtaact tcctgttcct gtctgaaggt   1260

ctgaaactgg ttgacaaatt cctggaagac gttaaaaaac tgtaccactc tgaagctttc   1320

accgttaact tcggtgacac cgaagaagct aaaaaacaga tcaacgacta cgttgaaaaa   1380

ggtacccagg gtaaaatcgt tgacctggtt aaagaactgg accgtgacac cgttttcgct   1440

ctggttaact acatcttctt caaaggtaaa tgggaacgtc cgttcgaagt taaagacacc   1500

gaagaagaag acttccacgt tgaccaggtt accaccgtta aagttccgat gatgaaacgt   1560

ctgggtatgt tcaacatcca gcactgcaaa aaactgtctt cttgggttct gctgatgaaa   1620

tacctgggta acgctaccgc tatcttcttc ctgccggacg aaggtaaact gcagcacctg   1680

gaaaacgaac tgacccacga catcatcacc aaattcctgg aaaacgaaga ccgtcgttct   1740

gcttctctgc acctgccgaa actgtctatc accggtacct acgacctgaa atctgttctg   1800

ggtcagctgg gtatcaccaa agttttctct aacggtgctg acctgtctgg tgttaccgaa   1860

gaagctccgc tgaaactgtc taaagctgtt cacaaagctg ttctgaccat cgacgaaaaa   1920

ggtaccgaag ctgctggtgc tatgttcctg gaagctatcc cgatgtctat cccgccggaa   1980

gttaaattca acaaaccgtt cgttttcctg atgatcgaac agaacaccaa atctccgctg   2040

ttcatgggta aagttgttaa cccgacccag aaaaaagacg aactgggtgg taaaaagaag   2100

agaaagtaac tcgagcacca ccaccaccac cactg                              2135
```

```
<210> SEQ ID NO 48
<211> LENGTH: 2186
<212> TYPE: DNA
<213> ORGANISM: Artificial Sequence
<220> FEATURE:
<223> OTHER INFORMATION: Synthetic

<400> SEQUENCE: 48

catatgagag gatcgcatca ccatcaccat cacgattacg atatcccaac gaccgaaaac     60

ctgtattttc agggatccgg tggtggtggt atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300
```

```
ttgagacttc gtggtgctgg tggtgaaacc ttcgaacact ggtggtctca gctgctgtct    360

ggtggtggtg gtggtatggc tgaaccgtgg ggtaacgaac tggcttctgc tgctgctcgt    420

ggtgacctgg aacagctgac ctctctgctg cagaacaacg ttaacgttaa cgctcagaac    480

ggtttcggtc gtaccgctct gcaggttatg aaactgggta acccggaaat cgctcgtcgt    540

ctgctgctgc gtggtgctaa cccggacctg aaagaccgta ccggtaacgc tgttatccac    600

gacgctgctc gtgctggttt cctggacacc ctgcagaccc tgctggaatt ccaggctgac    660

gttaacatcg aagacaacga aggtaacctg ccgctgcacc tggctgctaa agaaggtcac    720

ctgcgtgttg ttgaattcct ggttaaacac accgcttcta acgttggtca ccgtaaccac    780

aaaggtgaca ccgcttgcga cctggctcgt ctgtacggtc gtaacgaagt tgtttctctg    840

atgcaggcta acggtgctgg tggtgctacc aacctgcagg gtggtatgga agacccgcag    900

ggtgacgctg ctcagaaaac cgacacctct caccacgacc aggaccaccc gaccttcaac    960

aaaatcaccc cgaacctggc tgaattcgct ttctctctgt accgtcagct ggctcaccag   1020

tctaactcta ccaacatctt cttctctccg gtttctatcg ctaccgcttt cgctatgctg   1080

tctctgggta ccaaagctga cacccacgac gaaatcctgg aaggtctgaa cttcaacctg   1140

accgaaatcc cggaagctca gatccacgaa ggtttccagg aactgctgcg taccctgaac   1200

cagccggact ctcagctgca gctgaccacc ggtaacttcc tgttcctgtc tgaaggtctg   1260

aaactggttg acaaattcct ggaagacgtt aaaaaactgt accactctga agctttcacc   1320

gttaacttcg gtgacaccga agaagctaaa aaacagatca acgactacgt tgaaaaaggt   1380

acccagggta aaatcgttga cctggttaaa gaactggacc gtgacaccgt tttcgctctg   1440

gttaactaca tcttcttcaa aggtaaatgg gaacgtccgt tcgaagttaa agacaccgaa   1500

gaagaagact tccacgttga ccaggttacc accgttaaag ttccgatgat gaaacgtctg   1560

ggtatgttca acatccagca ctgcaaaaaa ctgtcttctt gggttctgct gatgaaatac   1620

ctgggtaacg ctaccgctat cttcttcctg ccggacgaag gtaaactgca gcacctggaa   1680

aacgaactga cccacgacat catcaccaaa ttcctggaaa acgaagaccg tcgttctgct   1740

tctctgcacc tgccgaaact gtctatcacc ggtacctacg acctgaaatc tgttctgggt   1800

cagctgggta tcaccaaagt tttctctaac ggtgctgacc tgtctggtgt taccgaagaa   1860

gctccgctga aactgtctaa agctgttcac aaagctgttc tgaccatcga cgaaaaaggt   1920

accgaagctg ctggtgctat gttcctggaa gctatcccga tgtctatccc gccggaagtt   1980

aaattcaaca aaccgttcgt tttcctgatg atcgaacaga acaccaaatc tccgctgttc   2040

atgggtaaag ttgttaaccc gacccagaaa aaagacgaac tgggtggtgc tgctgttgct   2100

ctgctgccgg ctgttctgct ggctctgctg gctccgggtg gtaaaaagaa gagaaagtaa   2160

ctcgagcacc accaccacca ccactg                                         2186
```

<210> SEQ ID NO 49
<211> LENGTH: 1676
<212> TYPE: DNA
<213> ORGANISM: Artificial Sequence
<220> FEATURE:
<223> OTHER INFORMATION: Synthetic

<400> SEQUENCE: 49

```
catatgagag gatcgcatca ccatcaccat cacgattacg atatcccaac gaccgaaaac     60

ctgtattttc agggatccgg tggtggtggt atgcagattt tcgtgagaac ccttacgggg    120
```

```
aggaccatca ccctcgaagt tgaaccctcg gatacgatag aaaatgtaag ggccagaatc    180
caggataggg aaggaatacc tcctgatcag cagagactga tctttgctgg caggcagctg    240
gaagatggac gtactttgtc tgactacaat attcaaaggg agtctactct tcatcttgtg    300
ttgagacttc gtggtgctgg tggtgaaacc ttcgaacact ggtggtctca gctgctgtct    360
ggtggtggtg gtggtatgga agacccgcag ggtgacgctg ctcagaaaac cgacacctct    420
caccacgacc aggaccaccc gaccttcaac aaaatcaccc cgaacctggc tgaattcgct    480
ttctctctgt accgtcagct ggctcaccag tctaactcta ccaacatctt cttctctccg    540
gtttctatcg ctaccgcttt cgctatgctg tctctgggta ccaaagctga cacccacgac    600
gaaatcctgg aaggtctgaa cttcaacctg accgaaatcc cggaagctca gatccacgaa    660
ggtttccagg aactgctgcg taccctgaac cagccggact ctcagctgca gctgaccacc    720
ggtaacttcc tgttcctgtc tgaaggtctg aaactggttg acaaattcct ggaagacgtt    780
aaaaaactgt accactctga agctttcacc gttaacttcg gtgacaccga agaagctaaa    840
aaacagatca acgactacgt tgaaaaaggt acccagggta aaatcgttga cctggttaaa    900
gaactggacc gtgacaccgt tttcgctctg gttaactaca tcttcttcaa aggtaaatgg    960
gaacgtccgt tcgaagttaa agacaccgaa gaagaagact tccacgttga ccaggttacc   1020
accgttaaag ttccgatgat gaaacgtctg ggtatgttca acatccagca ctgcaaaaaa   1080
ctgtcttctt gggttctgct gatgaaatac ctgggtaacg ctaccgctat cttcttcctg   1140
ccggacgaag gtaaactgca gcacctggaa aacgaactga cccacgacat catcaccaaa   1200
ttcctggaaa acgaagaccg tcgttctgct tctctgcacc tgccgaaact gtctatcacc   1260
ggtacctacg acctgaaatc tgttctgggt cagctgggta tcaccaaagt tttctctaac   1320
ggtgctgacc tgtctggtgt taccgaagaa gctccgctga aactgtctaa agctgttcac   1380
aaagctgttc tgaccatcga cgaaaaaggt accgaagctg ctggtgctat gttcctggaa   1440
gctatcccga tgtctatccc gccggaagtt aaattcaaca aaccgttcgt tttcctgatg   1500
atcgaacaga acaccaaatc tccgctgttc atgggtaaag ttgttaaccc gacccagaaa   1560
aaagacgaac tgggtggtgc tgctgttgct ctgctgccgg ctgttctgct ggctctgctg   1620
gctccgggtg gtaaaaagaa gagaaagtaa ctcgagcacc accaccacca ccactg       1676
```

```
<210> SEQ ID NO 50
<211> LENGTH: 2186
<212> TYPE: DNA
<213> ORGANISM: Artificial Sequence
<220> FEATURE:
<223> OTHER INFORMATION: Synthetic

<400> SEQUENCE: 50

catatgagag gatcgcatca ccatcaccat cacgattacg atatcccaac gaccgaaaac     60
ctgtattttc agggatccgg tggtggtggt atgcagattt tcgtgagaac ccttacgggg    120
aggaccatca ccctcgaagt tgaaccctcg gatacgatag aaaatgtaag ggccagaatc    180
caggataggg aaggaatacc tcctgatcag cagagactga tctttgctgg caggcagctg    240
gaagatggac gtactttgtc tgactacaat attcaaaggg agtctactct tcatcttgtg    300
ttgagacttc gtggtgctgg tggtacctct ttcgctgaat actggaacct gctgtctccg    360
ggtggtggtg gtggtatggc tgaaccgtgg ggtaacgaac tggcttctgc tgctgctcgt    420
ggtgacctgg aacagctgac ctctctgctg cagaacaacg ttaacgttaa cgctcagaac    480
ggtttcggtc gtaccgctct gcaggttatg aaactgggta acccggaaat cgctcgtcgt    540
```

```
ctgctgctgc gtggtgctaa cccggacctg aaagaccgta ccggtaacgc tgttatccac    600

gacgctgctc gtgctggttt cctggacacc ctgcagaccc tgctggaatt ccaggctgac    660

gttaacatcg aagacaacga aggtaacctg ccgctgcacc tggctgctaa agaaggtcac    720

ctgcgtgttg ttgaattcct ggttaaacac accgcttcta acgttggtca ccgtaaccac    780

aaaggtgaca ccgcttgcga cctggctcgt ctgtacggtc gtaacgaagt tgtttctctg    840

atgcaggcta acggtgctgg tggtgctacc aacctgcagg gtggtatgga agacccgcag    900

ggtgacgctg ctcagaaaac cgacacctct caccacgacc aggaccaccc gaccttcaac    960

aaaatcaccc cgaacctggc tgaattcgct ttctctctgt accgtcagct ggctcaccag   1020

tctaactcta ccaacatctt cttctctccg gtttctatcg ctaccgcttt cgctatgctg   1080

tctctgggta ccaaagctga cacccacgac gaaatcctgg aaggtctgaa cttcaacctg   1140

accgaaatcc cggaagctca gatccacgaa ggtttccagg aactgctgcg taccctgaac   1200

cagccggact ctcagctgca gctgaccacc ggtaacttcc tgttcctgtc tgaaggtctg   1260

aaactggttg acaaattcct ggaagacgtt aaaaaactgt accactctga agctttcacc   1320

gttaacttcg gtgacaccga agaagctaaa aaacagatca acgactacgt tgaaaaaggt   1380

acccagggta aaatcgttga cctggttaaa gaactggacc gtgacaccgt tttcgctctg   1440

gttaactaca tcttcttcaa aggtaaatgg gaacgtccgt tcgaagttaa agacaccgaa   1500

gaagaagact tccacgttga ccaggttacc accgttaaag ttccgatgat gaaacgtctg   1560

ggtatgttca acatccagca ctgcaaaaaa ctgtcttctt gggttctgct gatgaaatac   1620

ctgggtaacg ctaccgctat cttcttcctg ccggacgaag gtaaactgca gcacctggaa   1680

aacgaactga cccacgacat catcaccaaa ttcctggaaa acgaagaccg tcgttctgct   1740

tctctgcacc tgccgaaact gtctatcacc ggtacctacg acctgaaatc tgttctgggt   1800

cagctgggta tcaccaaagt tttctctaac ggtgctgacc tgtctggtgt taccgaagaa   1860

gctccgctga aactgtctaa agctgttcac aaagctgttc tgaccatcga cgaaaaaggt   1920

accgaagctg ctggtgctat gttcctggaa gctatcccga tgtctatccc gccggaagtt   1980

aaattcaaca aaccgttcgt tttcctgatg atcgaacaga acaccaaatc tccgctgttc   2040

atgggtaaag ttgttaaccc gacccagaaa aaagacgaac tgggtggtgc tgctgttgct   2100

ctgctgccgg ctgttctgct ggctctgctg gctccgggtg gtaaaaagaa gagaaagtaa   2160

ctcgagcacc accaccacca ccactg                                        2186
```

<210> SEQ ID NO 51
<211> LENGTH: 1676
<212> TYPE: DNA
<213> ORGANISM: Artificial Sequence
<220> FEATURE:
<223> OTHER INFORMATION: Synthetic

<400> SEQUENCE: 51

```
catatgagag gatcgcatca ccatcaccat cacgattacg atatcccaac gaccgaaaac     60

ctgtattttc agggatccgg tggtggtggt atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctgg tggtacctct ttcgctgaat actggaacct gctgtctccg    360
```

```
ggtggtggtg gtggtatgga agacccgcag ggtgacgctg ctcagaaaac cgacacctct    420

caccacgacc aggaccaccc gaccttcaac aaaatcaccc cgaacctggc tgaattcgct    480

ttctctctgt accgtcagct ggctcaccag tctaactcta ccaacatctt cttctctccg    540

gtttctatcg ctaccgcttt cgctatgctg tctctgggta ccaaagctga cacccacgac    600

gaaatcctgg aaggtctgaa cttcaacctg accgaaatcc cggaagctca gatccacgaa    660

ggtttccagg aactgctgcg taccctgaac cagccggact ctcagctgca gctgaccacc    720

ggtaacttcc tgttcctgtc tgaaggtctg aaactggttg acaaattcct ggaagacgtt    780

aaaaaactgt accactctga agctttcacc gttaacttcg gtgacaccga agaagctaaa    840

aaacagatca acgactacgt tgaaaaaggt acccagggta aaatcgttga cctggttaaa    900

gaactggacc gtgacaccgt tttcgctctg gttaactaca tcttcttcaa aggtaaatgg    960

gaacgtccgt tcgaagttaa agacaccgaa gaagaagact tccacgttga ccaggttacc   1020

accgttaaag ttccgatgat gaaacgtctg ggtatgttca acatccagca ctgcaaaaaa   1080

ctgtcttctt gggttctgct gatgaaatac ctgggtaacg ctaccgctat cttcttcctg   1140

ccggacgaag gtaaactgca gcacctggaa aacgaactga cccacgacat catcaccaaa   1200

ttcctggaaa acgaagaccg tcgttctgct tctctgcacc tgccgaaact gtctatcacc   1260

ggtacctacg acctgaaatc tgttctgggt cagctgggta tcaccaaagt tttctctaac   1320

ggtgctgacc tgtctggtgt taccgaagaa gctccgctga aactgtctaa agctgttcac   1380

aaagctgttc tgaccatcga cgaaaaaggt accgaagctg ctggtgctat gttcctggaa   1440

gctatcccga tgtctatccc gccggaagtt aaattcaaca aaccgttcgt tttcctgatg   1500

atcgaacaga acaccaaatc tccgctgttc atgggtaaag ttgttaaccc gacccagaaa   1560

aaagacgaac tgggtggtgc tgctgttgct ctgctgccgg ctgttctgct ggctctgctg   1620

gctccgggtg gtaaaaagaa gagaaagtaa ctcgagcacc accaccacca ccactg       1676
```

<210> SEQ ID NO 52
<211> LENGTH: 2186
<212> TYPE: DNA
<213> ORGANISM: Artificial Sequence
<220> FEATURE:
<223> OTHER INFORMATION: Synthetic

<400> SEQUENCE: 52

```
catatgagag gatcgcatca ccatcaccat cacgattacg atatcccaac gaccgaaaac     60

ctgtattttc agggatccgg tggtggtggt atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctgg tggtgaaacc ttcgaacact ggtggaacct gctgtctccg    360

ggtggtggtg gtggtatggc tgaaccgtgg ggtaacgaac tggcttctgc tgctgctcgt    420

ggtgacctgg aacagctgac ctctctgctg cagaacaacg ttaacgttaa cgctcagaac    480

ggtttcggtc gtaccgctct gcaggttatg aaactgggta acccggaaat cgctcgtcgt    540

ctgctgctgc gtggtgctaa cccggacctg aaagaccgta ccggtaacgc tgttatccac    600

gacgctgctc gtgctggttt cctggacacc ctgcagaccc tgctggaatt ccaggctgac    660

gttaacatcg aagacaacga aggtaacctg ccgctgcacc tggctgctaa agaaggtcac    720

ctgcgtgttg ttgaattcct ggttaaacac accgcttcta acgttggtca ccgtaaccac    780
```

```
aaaggtgaca ccgcttgcga cctggctcgt ctgtacggtc gtaacgaagt tgtttctctg    840

atgcaggcta acggtgctgg tggtgctacc aacctgcagg gtggtatgga agacccgcag    900

ggtgacgctg ctcagaaaac cgacacctct caccacgacc aggaccaccc gaccttcaac    960

aaaatcaccc cgaacctggc tgaattcgct ttctctctgt accgtcagct ggctcaccag   1020

tctaactcta ccaacatctt cttctctccg gtttctatcg ctaccgcttt cgctatgctg   1080

tctctgggta ccaaagctga cacccacgac gaaatcctgg aaggtctgaa cttcaacctg   1140

accgaaatcc cggaagctca gatccacgaa ggtttccagg aactgctgcg taccctgaac   1200

cagccggact ctcagctgca gctgaccacc ggtaacttcc tgttcctgtc tgaaggtctg   1260

aaactggttg acaaattcct ggaagacgtt aaaaaactgt accactctga agctttcacc   1320

gttaacttcg gtgacaccga agaagctaaa aaacagatca acgactacgt tgaaaaaggt   1380

acccagggta aaatcgttga cctggttaaa gaactggacc gtgacaccgt tttcgctctg   1440

gttaactaca tcttcttcaa aggtaaatgg gaacgtccgt tcgaagttaa agacaccgaa   1500

gaagaagact tccacgttga ccaggttacc accgttaaag ttccgatgat gaaacgtctg   1560

ggtatgttca acatccagca ctgcaaaaaa ctgtcttctt gggttctgct gatgaaatac   1620

ctgggtaacg ctaccgctat cttcttcctg ccggacgaag gtaaactgca gcacctggaa   1680

aacgaactga cccacgacat catcaccaaa ttcctggaaa acgaagaccg tcgttctgct   1740

tctctgcacc tgccgaaact gtctatcacc ggtacctacg acctgaaatc tgttctgggt   1800

cagctgggta tcaccaaagt tttctctaac ggtgctgacc tgtctggtgt taccgaagaa   1860

gctccgctga aactgtctaa agctgttcac aaagctgttc tgaccatcga cgaaaaaggt   1920

accgaagctg ctggtgctat gttcctggaa gctatcccga tgtctatccc gccggaagtt   1980

aaattcaaca aaccgttcgt tttcctgatg atcgaacaga acaccaaatc tccgctgttc   2040

atgggtaaag ttgttaaccc gacccagaaa aaagacgaac tgggtggtgc tgctgttgct   2100

ctgctgccgg ctgttctgct ggctctgctg gctccgggtg gtaaaaagaa gagaaagtaa   2160

ctcgagcacc accaccacca ccactg                                        2186
```

<210> SEQ ID NO 53
<211> LENGTH: 1676
<212> TYPE: DNA
<213> ORGANISM: Artificial Sequence
<220> FEATURE:
<223> OTHER INFORMATION: Synthetic

<400> SEQUENCE: 53

```
catatgagag gatcgcatca ccatcaccat cacgattacg atatcccaac gaccgaaaac     60

ctgtattttc agggatccgg tggtggtggt atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctgg tggtgaaacc ttcgaacact ggtggaacct gctgtctccg    360

ggtggtggtg gtggtatgga agacccgcag ggtgacgctg ctcagaaaac cgacacctct    420

caccacgacc aggaccaccc gaccttcaac aaaatcaccc cgaacctggc tgaattcgct    480

ttctctctgt accgtcagct ggctcaccag tctaactcta ccaacatctt cttctctccg    540

gtttctatcg ctaccgcttt cgctatgctg tctctgggta ccaaagctga cacccacgac    600
```

```
gaaatcctgg aaggtctgaa cttcaacctg accgaaatcc cggaagctca gatccacgaa    660

ggtttccagg aactgctgcg taccctgaac cagccggact ctcagctgca gctgaccacc    720

ggtaacttcc tgttcctgtc tgaaggtctg aaactggttg acaaattcct ggaagacgtt    780

aaaaaactgt accactctga agctttcacc gttaacttcg gtgacaccga agaagctaaa    840

aaacagatca acgactacgt tgaaaaaggt acccagggta aaatcgttga cctggttaaa    900

gaactggacc gtgacaccgt tttcgctctg gttaactaca tcttcttcaa aggtaaatgg    960

gaacgtccgt tcgaagttaa agacaccgaa gaagaagact tccacgttga ccaggttacc   1020

accgttaaag ttccgatgat gaaacgtctg ggtatgttca acatccagca ctgcaaaaaa   1080

ctgtcttctt gggttctgct gatgaaatac ctgggtaacg ctaccgctat cttcttcctg   1140

ccggacgaag gtaaactgca gcacctggaa aacgaactga cccacgacat catcaccaaa   1200

ttcctggaaa acgaagaccg tcgttctgct tctctgcacc tgccgaaact gtctatcacc   1260

ggtacctacg acctgaaatc tgttctgggt cagctgggta tcaccaaagt tttctctaac   1320

ggtgctgacc tgtctggtgt taccgaagaa gctccgctga aactgtctaa agctgttcac   1380

aaagctgttc tgaccatcga cgaaaaaggt accgaagctg ctggtgctat gttcctggaa   1440

gctatcccga tgtctatccc gccggaagtt aaattcaaca aaccgttcgt tttcctgatg   1500

atcgaacaga acaccaaatc tccgctgttc atgggtaaag ttgttaaccc gacccagaaa   1560

aaagacgaac tgggtggtgc tgctgttgct ctgctgccgg ctgttctgct ggctctgctg   1620

gctccgggtg gtaaaaagaa gagaaagtaa ctcgagcacc accaccacca ccactg       1676
```

<210> SEQ ID NO 54
<211> LENGTH: 149
<212> TYPE: PRT
<213> ORGANISM: Artificial Sequence
<220> FEATURE:
<223> OTHER INFORMATION: Synthetic

<400> SEQUENCE: 54

```
Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Ala Ala Val Ala Leu
            100                 105                 110

Leu Pro Ala Val Leu Leu Ala Leu Leu Ala Pro Gly Gly Lys Lys Lys
        115                 120                 125

Arg Lys Gly Gly Gly Gly Gly Ser Asp Ile Cys Leu Pro Arg Trp Gly
    130                 135                 140

Cys Leu Trp Glu Asp
145
```

<210> SEQ ID NO 55
<211> LENGTH: 131

<212> TYPE: PRT
<213> ORGANISM: Artificial Sequence
<220> FEATURE:
<223> OTHER INFORMATION: Synthetic

<400> SEQUENCE: 55

```
Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Lys Lys Lys Arg Lys
            100                 105                 110

Gly Gly Gly Gly Gly Ser Asp Ile Cys Leu Pro Arg Trp Gly Cys Leu
        115                 120                 125

Trp Glu Asp
    130
```

<210> SEQ ID NO 56
<211> LENGTH: 337
<212> TYPE: PRT
<213> ORGANISM: Artificial Sequence
<220> FEATURE:
<223> OTHER INFORMATION: Synthetic

<400> SEQUENCE: 56

```
Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Ala Ala Val Ala Leu
            100                 105                 110

Leu Pro Ala Val Leu Leu Ala Leu Leu Ala Pro Gly Gly Glu Thr Phe
        115                 120                 125

Ser Asp Leu Trp Lys Leu Leu Pro Glu Asn Gly Gly Gly Gly Gly Met
    130                 135                 140

Ala Glu Pro Trp Gly Asn Glu Leu Ala Ser Ala Ala Ala Arg Gly Asp
145                 150                 155                 160

Leu Glu Gln Leu Thr Ser Leu Leu Gln Asn Asn Val Asn Val Asn Ala
                165                 170                 175

Gln Asn Gly Phe Gly Arg Thr Ala Leu Gln Val Met Lys Leu Gly Asn
            180                 185                 190
```

Pro Glu Ile Ala Arg Arg Leu Leu Leu Arg Gly Ala Asn Pro Asp Leu
195 200 205

Lys Asp Arg Thr Gly Asn Ala Val Ile His Asp Ala Ala Arg Ala Gly
210 215 220

Phe Leu Asp Thr Leu Gln Thr Leu Leu Glu Phe Gln Ala Asp Val Asn
225 230 235 240

Ile Glu Asp Asn Glu Gly Asn Leu Pro Leu His Leu Ala Ala Lys Glu
245 250 255

Gly His Leu Arg Val Val Glu Phe Leu Val Lys His Thr Ala Ser Asn
260 265 270

Val Gly His Arg Asn His Lys Gly Asp Thr Ala Cys Asp Leu Ala Arg
275 280 285

Leu Tyr Gly Arg Asn Glu Val Val Ser Leu Met Gln Ala Asn Gly Ala
290 295 300

Gly Gly Ala Thr Asn Leu Gln Gly Gly Lys Lys Lys Arg Lys Gly Gly
305 310 315 320

Gly Gly Gly Ser Asp Ile Cys Leu Pro Arg Trp Gly Cys Leu Trp Glu
325 330 335

Asp

<210> SEQ ID NO 57
<211> LENGTH: 319
<212> TYPE: PRT
<213> ORGANISM: Artificial Sequence
<220> FEATURE:
<223> OTHER INFORMATION: Synthetic

<400> SEQUENCE: 57

Met Arg Gly Ser His His His His His His Asp Tyr Asp Ile Pro Thr
1 5 10 15

Thr Glu Asn Leu Tyr Phe Gln Gly Ser Gly Gly Gly Gly Met Gln Ile
20 25 30

Phe Val Arg Thr Leu Thr Gly Arg Thr Ile Thr Leu Glu Val Glu Pro
35 40 45

Ser Asp Thr Ile Glu Asn Val Arg Ala Arg Ile Gln Asp Arg Glu Gly
50 55 60

Ile Pro Pro Asp Gln Gln Arg Leu Ile Phe Ala Gly Arg Gln Leu Glu
65 70 75 80

Asp Gly Arg Thr Leu Ser Asp Tyr Asn Ile Gln Arg Glu Ser Thr Leu
85 90 95

His Leu Val Leu Arg Leu Arg Gly Ala Gly Gly Glu Thr Phe Ser Asp
100 105 110

Leu Trp Lys Leu Leu Pro Glu Asn Gly Gly Gly Gly Gly Met Ala Glu
115 120 125

Pro Trp Gly Asn Glu Leu Ala Ser Ala Ala Ala Arg Gly Asp Leu Glu
130 135 140

Gln Leu Thr Ser Leu Leu Gln Asn Asn Val Asn Val Asn Ala Gln Asn
145 150 155 160

Gly Phe Gly Arg Thr Ala Leu Gln Val Met Lys Leu Gly Asn Pro Glu
165 170 175

Ile Ala Arg Arg Leu Leu Leu Arg Gly Ala Asn Pro Asp Leu Lys Asp
180 185 190

Arg Thr Gly Asn Ala Val Ile His Asp Ala Ala Arg Ala Gly Phe Leu
195 200 205

```
Asp Thr Leu Gln Thr Leu Leu Glu Phe Gln Ala Asp Val Asn Ile Glu
    210                 215                 220

Asp Asn Glu Gly Asn Leu Pro Leu His Leu Ala Ala Lys Glu Gly His
225                 230                 235                 240

Leu Arg Val Val Glu Phe Leu Val Lys His Thr Ala Ser Asn Val Gly
                245                 250                 255

His Arg Asn His Lys Gly Asp Thr Ala Cys Asp Leu Ala Arg Leu Tyr
            260                 265                 270

Gly Arg Asn Glu Val Val Ser Leu Met Gln Ala Asn Gly Ala Gly Gly
        275                 280                 285

Ala Thr Asn Leu Gln Gly Gly Lys Lys Lys Arg Lys Gly Gly Gly Gly
    290                 295                 300

Gly Ser Asp Ile Cys Leu Pro Arg Trp Gly Cys Leu Trp Glu Asp
305                 310                 315


<210> SEQ ID NO 58
<211> LENGTH: 164
<212> TYPE: PRT
<213> ORGANISM: Artificial Sequence
<220> FEATURE:
<223> OTHER INFORMATION: Synthetic

<400> SEQUENCE: 58

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Ala Ala Val Ala Leu
            100                 105                 110

Leu Pro Ala Val Leu Leu Ala Leu Leu Ala Pro Gly Gly Glu Thr Phe
        115                 120                 125

Ser Asp Leu Trp Lys Leu Leu Pro Glu Asn Gly Gly Lys Lys Lys Arg
    130                 135                 140

Lys Gly Gly Gly Gly Gly Ser Asp Ile Cys Leu Pro Arg Trp Gly Cys
145                 150                 155                 160

Leu Trp Glu Asp


<210> SEQ ID NO 59
<211> LENGTH: 146
<212> TYPE: PRT
<213> ORGANISM: Artificial Sequence
<220> FEATURE:
<223> OTHER INFORMATION: Synthetic

<400> SEQUENCE: 59

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30
```

```
Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Glu Thr Phe Ser Asp
            100                 105                 110

Leu Trp Lys Leu Leu Pro Glu Asn Gly Gly Lys Lys Lys Arg Lys Gly
        115                 120                 125

Gly Gly Gly Gly Ser Asp Ile Cys Leu Pro Arg Trp Gly Cys Leu Trp
    130                 135                 140

Glu Asp
145


<210> SEQ ID NO 60
<211> LENGTH: 319
<212> TYPE: PRT
<213> ORGANISM: Artificial Sequence
<220> FEATURE:
<223> OTHER INFORMATION: Synthetic

<400> SEQUENCE: 60

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Ala Ala Val Ala Leu
            100                 105                 110

Leu Pro Ala Val Leu Leu Ala Leu Leu Ala Pro Gly Gly Met Ala Glu
        115                 120                 125

Pro Trp Gly Asn Glu Leu Ala Ser Ala Ala Ala Arg Gly Asp Leu Glu
    130                 135                 140

Gln Leu Thr Ser Leu Leu Gln Asn Asn Val Asn Val Asn Ala Gln Asn
145                 150                 155                 160

Gly Phe Gly Arg Thr Ala Leu Gln Val Met Lys Leu Gly Asn Pro Glu
                165                 170                 175

Ile Ala Arg Arg Leu Leu Leu Arg Gly Ala Asn Pro Asp Leu Lys Asp
            180                 185                 190

Arg Thr Gly Asn Ala Val Ile His Asp Ala Ala Arg Ala Gly Phe Leu
        195                 200                 205

Asp Thr Leu Gln Thr Leu Leu Glu Phe Gln Ala Asp Val Asn Ile Glu
    210                 215                 220

Asp Asn Glu Gly Asn Leu Pro Leu His Leu Ala Ala Lys Glu Gly His
225                 230                 235                 240
```

```
Leu Arg Val Val Glu Phe Leu Val Lys His Thr Ala Ser Asn Val Gly
                245                 250                 255

His Arg Asn His Lys Gly Asp Thr Ala Cys Asp Leu Ala Arg Leu Tyr
            260                 265                 270

Gly Arg Asn Glu Val Val Ser Leu Met Gln Ala Asn Gly Ala Gly Gly
        275                 280                 285

Ala Thr Asn Leu Gln Gly Gly Lys Lys Lys Arg Lys Gly Gly Gly Gly
    290                 295                 300

Gly Ser Asp Ile Cys Leu Pro Arg Trp Gly Cys Leu Trp Glu Asp
305                 310                 315


<210> SEQ ID NO 61
<211> LENGTH: 301
<212> TYPE: PRT
<213> ORGANISM: Artificial Sequence
<220> FEATURE:
<223> OTHER INFORMATION: Synthetic

<400> SEQUENCE: 61

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Met Ala Glu Pro Trp
            100                 105                 110

Gly Asn Glu Leu Ala Ser Ala Ala Ala Arg Gly Asp Leu Glu Gln Leu
        115                 120                 125

Thr Ser Leu Leu Gln Asn Asn Val Asn Val Asn Ala Gln Asn Gly Phe
    130                 135                 140

Gly Arg Thr Ala Leu Gln Val Met Lys Leu Gly Asn Pro Glu Ile Ala
145                 150                 155                 160

Arg Arg Leu Leu Leu Arg Gly Ala Asn Pro Asp Leu Lys Asp Arg Thr
                165                 170                 175

Gly Asn Ala Val Ile His Asp Ala Ala Arg Ala Gly Phe Leu Asp Thr
            180                 185                 190

Leu Gln Thr Leu Leu Glu Phe Gln Ala Asp Val Asn Ile Glu Asp Asn
        195                 200                 205

Glu Gly Asn Leu Pro Leu His Leu Ala Ala Lys Glu Gly His Leu Arg
    210                 215                 220

Val Val Glu Phe Leu Val Lys His Thr Ala Ser Asn Val Gly His Arg
225                 230                 235                 240

Asn His Lys Gly Asp Thr Ala Cys Asp Leu Ala Arg Leu Tyr Gly Arg
                245                 250                 255

Asn Glu Val Val Ser Leu Met Gln Ala Asn Gly Ala Gly Gly Ala Thr
            260                 265                 270

Asn Leu Gln Gly Gly Lys Lys Lys Arg Lys Gly Gly Gly Gly Gly Ser
        275                 280                 285
```

```
Asp Ile Cys Leu Pro Arg Trp Gly Cys Leu Trp Glu Asp
    290                 295                 300
```

<210> SEQ ID NO 62
<211> LENGTH: 336
<212> TYPE: PRT
<213> ORGANISM: Artificial Sequence
<220> FEATURE:
<223> OTHER INFORMATION: Synthetic

<400> SEQUENCE: 62

```
Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Ala Ala Val Ala Leu
            100                 105                 110

Leu Pro Ala Val Leu Leu Ala Leu Leu Ala Pro Gly Gly Glu Thr Phe
        115                 120                 125

Glu His Trp Trp Ser Gln Leu Leu Ser Gly Gly Gly Gly Gly Met Ala
    130                 135                 140

Glu Pro Trp Gly Asn Glu Leu Ala Ser Ala Ala Ala Arg Gly Asp Leu
145                 150                 155                 160

Glu Gln Leu Thr Ser Leu Leu Gln Asn Asn Val Asn Val Asn Ala Gln
                165                 170                 175

Asn Gly Phe Gly Arg Thr Ala Leu Gln Val Met Lys Leu Gly Asn Pro
            180                 185                 190

Glu Ile Ala Arg Arg Leu Leu Leu Arg Gly Ala Asn Pro Asp Leu Lys
        195                 200                 205

Asp Arg Thr Gly Asn Ala Val Ile His Asp Ala Ala Arg Ala Gly Phe
    210                 215                 220

Leu Asp Thr Leu Gln Thr Leu Leu Glu Phe Gln Ala Asp Val Asn Ile
225                 230                 235                 240

Glu Asp Asn Glu Gly Asn Leu Pro Leu His Leu Ala Ala Lys Glu Gly
                245                 250                 255

His Leu Arg Val Val Glu Phe Leu Val Lys His Thr Ala Ser Asn Val
            260                 265                 270

Gly His Arg Asn His Lys Gly Asp Thr Ala Cys Asp Leu Ala Arg Leu
        275                 280                 285

Tyr Gly Arg Asn Glu Val Val Ser Leu Met Gln Ala Asn Gly Ala Gly
    290                 295                 300

Gly Ala Thr Asn Leu Gln Gly Gly Lys Lys Lys Arg Lys Gly Gly Gly
305                 310                 315                 320

Gly Gly Ser Asp Ile Cys Leu Pro Arg Trp Gly Cys Leu Trp Glu Asp
                325                 330                 335
```

<210> SEQ ID NO 63
<211> LENGTH: 163

<212> TYPE: PRT
<213> ORGANISM: Artificial Sequence
<220> FEATURE:
<223> OTHER INFORMATION: Synthetic

<400> SEQUENCE: 63

```
Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Ala Ala Val Ala Leu
            100                 105                 110

Leu Pro Ala Val Leu Leu Ala Leu Leu Ala Pro Gly Gly Glu Thr Phe
        115                 120                 125

Glu His Trp Trp Ser Gln Leu Leu Ser Gly Gly Lys Lys Lys Arg Lys
    130                 135                 140

Gly Gly Gly Gly Gly Ser Asp Ile Cys Leu Pro Arg Trp Gly Cys Leu
145                 150                 155                 160

Trp Glu Asp
```

<210> SEQ ID NO 64
<211> LENGTH: 336
<212> TYPE: PRT
<213> ORGANISM: Artificial Sequence
<220> FEATURE:
<223> OTHER INFORMATION: Synthetic

<400> SEQUENCE: 64

```
Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Ala Ala Val Ala Leu
            100                 105                 110

Leu Pro Ala Val Leu Leu Ala Leu Leu Ala Pro Gly Gly Thr Ser Phe
        115                 120                 125

Ala Glu Tyr Trp Asn Leu Leu Ser Pro Gly Gly Gly Gly Gly Met Ala
    130                 135                 140

Glu Pro Trp Gly Asn Glu Leu Ala Ser Ala Ala Ala Arg Gly Asp Leu
145                 150                 155                 160
```

```
Glu Gln Leu Thr Ser Leu Leu Gln Asn Asn Val Asn Val Asn Ala Gln
                165                 170                 175

Asn Gly Phe Gly Arg Thr Ala Leu Gln Val Met Lys Leu Gly Asn Pro
            180                 185                 190

Glu Ile Ala Arg Arg Leu Leu Leu Arg Gly Ala Asn Pro Asp Leu Lys
        195                 200                 205

Asp Arg Thr Gly Asn Ala Val Ile His Asp Ala Ala Arg Ala Gly Phe
    210                 215                 220

Leu Asp Thr Leu Gln Thr Leu Leu Glu Phe Gln Ala Asp Val Asn Ile
225                 230                 235                 240

Glu Asp Asn Glu Gly Asn Leu Pro Leu His Leu Ala Ala Lys Glu Gly
                245                 250                 255

His Leu Arg Val Val Glu Phe Leu Val Lys His Thr Ala Ser Asn Val
            260                 265                 270

Gly His Arg Asn His Lys Gly Asp Thr Ala Cys Asp Leu Ala Arg Leu
        275                 280                 285

Tyr Gly Arg Asn Glu Val Val Ser Leu Met Gln Ala Asn Gly Ala Gly
    290                 295                 300

Gly Ala Thr Asn Leu Gln Gly Gly Lys Lys Lys Arg Lys Gly Gly Gly
305                 310                 315                 320

Gly Gly Ser Asp Ile Cys Leu Pro Arg Trp Gly Cys Leu Trp Glu Asp
                325                 330                 335


<210> SEQ ID NO 65
<211> LENGTH: 163
<212> TYPE: PRT
<213> ORGANISM: Artificial Sequence
<220> FEATURE:
<223> OTHER INFORMATION: Synthetic

<400> SEQUENCE: 65

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Ala Ala Val Ala Leu
            100                 105                 110

Leu Pro Ala Val Leu Leu Ala Leu Leu Ala Pro Gly Gly Thr Ser Phe
        115                 120                 125

Ala Glu Tyr Trp Asn Leu Leu Ser Pro Gly Gly Lys Lys Lys Arg Lys
    130                 135                 140

Gly Gly Gly Gly Gly Ser Asp Ile Cys Leu Pro Arg Trp Gly Cys Leu
145                 150                 155                 160

Trp Glu Asp


<210> SEQ ID NO 66
<211> LENGTH: 336
<212> TYPE: PRT
```

<213> ORGANISM: Artificial Sequence
<220> FEATURE:
<223> OTHER INFORMATION: Synthetic

<400> SEQUENCE: 66

```
Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Ala Ala Val Ala Leu
            100                 105                 110

Leu Pro Ala Val Leu Leu Ala Leu Leu Ala Pro Gly Gly Glu Thr Phe
        115                 120                 125

Glu His Trp Trp Asn Leu Leu Ser Pro Gly Gly Gly Gly Gly Met Ala
    130                 135                 140

Glu Pro Trp Gly Asn Glu Leu Ala Ser Ala Ala Ala Arg Gly Asp Leu
145                 150                 155                 160

Glu Gln Leu Thr Ser Leu Leu Gln Asn Asn Val Asn Val Asn Ala Gln
                165                 170                 175

Asn Gly Phe Gly Arg Thr Ala Leu Gln Val Met Lys Leu Gly Asn Pro
            180                 185                 190

Glu Ile Ala Arg Arg Leu Leu Leu Arg Gly Ala Asn Pro Asp Leu Lys
        195                 200                 205

Asp Arg Thr Gly Asn Ala Val Ile His Asp Ala Ala Arg Ala Gly Phe
    210                 215                 220

Leu Asp Thr Leu Gln Thr Leu Leu Glu Phe Gln Ala Asp Val Asn Ile
225                 230                 235                 240

Glu Asp Asn Glu Gly Asn Leu Pro Leu His Leu Ala Ala Lys Glu Gly
                245                 250                 255

His Leu Arg Val Val Glu Phe Leu Val Lys His Thr Ala Ser Asn Val
            260                 265                 270

Gly His Arg Asn His Lys Gly Asp Thr Ala Cys Asp Leu Ala Arg Leu
        275                 280                 285

Tyr Gly Arg Asn Glu Val Val Ser Leu Met Gln Ala Asn Gly Ala Gly
    290                 295                 300

Gly Ala Thr Asn Leu Gln Gly Gly Lys Lys Lys Arg Lys Gly Gly Gly
305                 310                 315                 320

Gly Gly Ser Asp Ile Cys Leu Pro Arg Trp Gly Cys Leu Trp Glu Asp
                325                 330                 335
```

<210> SEQ ID NO 67
<211> LENGTH: 163
<212> TYPE: PRT
<213> ORGANISM: Artificial Sequence
<220> FEATURE:
<223> OTHER INFORMATION: Synthetic

<400> SEQUENCE: 67

```
Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Ala Ala Val Ala Leu
            100                 105                 110

Leu Pro Ala Val Leu Leu Ala Leu Leu Ala Pro Gly Gly Glu Thr Phe
        115                 120                 125

Glu His Trp Trp Asn Leu Leu Ser Pro Gly Gly Lys Lys Lys Arg Lys
    130                 135                 140

Gly Gly Gly Gly Gly Ser Asp Ile Cys Leu Pro Arg Trp Gly Cys Leu
145                 150                 155                 160

Trp Glu Asp


<210> SEQ ID NO 68
<211> LENGTH: 534
<212> TYPE: PRT
<213> ORGANISM: Artificial Sequence
<220> FEATURE:
<223> OTHER INFORMATION: Synthetic

<400> SEQUENCE: 68

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Gly Gly Gly Met Glu
            100                 105                 110

Asp Pro Gln Gly Asp Ala Ala Gln Lys Thr Asp Thr Ser His His Asp
        115                 120                 125

Gln Asp His Pro Thr Phe Asn Lys Ile Thr Pro Asn Leu Ala Glu Phe
    130                 135                 140

Ala Phe Ser Leu Tyr Arg Gln Leu Ala His Gln Ser Asn Ser Thr Asn
145                 150                 155                 160

Ile Phe Phe Ser Pro Val Ser Ile Ala Thr Ala Phe Ala Met Leu Ser
                165                 170                 175

Leu Gly Thr Lys Ala Asp Thr His Asp Glu Ile Leu Glu Gly Leu Asn
            180                 185                 190

Phe Asn Leu Thr Glu Ile Pro Glu Ala Gln Ile His Glu Gly Phe Gln
```

```
        195                 200                 205

Glu Leu Leu Arg Thr Leu Asn Gln Pro Asp Ser Gln Leu Gln Leu Thr
    210                 215                 220

Thr Gly Asn Phe Leu Phe Leu Ser Glu Gly Leu Lys Leu Val Asp Lys
225                 230                 235                 240

Phe Leu Glu Asp Val Lys Lys Leu Tyr His Ser Glu Ala Phe Thr Val
                245                 250                 255

Asn Phe Gly Asp Thr Glu Glu Ala Lys Lys Gln Ile Asn Asp Tyr Val
            260                 265                 270

Glu Lys Gly Thr Gln Gly Lys Ile Val Asp Leu Val Lys Glu Leu Asp
        275                 280                 285

Arg Asp Thr Val Phe Ala Leu Val Asn Tyr Ile Phe Phe Lys Gly Lys
    290                 295                 300

Trp Glu Arg Pro Phe Glu Val Lys Asp Thr Glu Glu Glu Asp Phe His
305                 310                 315                 320

Val Asp Gln Val Thr Thr Val Lys Val Pro Met Met Lys Arg Leu Gly
                325                 330                 335

Met Phe Asn Ile Gln His Cys Lys Lys Leu Ser Ser Trp Val Leu Leu
            340                 345                 350

Met Lys Tyr Leu Gly Asn Ala Thr Ala Ile Phe Phe Leu Pro Asp Glu
        355                 360                 365

Gly Lys Leu Gln His Leu Glu Asn Glu Leu Thr His Asp Ile Ile Thr
    370                 375                 380

Lys Phe Leu Glu Asn Glu Asp Arg Arg Ser Ala Ser Leu His Leu Pro
385                 390                 395                 400

Lys Leu Ser Ile Thr Gly Thr Tyr Asp Leu Lys Ser Val Leu Gly Gln
                405                 410                 415

Leu Gly Ile Thr Lys Val Phe Ser Asn Gly Ala Asp Leu Ser Gly Val
            420                 425                 430

Thr Glu Glu Ala Pro Leu Lys Leu Ser Lys Ala Val His Lys Ala Val
        435                 440                 445

Leu Thr Ile Asp Glu Lys Gly Thr Glu Ala Ala Gly Ala Met Phe Leu
    450                 455                 460

Glu Ala Ile Pro Met Ser Ile Pro Pro Glu Val Lys Phe Asn Lys Pro
465                 470                 475                 480

Phe Val Phe Leu Met Ile Glu Gln Asn Thr Lys Ser Pro Leu Phe Met
                485                 490                 495

Gly Lys Val Val Asn Pro Thr Gln Lys Lys Asp Glu Leu Gly Gly Ala
            500                 505                 510

Ala Val Ala Leu Leu Pro Ala Val Leu Leu Ala Leu Leu Ala Pro Gly
        515                 520                 525

Gly Lys Lys Lys Arg Lys
    530


<210> SEQ ID NO 69
<211> LENGTH: 516
<212> TYPE: PRT
<213> ORGANISM: Artificial Sequence
<220> FEATURE:
<223> OTHER INFORMATION: Synthetic

<400> SEQUENCE: 69

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
```

```
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Gly Gly Gly Met Glu
            100                 105                 110

Asp Pro Gln Gly Asp Ala Ala Gln Lys Thr Asp Thr Ser His His Asp
        115                 120                 125

Gln Asp His Pro Thr Phe Asn Lys Ile Thr Pro Asn Leu Ala Glu Phe
    130                 135                 140

Ala Phe Ser Leu Tyr Arg Gln Leu Ala His Gln Ser Asn Ser Thr Asn
145                 150                 155                 160

Ile Phe Phe Ser Pro Val Ser Ile Ala Thr Ala Phe Ala Met Leu Ser
                165                 170                 175

Leu Gly Thr Lys Ala Asp Thr His Asp Glu Ile Leu Glu Gly Leu Asn
            180                 185                 190

Phe Asn Leu Thr Glu Ile Pro Glu Ala Gln Ile His Glu Gly Phe Gln
        195                 200                 205

Glu Leu Leu Arg Thr Leu Asn Gln Pro Asp Ser Gln Leu Gln Leu Thr
    210                 215                 220

Thr Gly Asn Phe Leu Phe Leu Ser Glu Gly Leu Lys Leu Val Asp Lys
225                 230                 235                 240

Phe Leu Glu Asp Val Lys Lys Leu Tyr His Ser Glu Ala Phe Thr Val
                245                 250                 255

Asn Phe Gly Asp Thr Glu Glu Ala Lys Lys Gln Ile Asn Asp Tyr Val
            260                 265                 270

Glu Lys Gly Thr Gln Gly Lys Ile Val Asp Leu Val Lys Glu Leu Asp
        275                 280                 285

Arg Asp Thr Val Phe Ala Leu Val Asn Tyr Ile Phe Phe Lys Gly Lys
    290                 295                 300

Trp Glu Arg Pro Phe Glu Val Lys Asp Thr Glu Glu Glu Asp Phe His
305                 310                 315                 320

Val Asp Gln Val Thr Thr Val Lys Val Pro Met Met Lys Arg Leu Gly
                325                 330                 335

Met Phe Asn Ile Gln His Cys Lys Lys Leu Ser Ser Trp Val Leu Leu
            340                 345                 350

Met Lys Tyr Leu Gly Asn Ala Thr Ala Ile Phe Phe Leu Pro Asp Glu
        355                 360                 365

Gly Lys Leu Gln His Leu Glu Asn Glu Leu Thr His Asp Ile Ile Thr
    370                 375                 380

Lys Phe Leu Glu Asn Glu Asp Arg Arg Ser Ala Ser Leu His Leu Pro
385                 390                 395                 400

Lys Leu Ser Ile Thr Gly Thr Tyr Asp Leu Lys Ser Val Leu Gly Gln
                405                 410                 415

Leu Gly Ile Thr Lys Val Phe Ser Asn Gly Ala Asp Leu Ser Gly Val
            420                 425                 430

Thr Glu Glu Ala Pro Leu Lys Leu Ser Lys Ala Val His Lys Ala Val
        435                 440                 445
```

```
Leu Thr Ile Asp Glu Lys Gly Thr Glu Ala Ala Gly Ala Met Phe Leu
    450                 455                 460

Glu Ala Ile Pro Met Ser Ile Pro Pro Glu Val Lys Phe Asn Lys Pro
465                 470                 475                 480

Phe Val Phe Leu Met Ile Glu Gln Asn Thr Lys Ser Pro Leu Phe Met
                485                 490                 495

Gly Lys Val Val Asn Pro Thr Gln Lys Lys Asp Glu Leu Gly Gly Lys
            500                 505                 510

Lys Lys Arg Lys
        515


<210> SEQ ID NO 70
<211> LENGTH: 549
<212> TYPE: PRT
<213> ORGANISM: Artificial Sequence
<220> FEATURE:
<223> OTHER INFORMATION: Synthetic

<400> SEQUENCE: 70

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Glu Thr Phe Ser Asp
            100                 105                 110

Leu Trp Lys Leu Leu Pro Glu Asn Gly Gly Gly Gly Gly Met Glu Asp
        115                 120                 125

Pro Gln Gly Asp Ala Ala Gln Lys Thr Asp Thr Ser His His Asp Gln
    130                 135                 140

Asp His Pro Thr Phe Asn Lys Ile Thr Pro Asn Leu Ala Glu Phe Ala
145                 150                 155                 160

Phe Ser Leu Tyr Arg Gln Leu Ala His Gln Ser Asn Ser Thr Asn Ile
                165                 170                 175

Phe Phe Ser Pro Val Ser Ile Ala Thr Ala Phe Ala Met Leu Ser Leu
            180                 185                 190

Gly Thr Lys Ala Asp Thr His Asp Glu Ile Leu Glu Gly Leu Asn Phe
        195                 200                 205

Asn Leu Thr Glu Ile Pro Glu Ala Gln Ile His Glu Gly Phe Gln Glu
    210                 215                 220

Leu Leu Arg Thr Leu Asn Gln Pro Asp Ser Gln Leu Gln Leu Thr Thr
225                 230                 235                 240

Gly Asn Phe Leu Phe Leu Ser Glu Gly Leu Lys Leu Val Asp Lys Phe
                245                 250                 255

Leu Glu Asp Val Lys Lys Leu Tyr His Ser Glu Ala Phe Thr Val Asn
            260                 265                 270

Phe Gly Asp Thr Glu Glu Ala Lys Lys Gln Ile Asn Asp Tyr Val Glu
        275                 280                 285
```

```
Lys Gly Thr Gln Gly Lys Ile Val Asp Leu Val Lys Glu Leu Asp Arg
    290                 295                 300

Asp Thr Val Phe Ala Leu Val Asn Tyr Ile Phe Phe Lys Gly Lys Trp
305                 310                 315                 320

Glu Arg Pro Phe Glu Val Lys Asp Thr Glu Glu Glu Asp Phe His Val
                325                 330                 335

Asp Gln Val Thr Thr Val Lys Val Pro Met Met Lys Arg Leu Gly Met
            340                 345                 350

Phe Asn Ile Gln His Cys Lys Lys Leu Ser Ser Trp Val Leu Leu Met
        355                 360                 365

Lys Tyr Leu Gly Asn Ala Thr Ala Ile Phe Phe Leu Pro Asp Glu Gly
    370                 375                 380

Lys Leu Gln His Leu Glu Asn Glu Leu Thr His Asp Ile Ile Thr Lys
385                 390                 395                 400

Phe Leu Glu Asn Glu Asp Arg Arg Ser Ala Ser Leu His Leu Pro Lys
                405                 410                 415

Leu Ser Ile Thr Gly Thr Tyr Asp Leu Lys Ser Val Leu Gly Gln Leu
            420                 425                 430

Gly Ile Thr Lys Val Phe Ser Asn Gly Ala Asp Leu Ser Gly Val Thr
        435                 440                 445

Glu Glu Ala Pro Leu Lys Leu Ser Lys Ala Val His Lys Ala Val Leu
    450                 455                 460

Thr Ile Asp Glu Lys Gly Thr Glu Ala Ala Gly Ala Met Phe Leu Glu
465                 470                 475                 480

Ala Ile Pro Met Ser Ile Pro Pro Glu Val Lys Phe Asn Lys Pro Phe
                485                 490                 495

Val Phe Leu Met Ile Glu Gln Asn Thr Lys Ser Pro Leu Phe Met Gly
            500                 505                 510

Lys Val Val Asn Pro Thr Gln Lys Lys Asp Glu Leu Gly Gly Ala Ala
        515                 520                 525

Val Ala Leu Leu Pro Ala Val Leu Leu Ala Leu Leu Ala Pro Gly Gly
    530                 535                 540

Lys Lys Lys Arg Lys
545


<210> SEQ ID NO 71
<211> LENGTH: 531
<212> TYPE: PRT
<213> ORGANISM: Artificial Sequence
<220> FEATURE:
<223> OTHER INFORMATION: Synthetic

<400> SEQUENCE: 71

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95
```

```
His Leu Val Leu Arg Leu Arg Gly Ala Gly Gly Glu Thr Phe Ser Asp
            100                 105                 110

Leu Trp Lys Leu Leu Pro Glu Asn Gly Gly Gly Gly Gly Met Glu Asp
        115                 120                 125

Pro Gln Gly Asp Ala Ala Gln Lys Thr Asp Thr Ser His His Asp Gln
    130                 135                 140

Asp His Pro Thr Phe Asn Lys Ile Thr Pro Asn Leu Ala Glu Phe Ala
145                 150                 155                 160

Phe Ser Leu Tyr Arg Gln Leu Ala His Gln Ser Asn Ser Thr Asn Ile
                165                 170                 175

Phe Phe Ser Pro Val Ser Ile Ala Thr Ala Phe Ala Met Leu Ser Leu
            180                 185                 190

Gly Thr Lys Ala Asp Thr His Asp Glu Ile Leu Glu Gly Leu Asn Phe
        195                 200                 205

Asn Leu Thr Glu Ile Pro Glu Ala Gln Ile His Glu Gly Phe Gln Glu
    210                 215                 220

Leu Leu Arg Thr Leu Asn Gln Pro Asp Ser Gln Leu Gln Leu Thr Thr
225                 230                 235                 240

Gly Asn Phe Leu Phe Leu Ser Glu Gly Leu Lys Leu Val Asp Lys Phe
                245                 250                 255

Leu Glu Asp Val Lys Lys Leu Tyr His Ser Glu Ala Phe Thr Val Asn
            260                 265                 270

Phe Gly Asp Thr Glu Glu Ala Lys Lys Gln Ile Asn Asp Tyr Val Glu
        275                 280                 285

Lys Gly Thr Gln Gly Lys Ile Val Asp Leu Val Lys Glu Leu Asp Arg
    290                 295                 300

Asp Thr Val Phe Ala Leu Val Asn Tyr Ile Phe Phe Lys Gly Lys Trp
305                 310                 315                 320

Glu Arg Pro Phe Glu Val Lys Asp Thr Glu Glu Glu Asp Phe His Val
                325                 330                 335

Asp Gln Val Thr Thr Val Lys Val Pro Met Met Lys Arg Leu Gly Met
            340                 345                 350

Phe Asn Ile Gln His Cys Lys Lys Leu Ser Ser Trp Val Leu Leu Met
        355                 360                 365

Lys Tyr Leu Gly Asn Ala Thr Ala Ile Phe Phe Leu Pro Asp Glu Gly
    370                 375                 380

Lys Leu Gln His Leu Glu Asn Glu Leu Thr His Asp Ile Ile Thr Lys
385                 390                 395                 400

Phe Leu Glu Asn Glu Asp Arg Arg Ser Ala Ser Leu His Leu Pro Lys
                405                 410                 415

Leu Ser Ile Thr Gly Thr Tyr Asp Leu Lys Ser Val Leu Gly Gln Leu
            420                 425                 430

Gly Ile Thr Lys Val Phe Ser Asn Gly Ala Asp Leu Ser Gly Val Thr
        435                 440                 445

Glu Glu Ala Pro Leu Lys Leu Ser Lys Ala Val His Lys Ala Val Leu
    450                 455                 460

Thr Ile Asp Glu Lys Gly Thr Glu Ala Ala Gly Ala Met Phe Leu Glu
465                 470                 475                 480

Ala Ile Pro Met Ser Ile Pro Pro Glu Val Lys Phe Asn Lys Pro Phe
                485                 490                 495

Val Phe Leu Met Ile Glu Gln Asn Thr Lys Ser Pro Leu Phe Met Gly
            500                 505                 510
```

```
Lys Val Val Asn Pro Thr Gln Lys Lys Asp Glu Leu Gly Gly Lys Lys
        515                 520                 525

Lys Arg Lys
    530


<210> SEQ ID NO 72
<211> LENGTH: 704
<212> TYPE: PRT
<213> ORGANISM: Artificial Sequence
<220> FEATURE:
<223> OTHER INFORMATION: Synthetic

<400> SEQUENCE: 72

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Met Ala Glu Pro Trp
            100                 105                 110

Gly Asn Glu Leu Ala Ser Ala Ala Ala Arg Gly Asp Leu Glu Gln Leu
        115                 120                 125

Thr Ser Leu Leu Gln Asn Asn Val Asn Val Asn Ala Gln Asn Gly Phe
    130                 135                 140

Gly Arg Thr Ala Leu Gln Val Met Lys Leu Gly Asn Pro Glu Ile Ala
145                 150                 155                 160

Arg Arg Leu Leu Leu Arg Gly Ala Asn Pro Asp Leu Lys Asp Arg Thr
                165                 170                 175

Gly Asn Ala Val Ile His Asp Ala Ala Arg Ala Gly Phe Leu Asp Thr
            180                 185                 190

Leu Gln Thr Leu Leu Glu Phe Gln Ala Asp Val Asn Ile Glu Asp Asn
        195                 200                 205

Glu Gly Asn Leu Pro Leu His Leu Ala Ala Lys Glu Gly His Leu Arg
    210                 215                 220

Val Val Glu Phe Leu Val Lys His Thr Ala Ser Asn Val Gly His Arg
225                 230                 235                 240

Asn His Lys Gly Asp Thr Ala Cys Asp Leu Ala Arg Leu Tyr Gly Arg
                245                 250                 255

Asn Glu Val Val Ser Leu Met Gln Ala Asn Gly Ala Gly Gly Ala Thr
            260                 265                 270

Asn Leu Gln Gly Gly Gly Gly Gly Met Glu Asp Pro Gln Gly Asp Ala
        275                 280                 285

Ala Gln Lys Thr Asp Thr Ser His His Asp Gln Asp His Pro Thr Phe
    290                 295                 300

Asn Lys Ile Thr Pro Asn Leu Ala Glu Phe Ala Phe Ser Leu Tyr Arg
305                 310                 315                 320

Gln Leu Ala His Gln Ser Asn Ser Thr Asn Ile Phe Phe Ser Pro Val
                325                 330                 335
```

```
Ser Ile Ala Thr Ala Phe Ala Met Leu Ser Leu Gly Thr Lys Ala Asp
            340                 345                 350

Thr His Asp Glu Ile Leu Glu Gly Leu Asn Phe Asn Leu Thr Glu Ile
        355                 360                 365

Pro Glu Ala Gln Ile His Glu Gly Phe Gln Glu Leu Leu Arg Thr Leu
    370                 375                 380

Asn Gln Pro Asp Ser Gln Leu Gln Leu Thr Thr Gly Asn Phe Leu Phe
385                 390                 395                 400

Leu Ser Glu Gly Leu Lys Leu Val Asp Lys Phe Leu Glu Asp Val Lys
                405                 410                 415

Lys Leu Tyr His Ser Glu Ala Phe Thr Val Asn Phe Gly Asp Thr Glu
            420                 425                 430

Glu Ala Lys Lys Gln Ile Asn Asp Tyr Val Glu Lys Gly Thr Gln Gly
        435                 440                 445

Lys Ile Val Asp Leu Val Lys Glu Leu Asp Arg Asp Thr Val Phe Ala
    450                 455                 460

Leu Val Asn Tyr Ile Phe Phe Lys Gly Lys Trp Glu Arg Pro Phe Glu
465                 470                 475                 480

Val Lys Asp Thr Glu Glu Glu Asp Phe His Val Asp Gln Val Thr Thr
                485                 490                 495

Val Lys Val Pro Met Met Lys Arg Leu Gly Met Phe Asn Ile Gln His
            500                 505                 510

Cys Lys Lys Leu Ser Ser Trp Val Leu Leu Met Lys Tyr Leu Gly Asn
        515                 520                 525

Ala Thr Ala Ile Phe Phe Leu Pro Asp Glu Gly Lys Leu Gln His Leu
    530                 535                 540

Glu Asn Glu Leu Thr His Asp Ile Ile Thr Lys Phe Leu Glu Asn Glu
545                 550                 555                 560

Asp Arg Arg Ser Ala Ser Leu His Leu Pro Lys Leu Ser Ile Thr Gly
                565                 570                 575

Thr Tyr Asp Leu Lys Ser Val Leu Gly Gln Leu Gly Ile Thr Lys Val
            580                 585                 590

Phe Ser Asn Gly Ala Asp Leu Ser Gly Val Thr Glu Glu Ala Pro Leu
        595                 600                 605

Lys Leu Ser Lys Ala Val His Lys Ala Val Leu Thr Ile Asp Glu Lys
    610                 615                 620

Gly Thr Glu Ala Ala Gly Ala Met Phe Leu Glu Ala Ile Pro Met Ser
625                 630                 635                 640

Ile Pro Pro Glu Val Lys Phe Asn Lys Pro Phe Val Phe Leu Met Ile
                645                 650                 655

Glu Gln Asn Thr Lys Ser Pro Leu Phe Met Gly Lys Val Val Asn Pro
            660                 665                 670

Thr Gln Lys Lys Asp Glu Leu Gly Gly Ala Ala Val Ala Leu Leu Pro
        675                 680                 685

Ala Val Leu Leu Ala Leu Leu Ala Pro Gly Gly Lys Lys Lys Arg Lys
    690                 695                 700
```

<210> SEQ ID NO 73
<211> LENGTH: 686
<212> TYPE: PRT
<213> ORGANISM: Artificial Sequence
<220> FEATURE:
<223> OTHER INFORMATION: Synthetic

<400> SEQUENCE: 73

-continued

```
Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Met Ala Glu Pro Trp
            100                 105                 110

Gly Asn Glu Leu Ala Ser Ala Ala Ala Arg Gly Asp Leu Glu Gln Leu
        115                 120                 125

Thr Ser Leu Leu Gln Asn Asn Val Asn Val Asn Ala Gln Asn Gly Phe
    130                 135                 140

Gly Arg Thr Ala Leu Gln Val Met Lys Leu Gly Asn Pro Glu Ile Ala
145                 150                 155                 160

Arg Arg Leu Leu Leu Arg Gly Ala Asn Pro Asp Leu Lys Asp Arg Thr
                165                 170                 175

Gly Asn Ala Val Ile His Asp Ala Ala Arg Ala Gly Phe Leu Asp Thr
            180                 185                 190

Leu Gln Thr Leu Leu Glu Phe Gln Ala Asp Val Asn Ile Glu Asp Asn
        195                 200                 205

Glu Gly Asn Leu Pro Leu His Leu Ala Ala Lys Glu Gly His Leu Arg
    210                 215                 220

Val Val Glu Phe Leu Val Lys His Thr Ala Ser Asn Val Gly His Arg
225                 230                 235                 240

Asn His Lys Gly Asp Thr Ala Cys Asp Leu Ala Arg Leu Tyr Gly Arg
                245                 250                 255

Asn Glu Val Val Ser Leu Met Gln Ala Asn Gly Ala Gly Gly Ala Thr
            260                 265                 270

Asn Leu Gln Gly Gly Gly Gly Gly Met Glu Asp Pro Gln Gly Asp Ala
        275                 280                 285

Ala Gln Lys Thr Asp Thr Ser His His Asp Gln Asp His Pro Thr Phe
    290                 295                 300

Asn Lys Ile Thr Pro Asn Leu Ala Glu Phe Ala Phe Ser Leu Tyr Arg
305                 310                 315                 320

Gln Leu Ala His Gln Ser Asn Ser Thr Asn Ile Phe Phe Ser Pro Val
                325                 330                 335

Ser Ile Ala Thr Ala Phe Ala Met Leu Ser Leu Gly Thr Lys Ala Asp
            340                 345                 350

Thr His Asp Glu Ile Leu Glu Gly Leu Asn Phe Asn Leu Thr Glu Ile
        355                 360                 365

Pro Glu Ala Gln Ile His Glu Gly Phe Gln Glu Leu Leu Arg Thr Leu
    370                 375                 380

Asn Gln Pro Asp Ser Gln Leu Gln Leu Thr Thr Gly Asn Phe Leu Phe
385                 390                 395                 400

Leu Ser Glu Gly Leu Lys Leu Val Asp Lys Phe Leu Glu Asp Val Lys
                405                 410                 415

Lys Leu Tyr His Ser Glu Ala Phe Thr Val Asn Phe Gly Asp Thr Glu
```

```
            420                 425                 430

Glu Ala Lys Lys Gln Ile Asn Asp Tyr Val Glu Lys Gly Thr Gln Gly
        435                 440                 445

Lys Ile Val Asp Leu Val Lys Glu Leu Asp Arg Asp Thr Val Phe Ala
    450                 455                 460

Leu Val Asn Tyr Ile Phe Phe Lys Gly Lys Trp Glu Arg Pro Phe Glu
465                 470                 475                 480

Val Lys Asp Thr Glu Glu Glu Asp Phe His Val Asp Gln Val Thr Thr
                485                 490                 495

Val Lys Val Pro Met Met Lys Arg Leu Gly Met Phe Asn Ile Gln His
            500                 505                 510

Cys Lys Lys Leu Ser Ser Trp Val Leu Leu Met Lys Tyr Leu Gly Asn
        515                 520                 525

Ala Thr Ala Ile Phe Phe Leu Pro Asp Glu Gly Lys Leu Gln His Leu
    530                 535                 540

Glu Asn Glu Leu Thr His Asp Ile Ile Thr Lys Phe Leu Glu Asn Glu
545                 550                 555                 560

Asp Arg Arg Ser Ala Ser Leu His Leu Pro Lys Leu Ser Ile Thr Gly
                565                 570                 575

Thr Tyr Asp Leu Lys Ser Val Leu Gly Gln Leu Gly Ile Thr Lys Val
            580                 585                 590

Phe Ser Asn Gly Ala Asp Leu Ser Gly Val Thr Glu Glu Ala Pro Leu
        595                 600                 605

Lys Leu Ser Lys Ala Val His Lys Ala Val Leu Thr Ile Asp Glu Lys
    610                 615                 620

Gly Thr Glu Ala Ala Gly Ala Met Phe Leu Glu Ala Ile Pro Met Ser
625                 630                 635                 640

Ile Pro Pro Glu Val Lys Phe Asn Lys Pro Phe Val Phe Leu Met Ile
                645                 650                 655

Glu Gln Asn Thr Lys Ser Pro Leu Phe Met Gly Lys Val Val Asn Pro
            660                 665                 670

Thr Gln Lys Lys Asp Glu Leu Gly Gly Lys Lys Lys Arg Lys
        675                 680                 685


<210> SEQ ID NO 74
<211> LENGTH: 719
<212> TYPE: PRT
<213> ORGANISM: Artificial Sequence
<220> FEATURE:
<223> OTHER INFORMATION: Synthetic

<400> SEQUENCE: 74

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Glu Thr Phe Ser Asp
```

-continued

```
            100                 105                 110

Leu Trp Lys Leu Leu Pro Glu Asn Gly Gly Gly Gly Gly Met Ala Glu
        115                 120                 125

Pro Trp Gly Asn Glu Leu Ala Ser Ala Ala Ala Arg Gly Asp Leu Glu
    130                 135                 140

Gln Leu Thr Ser Leu Leu Gln Asn Asn Val Asn Val Asn Ala Gln Asn
145                 150                 155                 160

Gly Phe Gly Arg Thr Ala Leu Gln Val Met Lys Leu Gly Asn Pro Glu
                165                 170                 175

Ile Ala Arg Arg Leu Leu Leu Arg Gly Ala Asn Pro Asp Leu Lys Asp
            180                 185                 190

Arg Thr Gly Asn Ala Val Ile His Asp Ala Ala Arg Ala Gly Phe Leu
        195                 200                 205

Asp Thr Leu Gln Thr Leu Leu Glu Phe Gln Ala Asp Val Asn Ile Glu
    210                 215                 220

Asp Asn Glu Gly Asn Leu Pro Leu His Leu Ala Ala Lys Glu Gly His
225                 230                 235                 240

Leu Arg Val Val Glu Phe Leu Val Lys His Thr Ala Ser Asn Val Gly
                245                 250                 255

His Arg Asn His Lys Gly Asp Thr Ala Cys Asp Leu Ala Arg Leu Tyr
            260                 265                 270

Gly Arg Asn Glu Val Val Ser Leu Met Gln Ala Asn Gly Ala Gly Gly
        275                 280                 285

Ala Thr Asn Leu Gln Gly Gly Met Glu Asp Pro Gln Gly Asp Ala Ala
    290                 295                 300

Gln Lys Thr Asp Thr Ser His His Asp Gln Asp His Pro Thr Phe Asn
305                 310                 315                 320

Lys Ile Thr Pro Asn Leu Ala Glu Phe Ala Phe Ser Leu Tyr Arg Gln
                325                 330                 335

Leu Ala His Gln Ser Asn Ser Thr Asn Ile Phe Phe Ser Pro Val Ser
            340                 345                 350

Ile Ala Thr Ala Phe Ala Met Leu Ser Leu Gly Thr Lys Ala Asp Thr
        355                 360                 365

His Asp Glu Ile Leu Glu Gly Leu Asn Phe Asn Leu Thr Glu Ile Pro
    370                 375                 380

Glu Ala Gln Ile His Glu Gly Phe Gln Glu Leu Leu Arg Thr Leu Asn
385                 390                 395                 400

Gln Pro Asp Ser Gln Leu Gln Leu Thr Thr Gly Asn Phe Leu Phe Leu
                405                 410                 415

Ser Glu Gly Leu Lys Leu Val Asp Lys Phe Leu Glu Asp Val Lys Lys
            420                 425                 430

Leu Tyr His Ser Glu Ala Phe Thr Val Asn Phe Gly Asp Thr Glu Glu
        435                 440                 445

Ala Lys Lys Gln Ile Asn Asp Tyr Val Glu Lys Gly Thr Gln Gly Lys
    450                 455                 460

Ile Val Asp Leu Val Lys Glu Leu Asp Arg Asp Thr Val Phe Ala Leu
465                 470                 475                 480

Val Asn Tyr Ile Phe Phe Lys Gly Lys Trp Glu Arg Pro Phe Glu Val
                485                 490                 495

Lys Asp Thr Glu Glu Glu Asp Phe His Val Asp Gln Val Thr Thr Val
            500                 505                 510

Lys Val Pro Met Met Lys Arg Leu Gly Met Phe Asn Ile Gln His Cys
        515                 520                 525
```

Lys Lys Leu Ser Ser Trp Val Leu Leu Met Lys Tyr Leu Gly Asn Ala
530 535 540

Thr Ala Ile Phe Phe Leu Pro Asp Glu Gly Lys Leu Gln His Leu Glu
545 550 555 560

Asn Glu Leu Thr His Asp Ile Ile Thr Lys Phe Leu Glu Asn Glu Asp
565 570 575

Arg Arg Ser Ala Ser Leu His Leu Pro Lys Leu Ser Ile Thr Gly Thr
580 585 590

Tyr Asp Leu Lys Ser Val Leu Gly Gln Leu Gly Ile Thr Lys Val Phe
595 600 605

Ser Asn Gly Ala Asp Leu Ser Gly Val Thr Glu Glu Ala Pro Leu Lys
610 615 620

Leu Ser Lys Ala Val His Lys Ala Val Leu Thr Ile Asp Glu Lys Gly
625 630 635 640

Thr Glu Ala Ala Gly Ala Met Phe Leu Glu Ala Ile Pro Met Ser Ile
645 650 655

Pro Pro Glu Val Lys Phe Asn Lys Pro Phe Val Phe Leu Met Ile Glu
660 665 670

Gln Asn Thr Lys Ser Pro Leu Phe Met Gly Lys Val Val Asn Pro Thr
675 680 685

Gln Lys Lys Asp Glu Leu Gly Gly Ala Ala Val Ala Leu Leu Pro Ala
690 695 700

Val Leu Leu Ala Leu Leu Ala Pro Gly Gly Lys Lys Lys Arg Lys
705 710 715

<210> SEQ ID NO 75
<211> LENGTH: 701
<212> TYPE: PRT
<213> ORGANISM: Artificial Sequence
<220> FEATURE:
<223> OTHER INFORMATION: Synthetic

<400> SEQUENCE: 75

Met Arg Gly Ser His His His His His His Asp Tyr Asp Ile Pro Thr
1 5 10 15

Thr Glu Asn Leu Tyr Phe Gln Gly Ser Gly Gly Gly Gly Met Gln Ile
20 25 30

Phe Val Arg Thr Leu Thr Gly Arg Thr Ile Thr Leu Glu Val Glu Pro
35 40 45

Ser Asp Thr Ile Glu Asn Val Arg Ala Arg Ile Gln Asp Arg Glu Gly
50 55 60

Ile Pro Pro Asp Gln Gln Arg Leu Ile Phe Ala Gly Arg Gln Leu Glu
65 70 75 80

Asp Gly Arg Thr Leu Ser Asp Tyr Asn Ile Gln Arg Glu Ser Thr Leu
85 90 95

His Leu Val Leu Arg Leu Arg Gly Ala Gly Gly Glu Thr Phe Ser Asp
100 105 110

Leu Trp Lys Leu Leu Pro Glu Asn Gly Gly Gly Gly Gly Met Ala Glu
115 120 125

Pro Trp Gly Asn Glu Leu Ala Ser Ala Ala Ala Arg Gly Asp Leu Glu
130 135 140

Gln Leu Thr Ser Leu Leu Gln Asn Asn Val Asn Val Asn Ala Gln Asn
145 150 155 160

Gly Phe Gly Arg Thr Ala Leu Gln Val Met Lys Leu Gly Asn Pro Glu
165 170 175

```
Ile Ala Arg Arg Leu Leu Leu Arg Gly Ala Asn Pro Asp Leu Lys Asp
            180                 185                 190

Arg Thr Gly Asn Ala Val Ile His Asp Ala Ala Arg Ala Gly Phe Leu
        195                 200                 205

Asp Thr Leu Gln Thr Leu Leu Glu Phe Gln Ala Asp Val Asn Ile Glu
    210                 215                 220

Asp Asn Glu Gly Asn Leu Pro Leu His Leu Ala Ala Lys Glu Gly His
225                 230                 235                 240

Leu Arg Val Val Glu Phe Leu Val Lys His Thr Ala Ser Asn Val Gly
                245                 250                 255

His Arg Asn His Lys Gly Asp Thr Ala Cys Asp Leu Ala Arg Leu Tyr
            260                 265                 270

Gly Arg Asn Glu Val Val Ser Leu Met Gln Ala Asn Gly Ala Gly Gly
        275                 280                 285

Ala Thr Asn Leu Gln Gly Gly Met Glu Asp Pro Gln Gly Asp Ala Ala
    290                 295                 300

Gln Lys Thr Asp Thr Ser His His Asp Gln Asp His Pro Thr Phe Asn
305                 310                 315                 320

Lys Ile Thr Pro Asn Leu Ala Glu Phe Ala Phe Ser Leu Tyr Arg Gln
                325                 330                 335

Leu Ala His Gln Ser Asn Ser Thr Asn Ile Phe Phe Ser Pro Val Ser
            340                 345                 350

Ile Ala Thr Ala Phe Ala Met Leu Ser Leu Gly Thr Lys Ala Asp Thr
        355                 360                 365

His Asp Glu Ile Leu Glu Gly Leu Asn Phe Asn Leu Thr Glu Ile Pro
    370                 375                 380

Glu Ala Gln Ile His Glu Gly Phe Gln Glu Leu Leu Arg Thr Leu Asn
385                 390                 395                 400

Gln Pro Asp Ser Gln Leu Gln Leu Thr Thr Gly Asn Phe Leu Phe Leu
                405                 410                 415

Ser Glu Gly Leu Lys Leu Val Asp Lys Phe Leu Glu Asp Val Lys Lys
            420                 425                 430

Leu Tyr His Ser Glu Ala Phe Thr Val Asn Phe Gly Asp Thr Glu Glu
        435                 440                 445

Ala Lys Lys Gln Ile Asn Asp Tyr Val Glu Lys Gly Thr Gln Gly Lys
    450                 455                 460

Ile Val Asp Leu Val Lys Glu Leu Asp Arg Asp Thr Val Phe Ala Leu
465                 470                 475                 480

Val Asn Tyr Ile Phe Phe Lys Gly Lys Trp Glu Arg Pro Phe Glu Val
                485                 490                 495

Lys Asp Thr Glu Glu Glu Asp Phe His Val Asp Gln Val Thr Thr Val
            500                 505                 510

Lys Val Pro Met Met Lys Arg Leu Gly Met Phe Asn Ile Gln His Cys
        515                 520                 525

Lys Lys Leu Ser Ser Trp Val Leu Leu Met Lys Tyr Leu Gly Asn Ala
    530                 535                 540

Thr Ala Ile Phe Phe Leu Pro Asp Glu Gly Lys Leu Gln His Leu Glu
545                 550                 555                 560

Asn Glu Leu Thr His Asp Ile Ile Thr Lys Phe Leu Glu Asn Glu Asp
                565                 570                 575

Arg Arg Ser Ala Ser Leu His Leu Pro Lys Leu Ser Ile Thr Gly Thr
            580                 585                 590
```

```
Tyr Asp Leu Lys Ser Val Leu Gly Gln Leu Gly Ile Thr Lys Val Phe
        595                 600                 605

Ser Asn Gly Ala Asp Leu Ser Gly Val Thr Glu Glu Ala Pro Leu Lys
    610                 615                 620

Leu Ser Lys Ala Val His Lys Ala Val Leu Thr Ile Asp Glu Lys Gly
625                 630                 635                 640

Thr Glu Ala Ala Gly Ala Met Phe Leu Glu Ala Ile Pro Met Ser Ile
                645                 650                 655

Pro Pro Glu Val Lys Phe Asn Lys Pro Phe Val Phe Leu Met Ile Glu
            660                 665                 670

Gln Asn Thr Lys Ser Pro Leu Phe Met Gly Lys Val Val Asn Pro Thr
        675                 680                 685

Gln Lys Lys Asp Glu Leu Gly Gly Lys Lys Lys Arg Lys
    690                 695                 700


<210> SEQ ID NO 76
<211> LENGTH: 718
<212> TYPE: PRT
<213> ORGANISM: Artificial Sequence
<220> FEATURE:
<223> OTHER INFORMATION: Synthetic

<400> SEQUENCE: 76

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Glu Thr Phe Glu His
            100                 105                 110

Trp Trp Ser Gln Leu Leu Ser Gly Gly Gly Gly Gly Met Ala Glu Pro
        115                 120                 125

Trp Gly Asn Glu Leu Ala Ser Ala Ala Ala Arg Gly Asp Leu Glu Gln
    130                 135                 140

Leu Thr Ser Leu Leu Gln Asn Asn Val Asn Val Asn Ala Gln Asn Gly
145                 150                 155                 160

Phe Gly Arg Thr Ala Leu Gln Val Met Lys Leu Gly Asn Pro Glu Ile
                165                 170                 175

Ala Arg Arg Leu Leu Leu Arg Gly Ala Asn Pro Asp Leu Lys Asp Arg
            180                 185                 190

Thr Gly Asn Ala Val Ile His Asp Ala Ala Arg Ala Gly Phe Leu Asp
        195                 200                 205

Thr Leu Gln Thr Leu Leu Glu Phe Gln Ala Asp Val Asn Ile Glu Asp
    210                 215                 220

Asn Glu Gly Asn Leu Pro Leu His Leu Ala Ala Lys Glu Gly His Leu
225                 230                 235                 240

Arg Val Val Glu Phe Leu Val Lys His Thr Ala Ser Asn Val Gly His
                245                 250                 255
```

```
Arg Asn His Lys Gly Asp Thr Ala Cys Asp Leu Ala Arg Leu Tyr Gly
            260                 265                 270

Arg Asn Glu Val Val Ser Leu Met Gln Ala Asn Gly Ala Gly Gly Ala
        275                 280                 285

Thr Asn Leu Gln Gly Gly Met Glu Asp Pro Gln Gly Asp Ala Ala Gln
    290                 295                 300

Lys Thr Asp Thr Ser His His Asp Gln Asp His Pro Thr Phe Asn Lys
305                 310                 315                 320

Ile Thr Pro Asn Leu Ala Glu Phe Ala Phe Ser Leu Tyr Arg Gln Leu
                325                 330                 335

Ala His Gln Ser Asn Ser Thr Asn Ile Phe Phe Ser Pro Val Ser Ile
            340                 345                 350

Ala Thr Ala Phe Ala Met Leu Ser Leu Gly Thr Lys Ala Asp Thr His
        355                 360                 365

Asp Glu Ile Leu Glu Gly Leu Asn Phe Asn Leu Thr Glu Ile Pro Glu
    370                 375                 380

Ala Gln Ile His Glu Gly Phe Gln Glu Leu Leu Arg Thr Leu Asn Gln
385                 390                 395                 400

Pro Asp Ser Gln Leu Gln Leu Thr Thr Gly Asn Phe Leu Phe Leu Ser
                405                 410                 415

Glu Gly Leu Lys Leu Val Asp Lys Phe Leu Glu Asp Val Lys Lys Leu
            420                 425                 430

Tyr His Ser Glu Ala Phe Thr Val Asn Phe Gly Asp Thr Glu Glu Ala
        435                 440                 445

Lys Lys Gln Ile Asn Asp Tyr Val Glu Lys Gly Thr Gln Gly Lys Ile
    450                 455                 460

Val Asp Leu Val Lys Glu Leu Asp Arg Asp Thr Val Phe Ala Leu Val
465                 470                 475                 480

Asn Tyr Ile Phe Phe Lys Gly Lys Trp Glu Arg Pro Phe Glu Val Lys
                485                 490                 495

Asp Thr Glu Glu Glu Asp Phe His Val Asp Gln Val Thr Thr Val Lys
            500                 505                 510

Val Pro Met Met Lys Arg Leu Gly Met Phe Asn Ile Gln His Cys Lys
        515                 520                 525

Lys Leu Ser Ser Trp Val Leu Leu Met Lys Tyr Leu Gly Asn Ala Thr
    530                 535                 540

Ala Ile Phe Phe Leu Pro Asp Glu Gly Lys Leu Gln His Leu Glu Asn
545                 550                 555                 560

Glu Leu Thr His Asp Ile Ile Thr Lys Phe Leu Glu Asn Glu Asp Arg
                565                 570                 575

Arg Ser Ala Ser Leu His Leu Pro Lys Leu Ser Ile Thr Gly Thr Tyr
            580                 585                 590

Asp Leu Lys Ser Val Leu Gly Gln Leu Gly Ile Thr Lys Val Phe Ser
        595                 600                 605

Asn Gly Ala Asp Leu Ser Gly Val Thr Glu Glu Ala Pro Leu Lys Leu
    610                 615                 620

Ser Lys Ala Val His Lys Ala Val Leu Thr Ile Asp Glu Lys Gly Thr
625                 630                 635                 640

Glu Ala Ala Gly Ala Met Phe Leu Glu Ala Ile Pro Met Ser Ile Pro
                645                 650                 655

Pro Glu Val Lys Phe Asn Lys Pro Phe Val Phe Leu Met Ile Glu Gln
            660                 665                 670

Asn Thr Lys Ser Pro Leu Phe Met Gly Lys Val Val Asn Pro Thr Gln
```

```
        675                 680                 685

Lys Lys Asp Glu Leu Gly Gly Ala Ala Val Ala Leu Leu Pro Ala Val
    690                 695                 700

Leu Leu Ala Leu Leu Ala Pro Gly Gly Lys Lys Lys Arg Lys
705                 710                 715


<210> SEQ ID NO 77
<211> LENGTH: 548
<212> TYPE: PRT
<213> ORGANISM: Artificial Sequence
<220> FEATURE:
<223> OTHER INFORMATION: Synthetic

<400> SEQUENCE: 77

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Glu Thr Phe Glu His
            100                 105                 110

Trp Trp Ser Gln Leu Leu Ser Gly Gly Gly Gly Gly Met Glu Asp Pro
        115                 120                 125

Gln Gly Asp Ala Ala Gln Lys Thr Asp Thr Ser His His Asp Gln Asp
    130                 135                 140

His Pro Thr Phe Asn Lys Ile Thr Pro Asn Leu Ala Glu Phe Ala Phe
145                 150                 155                 160

Ser Leu Tyr Arg Gln Leu Ala His Gln Ser Asn Ser Thr Asn Ile Phe
                165                 170                 175

Phe Ser Pro Val Ser Ile Ala Thr Ala Phe Ala Met Leu Ser Leu Gly
            180                 185                 190

Thr Lys Ala Asp Thr His Asp Glu Ile Leu Glu Gly Leu Asn Phe Asn
        195                 200                 205

Leu Thr Glu Ile Pro Glu Ala Gln Ile His Glu Gly Phe Gln Glu Leu
    210                 215                 220

Leu Arg Thr Leu Asn Gln Pro Asp Ser Gln Leu Gln Leu Thr Thr Gly
225                 230                 235                 240

Asn Phe Leu Phe Leu Ser Glu Gly Leu Lys Leu Val Asp Lys Phe Leu
                245                 250                 255

Glu Asp Val Lys Lys Leu Tyr His Ser Glu Ala Phe Thr Val Asn Phe
            260                 265                 270

Gly Asp Thr Glu Glu Ala Lys Lys Gln Ile Asn Asp Tyr Val Glu Lys
        275                 280                 285

Gly Thr Gln Gly Lys Ile Val Asp Leu Val Lys Glu Leu Asp Arg Asp
    290                 295                 300

Thr Val Phe Ala Leu Val Asn Tyr Ile Phe Phe Lys Gly Lys Trp Glu
305                 310                 315                 320

Arg Pro Phe Glu Val Lys Asp Thr Glu Glu Glu Asp Phe His Val Asp
```

```
                325                 330                 335

Gln Val Thr Thr Val Lys Val Pro Met Met Lys Arg Leu Gly Met Phe
            340                 345                 350

Asn Ile Gln His Cys Lys Lys Leu Ser Ser Trp Val Leu Leu Met Lys
        355                 360                 365

Tyr Leu Gly Asn Ala Thr Ala Ile Phe Phe Leu Pro Asp Glu Gly Lys
    370                 375                 380

Leu Gln His Leu Glu Asn Glu Leu Thr His Asp Ile Ile Thr Lys Phe
385                 390                 395                 400

Leu Glu Asn Glu Asp Arg Arg Ser Ala Ser Leu His Leu Pro Lys Leu
                405                 410                 415

Ser Ile Thr Gly Thr Tyr Asp Leu Lys Ser Val Leu Gly Gln Leu Gly
            420                 425                 430

Ile Thr Lys Val Phe Ser Asn Gly Ala Asp Leu Ser Gly Val Thr Glu
        435                 440                 445

Glu Ala Pro Leu Lys Leu Ser Lys Ala Val His Lys Ala Val Leu Thr
    450                 455                 460

Ile Asp Glu Lys Gly Thr Glu Ala Ala Gly Ala Met Phe Leu Glu Ala
465                 470                 475                 480

Ile Pro Met Ser Ile Pro Pro Glu Val Lys Phe Asn Lys Pro Phe Val
                485                 490                 495

Phe Leu Met Ile Glu Gln Asn Thr Lys Ser Pro Leu Phe Met Gly Lys
            500                 505                 510

Val Val Asn Pro Thr Gln Lys Lys Asp Glu Leu Gly Gly Ala Ala Val
        515                 520                 525

Ala Leu Leu Pro Ala Val Leu Leu Ala Leu Leu Ala Pro Gly Gly Lys
    530                 535                 540

Lys Lys Arg Lys
545


<210> SEQ ID NO 78
<211> LENGTH: 718
<212> TYPE: PRT
<213> ORGANISM: Artificial Sequence
<220> FEATURE:
<223> OTHER INFORMATION: Synthetic

<400> SEQUENCE: 78

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Thr Ser Phe Ala Glu
            100                 105                 110

Tyr Trp Asn Leu Leu Ser Pro Gly Gly Gly Gly Gly Met Ala Glu Pro
        115                 120                 125

Trp Gly Asn Glu Leu Ala Ser Ala Ala Ala Arg Gly Asp Leu Glu Gln
```

```
    130                 135                 140

Leu Thr Ser Leu Leu Gln Asn Asn Val Asn Val Asn Ala Gln Asn Gly
145                 150                 155                 160

Phe Gly Arg Thr Ala Leu Gln Val Met Lys Leu Gly Asn Pro Glu Ile
                165                 170                 175

Ala Arg Arg Leu Leu Leu Arg Gly Ala Asn Pro Asp Leu Lys Asp Arg
            180                 185                 190

Thr Gly Asn Ala Val Ile His Asp Ala Ala Arg Ala Gly Phe Leu Asp
        195                 200                 205

Thr Leu Gln Thr Leu Leu Glu Phe Gln Ala Asp Val Asn Ile Glu Asp
    210                 215                 220

Asn Glu Gly Asn Leu Pro Leu His Leu Ala Ala Lys Glu Gly His Leu
225                 230                 235                 240

Arg Val Val Glu Phe Leu Val Lys His Thr Ala Ser Asn Val Gly His
                245                 250                 255

Arg Asn His Lys Gly Asp Thr Ala Cys Asp Leu Ala Arg Leu Tyr Gly
            260                 265                 270

Arg Asn Glu Val Val Ser Leu Met Gln Ala Asn Gly Ala Gly Gly Ala
        275                 280                 285

Thr Asn Leu Gln Gly Gly Met Glu Asp Pro Gln Gly Asp Ala Ala Gln
    290                 295                 300

Lys Thr Asp Thr Ser His His Asp Gln Asp His Pro Thr Phe Asn Lys
305                 310                 315                 320

Ile Thr Pro Asn Leu Ala Glu Phe Ala Phe Ser Leu Tyr Arg Gln Leu
                325                 330                 335

Ala His Gln Ser Asn Ser Thr Asn Ile Phe Phe Ser Pro Val Ser Ile
            340                 345                 350

Ala Thr Ala Phe Ala Met Leu Ser Leu Gly Thr Lys Ala Asp Thr His
        355                 360                 365

Asp Glu Ile Leu Glu Gly Leu Asn Phe Asn Leu Thr Glu Ile Pro Glu
    370                 375                 380

Ala Gln Ile His Glu Gly Phe Gln Glu Leu Leu Arg Thr Leu Asn Gln
385                 390                 395                 400

Pro Asp Ser Gln Leu Gln Leu Thr Thr Gly Asn Phe Leu Phe Leu Ser
                405                 410                 415

Glu Gly Leu Lys Leu Val Asp Lys Phe Leu Glu Asp Val Lys Lys Leu
            420                 425                 430

Tyr His Ser Glu Ala Phe Thr Val Asn Phe Gly Asp Thr Glu Glu Ala
        435                 440                 445

Lys Lys Gln Ile Asn Asp Tyr Val Glu Lys Gly Thr Gln Gly Lys Ile
    450                 455                 460

Val Asp Leu Val Lys Glu Leu Asp Arg Asp Thr Val Phe Ala Leu Val
465                 470                 475                 480

Asn Tyr Ile Phe Phe Lys Gly Lys Trp Glu Arg Pro Phe Glu Val Lys
                485                 490                 495

Asp Thr Glu Glu Glu Asp Phe His Val Asp Gln Val Thr Thr Val Lys
            500                 505                 510

Val Pro Met Met Lys Arg Leu Gly Met Phe Asn Ile Gln His Cys Lys
        515                 520                 525

Lys Leu Ser Ser Trp Val Leu Leu Met Lys Tyr Leu Gly Asn Ala Thr
    530                 535                 540

Ala Ile Phe Phe Leu Pro Asp Glu Gly Lys Leu Gln His Leu Glu Asn
545                 550                 555                 560
```

```
Glu Leu Thr His Asp Ile Ile Thr Lys Phe Leu Glu Asn Glu Asp Arg
                565                 570                 575

Arg Ser Ala Ser Leu His Leu Pro Lys Leu Ser Ile Thr Gly Thr Tyr
            580                 585                 590

Asp Leu Lys Ser Val Leu Gly Gln Leu Gly Ile Thr Lys Val Phe Ser
        595                 600                 605

Asn Gly Ala Asp Leu Ser Gly Val Thr Glu Glu Ala Pro Leu Lys Leu
    610                 615                 620

Ser Lys Ala Val His Lys Ala Val Leu Thr Ile Asp Glu Lys Gly Thr
625                 630                 635                 640

Glu Ala Ala Gly Ala Met Phe Leu Glu Ala Ile Pro Met Ser Ile Pro
                645                 650                 655

Pro Glu Val Lys Phe Asn Lys Pro Phe Val Phe Leu Met Ile Glu Gln
            660                 665                 670

Asn Thr Lys Ser Pro Leu Phe Met Gly Lys Val Val Asn Pro Thr Gln
        675                 680                 685

Lys Lys Asp Glu Leu Gly Gly Ala Ala Val Ala Leu Leu Pro Ala Val
    690                 695                 700

Leu Leu Ala Leu Leu Ala Pro Gly Gly Lys Lys Lys Arg Lys
705                 710                 715


<210> SEQ ID NO 79
<211> LENGTH: 548
<212> TYPE: PRT
<213> ORGANISM: Artificial Sequence
<220> FEATURE:
<223> OTHER INFORMATION: Synthetic

<400> SEQUENCE: 79

Met Arg Gly Ser His His His His His His Asp Tyr Asp Ile Pro Thr
1               5                   10                  15

Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Thr Ser Phe Ala Glu
            100                 105                 110

Tyr Trp Asn Leu Leu Ser Pro Gly Gly Gly Gly Gly Met Glu Asp Pro
        115                 120                 125

Gln Gly Asp Ala Ala Gln Lys Thr Asp Thr Ser His His Asp Gln Asp
    130                 135                 140

His Pro Thr Phe Asn Lys Ile Thr Pro Asn Leu Ala Glu Phe Ala Phe
145                 150                 155                 160

Ser Leu Tyr Arg Gln Leu Ala His Gln Ser Asn Ser Thr Asn Ile Phe
                165                 170                 175

Phe Ser Pro Val Ser Ile Ala Thr Ala Phe Ala Met Leu Ser Leu Gly
            180                 185                 190

Thr Lys Ala Asp Thr His Asp Glu Ile Leu Glu Gly Leu Asn Phe Asn
        195                 200                 205
```

```
Leu Thr Glu Ile Pro Glu Ala Gln Ile His Glu Gly Phe Gln Glu Leu
    210                 215                 220

Leu Arg Thr Leu Asn Gln Pro Asp Ser Gln Leu Gln Leu Thr Thr Gly
225                 230                 235                 240

Asn Phe Leu Phe Leu Ser Glu Gly Leu Lys Leu Val Asp Lys Phe Leu
                245                 250                 255

Glu Asp Val Lys Lys Leu Tyr His Ser Glu Ala Phe Thr Val Asn Phe
            260                 265                 270

Gly Asp Thr Glu Glu Ala Lys Lys Gln Ile Asn Asp Tyr Val Glu Lys
        275                 280                 285

Gly Thr Gln Gly Lys Ile Val Asp Leu Val Lys Glu Leu Asp Arg Asp
    290                 295                 300

Thr Val Phe Ala Leu Val Asn Tyr Ile Phe Phe Lys Gly Lys Trp Glu
305                 310                 315                 320

Arg Pro Phe Glu Val Lys Asp Thr Glu Glu Glu Asp Phe His Val Asp
                325                 330                 335

Gln Val Thr Thr Val Lys Val Pro Met Met Lys Arg Leu Gly Met Phe
            340                 345                 350

Asn Ile Gln His Cys Lys Lys Leu Ser Ser Trp Val Leu Leu Met Lys
        355                 360                 365

Tyr Leu Gly Asn Ala Thr Ala Ile Phe Phe Leu Pro Asp Glu Gly Lys
    370                 375                 380

Leu Gln His Leu Glu Asn Glu Leu Thr His Asp Ile Ile Thr Lys Phe
385                 390                 395                 400

Leu Glu Asn Glu Asp Arg Arg Ser Ala Ser Leu His Leu Pro Lys Leu
                405                 410                 415

Ser Ile Thr Gly Thr Tyr Asp Leu Lys Ser Val Leu Gly Gln Leu Gly
            420                 425                 430

Ile Thr Lys Val Phe Ser Asn Gly Ala Asp Leu Ser Gly Val Thr Glu
        435                 440                 445

Glu Ala Pro Leu Lys Leu Ser Lys Ala Val His Lys Ala Val Leu Thr
    450                 455                 460

Ile Asp Glu Lys Gly Thr Glu Ala Ala Gly Ala Met Phe Leu Glu Ala
465                 470                 475                 480

Ile Pro Met Ser Ile Pro Pro Glu Val Lys Phe Asn Lys Pro Phe Val
                485                 490                 495

Phe Leu Met Ile Glu Gln Asn Thr Lys Ser Pro Leu Phe Met Gly Lys
            500                 505                 510

Val Val Asn Pro Thr Gln Lys Lys Asp Glu Leu Gly Gly Ala Ala Val
        515                 520                 525

Ala Leu Leu Pro Ala Val Leu Leu Ala Leu Leu Ala Pro Gly Gly Lys
    530                 535                 540

Lys Lys Arg Lys
545


<210> SEQ ID NO 80
<211> LENGTH: 718
<212> TYPE: PRT
<213> ORGANISM: Artificial Sequence
<220> FEATURE:
<223> OTHER INFORMATION: Synthetic

<400> SEQUENCE: 80

Met Arg Gly Ser His His His His His His Asp Tyr Asp Ile Pro Thr
1               5                   10                  15
```

```
Thr Glu Asn Leu Tyr Phe Gln Gly Ser Gly Gly Gly Gly Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Glu Thr Phe Glu His
            100                 105                 110

Trp Trp Asn Leu Leu Ser Pro Gly Gly Gly Gly Gly Met Ala Glu Pro
        115                 120                 125

Trp Gly Asn Glu Leu Ala Ser Ala Ala Ala Arg Gly Asp Leu Glu Gln
    130                 135                 140

Leu Thr Ser Leu Leu Gln Asn Asn Val Asn Val Asn Ala Gln Asn Gly
145                 150                 155                 160

Phe Gly Arg Thr Ala Leu Gln Val Met Lys Leu Gly Asn Pro Glu Ile
                165                 170                 175

Ala Arg Arg Leu Leu Leu Arg Gly Ala Asn Pro Asp Leu Lys Asp Arg
            180                 185                 190

Thr Gly Asn Ala Val Ile His Asp Ala Ala Arg Ala Gly Phe Leu Asp
        195                 200                 205

Thr Leu Gln Thr Leu Leu Glu Phe Gln Ala Asp Val Asn Ile Glu Asp
    210                 215                 220

Asn Glu Gly Asn Leu Pro Leu His Leu Ala Ala Lys Glu Gly His Leu
225                 230                 235                 240

Arg Val Val Glu Phe Leu Val Lys His Thr Ala Ser Asn Val Gly His
                245                 250                 255

Arg Asn His Lys Gly Asp Thr Ala Cys Asp Leu Ala Arg Leu Tyr Gly
            260                 265                 270

Arg Asn Glu Val Val Ser Leu Met Gln Ala Asn Gly Ala Gly Gly Ala
        275                 280                 285

Thr Asn Leu Gln Gly Gly Met Glu Asp Pro Gln Gly Asp Ala Ala Gln
    290                 295                 300

Lys Thr Asp Thr Ser His His Asp Gln Asp His Pro Thr Phe Asn Lys
305                 310                 315                 320

Ile Thr Pro Asn Leu Ala Glu Phe Ala Phe Ser Leu Tyr Arg Gln Leu
                325                 330                 335

Ala His Gln Ser Asn Ser Thr Asn Ile Phe Phe Ser Pro Val Ser Ile
            340                 345                 350

Ala Thr Ala Phe Ala Met Leu Ser Leu Gly Thr Lys Ala Asp Thr His
        355                 360                 365

Asp Glu Ile Leu Glu Gly Leu Asn Phe Asn Leu Thr Glu Ile Pro Glu
    370                 375                 380

Ala Gln Ile His Glu Gly Phe Gln Glu Leu Leu Arg Thr Leu Asn Gln
385                 390                 395                 400

Pro Asp Ser Gln Leu Gln Leu Thr Thr Gly Asn Phe Leu Phe Leu Ser
                405                 410                 415

Glu Gly Leu Lys Leu Val Asp Lys Phe Leu Glu Asp Val Lys Lys Leu
            420                 425                 430
```

Tyr His Ser Glu Ala Phe Thr Val Asn Phe Gly Asp Thr Glu Glu Ala
435 440 445

Lys Lys Gln Ile Asn Asp Tyr Val Glu Lys Gly Thr Gln Gly Lys Ile
450 455 460

Val Asp Leu Val Lys Glu Leu Asp Arg Asp Thr Val Phe Ala Leu Val
465 470 475 480

Asn Tyr Ile Phe Phe Lys Gly Lys Trp Glu Arg Pro Phe Glu Val Lys
485 490 495

Asp Thr Glu Glu Glu Asp Phe His Val Asp Gln Val Thr Thr Val Lys
500 505 510

Val Pro Met Met Lys Arg Leu Gly Met Phe Asn Ile Gln His Cys Lys
515 520 525

Lys Leu Ser Ser Trp Val Leu Leu Met Lys Tyr Leu Gly Asn Ala Thr
530 535 540

Ala Ile Phe Phe Leu Pro Asp Glu Gly Lys Leu Gln His Leu Glu Asn
545 550 555 560

Glu Leu Thr His Asp Ile Ile Thr Lys Phe Leu Glu Asn Glu Asp Arg
565 570 575

Arg Ser Ala Ser Leu His Leu Pro Lys Leu Ser Ile Thr Gly Thr Tyr
580 585 590

Asp Leu Lys Ser Val Leu Gly Gln Leu Gly Ile Thr Lys Val Phe Ser
595 600 605

Asn Gly Ala Asp Leu Ser Gly Val Thr Glu Glu Ala Pro Leu Lys Leu
610 615 620

Ser Lys Ala Val His Lys Ala Val Leu Thr Ile Asp Glu Lys Gly Thr
625 630 635 640

Glu Ala Ala Gly Ala Met Phe Leu Glu Ala Ile Pro Met Ser Ile Pro
645 650 655

Pro Glu Val Lys Phe Asn Lys Pro Phe Val Phe Leu Met Ile Glu Gln
660 665 670

Asn Thr Lys Ser Pro Leu Phe Met Gly Lys Val Val Asn Pro Thr Gln
675 680 685

Lys Lys Asp Glu Leu Gly Gly Ala Ala Val Ala Leu Leu Pro Ala Val
690 695 700

Leu Leu Ala Leu Leu Ala Pro Gly Gly Lys Lys Lys Arg Lys
705 710 715

<210> SEQ ID NO 81
<211> LENGTH: 548
<212> TYPE: PRT
<213> ORGANISM: Artificial Sequence
<220> FEATURE:
<223> OTHER INFORMATION: Synthetic

<400> SEQUENCE: 81

Met Arg Gly Ser His His His His His His Asp Tyr Asp Ile Pro Thr
1 5 10 15

Thr Glu Asn Leu Tyr Phe Gln Gly Ser Gly Gly Gly Gly Met Gln Ile
20 25 30

Phe Val Arg Thr Leu Thr Gly Arg Thr Ile Thr Leu Glu Val Glu Pro
35 40 45

Ser Asp Thr Ile Glu Asn Val Arg Ala Arg Ile Gln Asp Arg Glu Gly
50 55 60

Ile Pro Pro Asp Gln Gln Arg Leu Ile Phe Ala Gly Arg Gln Leu Glu
65 70 75 80

```
Asp Gly Arg Thr Leu Ser Asp Tyr Asn Ile Gln Arg Glu Ser Thr Leu
                85                  90                  95

His Leu Val Leu Arg Leu Arg Gly Ala Gly Gly Glu Thr Phe Glu His
            100                 105                 110

Trp Trp Asn Leu Leu Ser Pro Gly Gly Gly Gly Gly Met Glu Asp Pro
        115                 120                 125

Gln Gly Asp Ala Ala Gln Lys Thr Asp Thr Ser His His Asp Gln Asp
    130                 135                 140

His Pro Thr Phe Asn Lys Ile Thr Pro Asn Leu Ala Glu Phe Ala Phe
145                 150                 155                 160

Ser Leu Tyr Arg Gln Leu Ala His Gln Ser Asn Ser Thr Asn Ile Phe
                165                 170                 175

Phe Ser Pro Val Ser Ile Ala Thr Ala Phe Ala Met Leu Ser Leu Gly
            180                 185                 190

Thr Lys Ala Asp Thr His Asp Glu Ile Leu Glu Gly Leu Asn Phe Asn
        195                 200                 205

Leu Thr Glu Ile Pro Glu Ala Gln Ile His Glu Gly Phe Gln Glu Leu
    210                 215                 220

Leu Arg Thr Leu Asn Gln Pro Asp Ser Gln Leu Gln Leu Thr Thr Gly
225                 230                 235                 240

Asn Phe Leu Phe Leu Ser Glu Gly Leu Lys Leu Val Asp Lys Phe Leu
                245                 250                 255

Glu Asp Val Lys Lys Leu Tyr His Ser Glu Ala Phe Thr Val Asn Phe
            260                 265                 270

Gly Asp Thr Glu Glu Ala Lys Lys Gln Ile Asn Asp Tyr Val Glu Lys
        275                 280                 285

Gly Thr Gln Gly Lys Ile Val Asp Leu Val Lys Glu Leu Asp Arg Asp
    290                 295                 300

Thr Val Phe Ala Leu Val Asn Tyr Ile Phe Phe Lys Gly Lys Trp Glu
305                 310                 315                 320

Arg Pro Phe Glu Val Lys Asp Thr Glu Glu Glu Asp Phe His Val Asp
                325                 330                 335

Gln Val Thr Thr Val Lys Val Pro Met Met Lys Arg Leu Gly Met Phe
            340                 345                 350

Asn Ile Gln His Cys Lys Lys Leu Ser Ser Trp Val Leu Leu Met Lys
        355                 360                 365

Tyr Leu Gly Asn Ala Thr Ala Ile Phe Phe Leu Pro Asp Glu Gly Lys
    370                 375                 380

Leu Gln His Leu Glu Asn Glu Leu Thr His Asp Ile Ile Thr Lys Phe
385                 390                 395                 400

Leu Glu Asn Glu Asp Arg Arg Ser Ala Ser Leu His Leu Pro Lys Leu
                405                 410                 415

Ser Ile Thr Gly Thr Tyr Asp Leu Lys Ser Val Leu Gly Gln Leu Gly
            420                 425                 430

Ile Thr Lys Val Phe Ser Asn Gly Ala Asp Leu Ser Gly Val Thr Glu
        435                 440                 445

Glu Ala Pro Leu Lys Leu Ser Lys Ala Val His Lys Ala Val Leu Thr
    450                 455                 460

Ile Asp Glu Lys Gly Thr Glu Ala Ala Gly Ala Met Phe Leu Glu Ala
465                 470                 475                 480

Ile Pro Met Ser Ile Pro Pro Glu Val Lys Phe Asn Lys Pro Phe Val
                485                 490                 495

Phe Leu Met Ile Glu Gln Asn Thr Lys Ser Pro Leu Phe Met Gly Lys
```

```
            500                 505                 510

Val Val Asn Pro Thr Gln Lys Lys Asp Glu Leu Gly Gly Ala Ala Val
        515                 520                 525

Ala Leu Leu Pro Ala Val Leu Leu Ala Leu Leu Ala Pro Gly Gly Lys
    530                 535                 540

Lys Lys Arg Lys
545


<210> SEQ ID NO 82
<211> LENGTH: 311
<212> TYPE: PRT
<213> ORGANISM: Artificial Sequence
<220> FEATURE:
<223> OTHER INFORMATION: Synthetic

<400> SEQUENCE: 82

Met Arg Gly Ser His His His His His His Asp Tyr Asp Ile Pro Thr
1               5                   10                  15

Thr Glu Asn Leu Tyr Phe Gln Gly Ser Gly Ser Gly Ser Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Glu Phe Ala Ala Val Ala Leu
            100                 105                 110

Leu Pro Ala Val Leu Leu Ala Leu Leu Ala Pro Glu Thr Phe Ser Asp
        115                 120                 125

Leu Trp Lys Leu Leu Pro Glu Asn Lys Leu Met Ala Glu Pro Trp Gly
    130                 135                 140

Asn Glu Leu Ala Ser Ala Ala Ala Arg Gly Asp Leu Glu Gln Leu Thr
145                 150                 155                 160

Ser Leu Leu Gln Asn Asn Val Asn Val Asn Ala Gln Asn Gly Phe Gly
                165                 170                 175

Arg Thr Ala Leu Gln Val Met Lys Leu Gly Asn Pro Glu Ile Ala Arg
            180                 185                 190

Arg Leu Leu Leu Arg Gly Ala Asn Pro Asp Leu Lys Asp Arg Thr Gly
        195                 200                 205

Asn Ala Val Ile His Asp Ala Ala Arg Ala Gly Phe Leu Asp Thr Leu
    210                 215                 220

Gln Thr Leu Leu Glu Phe Gln Ala Asp Val Asn Ile Glu Asp Asn Glu
225                 230                 235                 240

Gly Asn Leu Pro Leu His Leu Ala Ala Lys Glu Gly His Leu Arg Val
                245                 250                 255

Val Glu Phe Leu Val Lys His Thr Ala Ser Asn Val Gly His Arg Asn
            260                 265                 270

His Lys Gly Asp Thr Ala Cys Asp Leu Ala Arg Leu Tyr Gly Arg Asn
        275                 280                 285

Glu Val Val Ser Leu Met Gln Ala Asn Gly Ala Gly Gly Ala Thr Asn
    290                 295                 300

Leu Gln Lys Lys Lys Arg Lys
```

305 310

<210> SEQ ID NO 83
<211> LENGTH: 965
<212> TYPE: DNA
<213> ORGANISM: Artificial Sequence
<220> FEATURE:
<223> OTHER INFORMATION: Synthetic

<400> SEQUENCE: 83
catatgagag gatcgcatca ccatcaccat cacgattacg atatcccaac gaccgaaaac 60
ctgtattttc agggatccgg tagtggaagc atgcagattt tcgtgagaac ccttacgggg 120
aggaccatca ccctcgaagt tgaaccctcg gatacgatag aaaatgtaag ggccagaatc 180
caggataggg aaggaatacc tcctgatcag cagagactga tctttgctgg caggcagctg 240
gaagatggac gtactttgtc tgactacaat attcaaaggg agtctactct tcatcttgtg 300
ttgagacttc gtggtgctga attcgccgcg gtagcgctgc tcccggcggt cctgctggcc 360
ttgctggcgc ccgaaacatt ttcagaccta tggaaactac ttcctgaaaa caagcttatg 420
gccgagcctt gggggaacga gttggcgtcc gcagctgcca ggggggacct agagcaactt 480
actagtttgt tgcaaaataa tgtaaacgtc aatgcacaaa atggatttgg aaggactgcg 540
ctgcaggtta tgaaacttgg aaatcccgag attgccagga gactgctact tagaggtgct 600
aatcccgatt tgaaagaccg aactggtaat gctgtcattc atgatgcggc cagagcaggt 660
ttcctggaca ctttacagac tttgctggag tttcaagctg atgttaacat cgaggataat 720
gaagggaacc tgcccttgca cttggctgcc aaagaaggcc acctccgggt ggtggagttc 780
ctggtgaagc acacggccag caatgtgggg catcggaacc ataaggggga caccgcctgt 840
gatttggcca ggctctatgg gaggaatgag gttgttagcc tgatgcaggc aaacggggct 900
gggggagcca caaatcttca aaaaaagaag agaaagtaac tcgagcacca ccaccaccac 960
cactg 965

<210> SEQ ID NO 84
<211> LENGTH: 328
<212> TYPE: PRT
<213> ORGANISM: Artificial Sequence
<220> FEATURE:
<223> OTHER INFORMATION: Synthetic

<400> SEQUENCE: 84

Met Arg Gly Ser His His His His His His Asp Tyr Asp Ile Pro Thr
1               5                   10                  15

Thr Glu Asn Leu Tyr Phe Gln Gly Ser Gly Ser Gly Ser Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Glu Phe Ala Ala Val Ala Leu
            100                 105                 110

Leu Pro Ala Val Leu Leu Ala Leu Leu Ala Pro Glu Thr Phe Ser Asp
        115                 120                 125

```
Leu Trp Lys Leu Leu Pro Glu Asn Lys Leu Met Ala Glu Pro Trp Gly
    130                 135                 140

Asn Glu Leu Ala Ser Ala Ala Ala Arg Gly Asp Leu Glu Gln Leu Thr
145                 150                 155                 160

Ser Leu Leu Gln Asn Asn Val Asn Val Asn Ala Gln Asn Gly Phe Gly
                165                 170                 175

Arg Thr Ala Leu Gln Val Met Lys Leu Gly Asn Pro Glu Ile Ala Arg
            180                 185                 190

Arg Leu Leu Leu Arg Gly Ala Asn Pro Asp Leu Lys Asp Arg Thr Gly
        195                 200                 205

Asn Ala Val Ile His Asp Ala Ala Arg Ala Gly Phe Leu Asp Thr Leu
    210                 215                 220

Gln Thr Leu Leu Glu Phe Gln Ala Asp Val Asn Ile Glu Asp Asn Glu
225                 230                 235                 240

Gly Asn Leu Pro Leu His Leu Ala Ala Lys Glu Gly His Leu Arg Val
                245                 250                 255

Val Glu Phe Leu Val Lys His Thr Ala Ser Asn Val Gly His Arg Asn
            260                 265                 270

His Lys Gly Asp Thr Ala Cys Asp Leu Ala Arg Leu Tyr Gly Arg Asn
        275                 280                 285

Glu Val Val Ser Leu Met Gln Ala Asn Gly Ala Gly Gly Ala Thr Asn
    290                 295                 300

Leu Gln Lys Lys Lys Arg Lys Gly Gly Gly Ser Asp Ile Cys Leu Pro
305                 310                 315                 320

Arg Trp Gly Cys Leu Trp Glu Asp
                325
```

<210> SEQ ID NO 85
<211> LENGTH: 1016
<212> TYPE: DNA
<213> ORGANISM: Artificial Sequence
<220> FEATURE:
<223> OTHER INFORMATION: Synthetic

<400> SEQUENCE: 85

```
catatgagag gatcgcatca ccatcaccat cacgattacg atatcccaac gaccgaaaac     60

ctgtattttc agggatccgg tagtggaagc atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctga attcgccgcg gtagcgctgc tcccggcggt cctgctggcc    360

ttgctggcgc ccgaaacatt ttcagaccta tggaaactac ttcctgaaaa caagcttatg    420

gccgagcctt gggggaacga gttggcgtcc gcagctgcca gggggacct agagcaactt    480

actagtttgt tgcaaaataa tgtaaacgtc aatgcacaaa atggatttgg aaggactgcg    540

ctgcaggtta tgaaacttgg aaatcccgag attgccagga gactgctact tagaggtgct    600

aatcccgatt tgaaagaccg aactggtaat gctgtcattc atgatgcggc cagagcaggt    660

ttcctggaca ctttacagac tttgctggag tttcaagctg atgttaacat cgaggataat    720

gaagggaacc tgcccttgca cttggctgcc aaagaaggcc acctccgggt ggtggagttc    780

ctggtgaagc acacggccag caatgtgggg catcggaacc ataaggggga caccgcctgt    840

gatttggcca ggctctatgg gaggaatgag gttgttagcc tgatgcaggc aaacggggct    900
```

```
gggggagcca caaatcttca aaaaaagaag agaaagggtg gaggtagtga tatctgtctg    960

cctcgttggg gttgtctgtg ggaagattaa ctcgagcacc accaccacca ccactg      1016


<210> SEQ ID NO 86
<211> LENGTH: 311
<212> TYPE: PRT
<213> ORGANISM: Artificial Sequence
<220> FEATURE:
<223> OTHER INFORMATION: Synthetic

<400> SEQUENCE: 86

Met Arg Gly Ser His His His His His His Asp Tyr Asp Ile Pro Thr
1               5                   10                  15

Thr Glu Asn Leu Tyr Phe Gln Gly Ser Gly Ser Gly Ser Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Gly Glu Phe Ala Ala Val Ala Leu
            100                 105                 110

Leu Pro Ala Val Leu Leu Ala Leu Leu Ala Pro Glu Thr Phe Ser Asp
        115                 120                 125

Leu Trp Lys Leu Leu Pro Glu Asn Lys Leu Met Ala Glu Pro Trp Gly
    130                 135                 140

Asn Glu Leu Ala Ser Ala Ala Ala Arg Gly Asp Leu Glu Gln Leu Thr
145                 150                 155                 160

Ser Leu Leu Gln Asn Asn Val Asn Val Asn Ala Gln Asn Gly Phe Gly
                165                 170                 175

Arg Thr Ala Leu Gln Val Met Lys Leu Gly Asn Pro Glu Ile Ala Arg
            180                 185                 190

Arg Leu Leu Leu Arg Gly Ala Asn Pro Asp Leu Lys Asp Arg Thr Gly
        195                 200                 205

Asn Ala Val Ile His Asp Ala Ala Arg Ala Gly Phe Leu Asp Thr Leu
    210                 215                 220

Gln Thr Leu Leu Glu Phe Gln Ala Asp Val Asn Ile Glu Asp Asn Glu
225                 230                 235                 240

Gly Asn Leu Pro Leu His Leu Ala Ala Lys Glu Gly His Leu Arg Val
                245                 250                 255

Val Glu Phe Leu Val Lys His Thr Ala Ser Asn Val Gly His Arg Asn
            260                 265                 270

His Lys Gly Asp Thr Ala Cys Asp Leu Ala Arg Leu Tyr Gly Arg Asn
        275                 280                 285

Glu Val Val Ser Leu Met Gln Ala Asn Gly Ala Gly Gly Ala Thr Asn
    290                 295                 300

Leu Gln Lys Lys Lys Arg Lys
305                 310


<210> SEQ ID NO 87
<211> LENGTH: 965
<212> TYPE: DNA
```

<213> ORGANISM: Artificial Sequence
<220> FEATURE:
<223> OTHER INFORMATION: Synthetic

<400> SEQUENCE: 87

```
catatgagag gatcgcatca ccatcaccat cacgattacg atatcccaac gaccgaaaac     60

ctgtattttc agggatccgg tagtggaagc atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtggtga attcgccgcg gtagcgctgc tcccggcggt cctgctggcc    360

ttgctggcgc ccgaaacatt ttcagaccta tggaaactac ttcctgaaaa caagcttatg    420

gccgagcctt gggggaacga gttggcgtcc gcagctgcca ggggggacct agagcaactt    480

actagtttgt tgcaaaataa tgtaaacgtc aatgcacaaa atggatttgg aaggactgcg    540

ctgcaggtta tgaaacttgg aaatcccgag attgccagga gactgctact tagaggtgct    600

aatcccgatt tgaaagaccg aactggtaat gctgtcattc atgatgcggc cagagcaggt    660

ttcctggaca ctttacagac tttgctggag tttcaagctg atgttaacat cgaggataat    720

gaagggaacc tgcccttgca cttggctgcc aaagaaggcc acctccgggt ggtggagttc    780

ctggtgaagc acacggccag caatgtgggg catcggaacc ataaggggga caccgcctgt    840

gatttggcca ggctctatgg gaggaatgag gttgttagcc tgatgcaggc aaacggggct    900

gggggagcca caaatcttca aaaaaagaag agaaagtaac tcgagcacca ccaccaccac    960

cactg                                                                965
```

<210> SEQ ID NO 88
<211> LENGTH: 328
<212> TYPE: PRT
<213> ORGANISM: Artificial Sequence
<220> FEATURE:
<223> OTHER INFORMATION: Synthetic

<400> SEQUENCE: 88

```
Met Arg Gly Ser His His His His His His Asp Tyr Asp Ile Pro Thr
1               5                   10                  15

Thr Glu Asn Leu Tyr Phe Gln Gly Ser Gly Ser Gly Ser Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Gly Glu Phe Ala Ala Val Ala Leu
            100                 105                 110

Leu Pro Ala Val Leu Leu Ala Leu Leu Ala Pro Glu Thr Phe Ser Asp
        115                 120                 125

Leu Trp Lys Leu Leu Pro Glu Asn Lys Leu Met Ala Glu Pro Trp Gly
    130                 135                 140

Asn Glu Leu Ala Ser Ala Ala Ala Arg Gly Asp Leu Glu Gln Leu Thr
145                 150                 155                 160
```

```
Ser Leu Leu Gln Asn Asn Val Asn Val Asn Ala Gln Asn Gly Phe Gly
                165                 170                 175

Arg Thr Ala Leu Gln Val Met Lys Leu Gly Asn Pro Glu Ile Ala Arg
            180                 185                 190

Arg Leu Leu Leu Arg Gly Ala Asn Pro Asp Leu Lys Asp Arg Thr Gly
        195                 200                 205

Asn Ala Val Ile His Asp Ala Ala Arg Ala Gly Phe Leu Asp Thr Leu
    210                 215                 220

Gln Thr Leu Leu Glu Phe Gln Ala Asp Val Asn Ile Glu Asp Asn Glu
225                 230                 235                 240

Gly Asn Leu Pro Leu His Leu Ala Ala Lys Glu Gly His Leu Arg Val
                245                 250                 255

Val Glu Phe Leu Val Lys His Thr Ala Ser Asn Val Gly His Arg Asn
            260                 265                 270

His Lys Gly Asp Thr Ala Cys Asp Leu Ala Arg Leu Tyr Gly Arg Asn
        275                 280                 285

Glu Val Val Ser Leu Met Gln Ala Asn Gly Ala Gly Gly Ala Thr Asn
    290                 295                 300

Leu Gln Lys Lys Lys Arg Lys Gly Gly Gly Ser Asp Ile Cys Leu Pro
305                 310                 315                 320

Arg Trp Gly Cys Leu Trp Glu Asp
                325
```

<210> SEQ ID NO 89
<211> LENGTH: 1016
<212> TYPE: DNA
<213> ORGANISM: Artificial Sequence
<220> FEATURE:
<223> OTHER INFORMATION: Synthetic

<400> SEQUENCE: 89

```
catatgagag gatcgcatca ccatcaccat cacgattacg atatcccaac gaccgaaaac      60

ctgtattttc agggatccgg tagtggaagc atgcagattt tcgtgagaac ccttacgggg     120

aggaccatca ccctcgaagt tgaaccctcg gatacgatag aaaatgtaag ggccagaatc     180

caggataggg aaggaatacc tcctgatcag cagagactga tctttgctgg caggcagctg     240

gaagatggac gtactttgtc tgactacaat attcaaaggg agtctactct tcatcttgtg     300

ttgagacttc gtggtggtga attcgccgcg gtagcgctgc tcccggcggt cctgctggcc     360

ttgctggcgc ccgaaacatt ttcagaccta tggaaactac ttcctgaaaa caagcttatg     420

gccgagcctt gggggaacga gttggcgtcc gcagctgcca ggggggacct agagcaactt     480

actagtttgt tgcaaaataa tgtaaacgtc aatgcacaaa atggatttgg aaggactgcg     540

ctgcaggtta tgaaacttgg aaatcccgag attgccagga gactgctact tagaggtgct     600

aatcccgatt tgaaagaccg aactggtaat gctgtcattc atgatgcggc cagagcaggt     660

ttcctggaca ctttacagac tttgctggag tttcaagctg atgttaacat cgaggataat     720

gaagggaacc tgcccttgca cttggctgcc aaagaaggcc acctccgggt ggtggagttc     780

ctggtgaagc acacggccag caatgtgggg catcggaacc ataaggggga caccgcctgt     840

gatttggcca ggctctatgg gaggaatgag gttgttagcc tgatgcaggc aaacggggct     900

gggggagcca caaatcttca aaaaaagaag agaaagggtg gaggtagtga tatctgtctg     960

cctcgttggg gttgtctgtg ggaagattaa ctcgagcacc accaccacca ccactg        1016
```

<210> SEQ ID NO 90
<211> LENGTH: 295
<212> TYPE: PRT
<213> ORGANISM: Artificial Sequence
<220> FEATURE:
<223> OTHER INFORMATION: Synthetic

<400> SEQUENCE: 90

```
Met Arg Gly Ser His His His His His His Asp Tyr Asp Ile Pro Thr
1               5                   10                  15

Thr Glu Asn Leu Tyr Phe Gln Gly Ser Gly Ser Gly Ser Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Glu Phe Glu Thr Phe Ser Asp
            100                 105                 110

Leu Trp Lys Leu Leu Pro Glu Asn Lys Leu Met Ala Glu Pro Trp Gly
        115                 120                 125

Asn Glu Leu Ala Ser Ala Ala Ala Arg Gly Asp Leu Glu Gln Leu Thr
    130                 135                 140

Ser Leu Leu Gln Asn Asn Val Asn Val Asn Ala Gln Asn Gly Phe Gly
145                 150                 155                 160

Arg Thr Ala Leu Gln Val Met Lys Leu Gly Asn Pro Glu Ile Ala Arg
                165                 170                 175

Arg Leu Leu Leu Arg Gly Ala Asn Pro Asp Leu Lys Asp Arg Thr Gly
            180                 185                 190

Asn Ala Val Ile His Asp Ala Ala Arg Ala Gly Phe Leu Asp Thr Leu
        195                 200                 205

Gln Thr Leu Leu Glu Phe Gln Ala Asp Val Asn Ile Glu Asp Asn Glu
    210                 215                 220

Gly Asn Leu Pro Leu His Leu Ala Ala Lys Glu Gly His Leu Arg Val
225                 230                 235                 240

Val Glu Phe Leu Val Lys His Thr Ala Ser Asn Val Gly His Arg Asn
                245                 250                 255

His Lys Gly Asp Thr Ala Cys Asp Leu Ala Arg Leu Tyr Gly Arg Asn
            260                 265                 270

Glu Val Val Ser Leu Met Gln Ala Asn Gly Ala Gly Gly Ala Thr Asn
        275                 280                 285

Leu Gln Lys Lys Lys Arg Lys
    290                 295
```

<210> SEQ ID NO 91
<211> LENGTH: 917
<212> TYPE: DNA
<213> ORGANISM: Artificial Sequence
<220> FEATURE:
<223> OTHER INFORMATION: Synthetic

<400> SEQUENCE: 91

```
catatgagag gatcgcatca ccatcaccat cacgattacg atatcccaac gaccgaaaac     60

ctgtattttc agggatccgg tagtggaagc atgcagattt tcgtgagaac ccttacgggg    120
```

```
aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctga attcgaaaca ttttcagacc tatggaaact acttcctgaa    360

aacaagctta tggccgagcc ttgggggaac gagttggcgt ccgcagctgc caggggggac    420

ctagagcaac ttactagttt gttgcaaaat aatgtaaacg tcaatgcaca aaatggattt    480

ggaaggactg cgctgcaggt tatgaaactt ggaaatcccg agattgccag gagactgcta    540

cttagaggtg ctaatcccga tttgaaagac cgaactggta atgctgtcat tcatgatgcg    600

gccagagcag gtttcctgga cactttacag actttgctgg agtttcaagc tgatgttaac    660

atcgaggata atgaagggaa cctgcccttg cacttggctg ccaaagaagg ccacctccgg    720

gtggtggagt tcctggtgaa gcacacggcc agcaatgtgg ggcatcggaa ccataagggg    780

gacaccgcct gtgatttggc caggctctat gggaggaatg aggttgttag cctgatgcag    840

gcaaacgggg ctgggggagc cacaaatctt caaaaaaaga agagaaagta actcgagcac    900

caccaccacc accactg                                                   917
```

<210> SEQ ID NO 92
<211> LENGTH: 312
<212> TYPE: PRT
<213> ORGANISM: Artificial Sequence
<220> FEATURE:
<223> OTHER INFORMATION: Synthetic

<400> SEQUENCE: 92

```
Met Arg Gly Ser His His His His His His Asp Tyr Asp Ile Pro Thr
1               5                   10                  15

Thr Glu Asn Leu Tyr Phe Gln Gly Ser Gly Ser Gly Ser Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Ala Glu Phe Glu Thr Phe Ser Asp
            100                 105                 110

Leu Trp Lys Leu Leu Pro Glu Asn Lys Leu Met Ala Glu Pro Trp Gly
        115                 120                 125

Asn Glu Leu Ala Ser Ala Ala Ala Arg Gly Asp Leu Glu Gln Leu Thr
    130                 135                 140

Ser Leu Leu Gln Asn Asn Val Asn Val Asn Ala Gln Asn Gly Phe Gly
145                 150                 155                 160

Arg Thr Ala Leu Gln Val Met Lys Leu Gly Asn Pro Glu Ile Ala Arg
                165                 170                 175

Arg Leu Leu Leu Arg Gly Ala Asn Pro Asp Leu Lys Asp Arg Thr Gly
            180                 185                 190

Asn Ala Val Ile His Asp Ala Ala Arg Ala Gly Phe Leu Asp Thr Leu
        195                 200                 205

Gln Thr Leu Leu Glu Phe Gln Ala Asp Val Asn Ile Glu Asp Asn Glu
```

```
    210                 215                 220

Gly Asn Leu Pro Leu His Leu Ala Ala Lys Glu Gly His Leu Arg Val
225                 230                 235                 240

Val Glu Phe Leu Val Lys His Thr Ala Ser Asn Val Gly His Arg Asn
                245                 250                 255

His Lys Gly Asp Thr Ala Cys Asp Leu Ala Arg Leu Tyr Gly Arg Asn
            260                 265                 270

Glu Val Val Ser Leu Met Gln Ala Asn Gly Ala Gly Gly Ala Thr Asn
        275                 280                 285

Leu Gln Lys Lys Lys Arg Lys Gly Gly Gly Ser Asp Ile Cys Leu Pro
    290                 295                 300

Arg Trp Gly Cys Leu Trp Glu Asp
305                 310


<210> SEQ ID NO 93
<211> LENGTH: 968
<212> TYPE: DNA
<213> ORGANISM: Artificial Sequence
<220> FEATURE:
<223> OTHER INFORMATION: Synthetic

<400> SEQUENCE: 93

catatgagag gatcgcatca ccatcaccat cacgattacg atatcccaac gaccgaaaac     60

ctgtattttc agggatccgg tagtggaagc atgcagattt tcgtgagaac ccttacgggg    120

aggaccatca ccctcgaagt tgaaccctcg gatacgatag aaaatgtaag ggccagaatc    180

caggataggg aaggaatacc tcctgatcag cagagactga tctttgctgg caggcagctg    240

gaagatggac gtactttgtc tgactacaat attcaaaggg agtctactct tcatcttgtg    300

ttgagacttc gtggtgctga attcgaaaca ttttcagacc tatggaaact acttcctgaa    360

aacaagctta tggccgagcc ttgggggaac gagttggcgt ccgcagctgc caggggggac    420

ctagagcaac ttactagttt gttgcaaaat aatgtaaacg tcaatgcaca aaatggattt    480

ggaaggactg cgctgcaggt tatgaaactt ggaaatcccg agattgccag gagactgcta    540

cttagaggtg ctaatcccga tttgaaagac cgaactggta atgctgtcat tcatgatgcg    600

gccagagcag gtttcctgga cactttacag actttgctgg agtttcaagc tgatgttaac    660

atcgaggata atgaagggaa cctgcccttg cacttggctg ccaaagaagg ccacctccgg    720

gtggtggagt tcctggtgaa gcacacggcc agcaatgtgg ggcatcggaa ccataagggg    780

gacaccgcct gtgatttggc caggctctat gggaggaatg aggttgttag cctgatgcag    840

gcaaacgggg ctgggggagc cacaaatctt caaaaaaaga agagaaaggg tggaggtagt    900

gatatctgtc tgcctcgttg ggttgtctg tgggaagatt aactcgagca ccaccaccac    960

caccactg                                                              968


<210> SEQ ID NO 94
<211> LENGTH: 295
<212> TYPE: PRT
<213> ORGANISM: Artificial Sequence
<220> FEATURE:
<223> OTHER INFORMATION: Synthetic

<400> SEQUENCE: 94

Met Arg Gly Ser His His His His His His Asp Tyr Asp Ile Pro Thr
1               5                   10                  15

Thr Glu Asn Leu Tyr Phe Gln Gly Ser Gly Ser Gly Ser Met Gln Ile
            20                  25                  30
```

```
Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Gly Glu Phe Glu Thr Phe Ser Asp
            100                 105                 110

Leu Trp Lys Leu Leu Pro Glu Asn Lys Leu Met Ala Glu Pro Trp Gly
        115                 120                 125

Asn Glu Leu Ala Ser Ala Ala Ala Arg Gly Asp Leu Glu Gln Leu Thr
    130                 135                 140

Ser Leu Leu Gln Asn Asn Val Asn Val Asn Ala Gln Asn Gly Phe Gly
145                 150                 155                 160

Arg Thr Ala Leu Gln Val Met Lys Leu Gly Asn Pro Glu Ile Ala Arg
                165                 170                 175

Arg Leu Leu Leu Arg Gly Ala Asn Pro Asp Leu Lys Asp Arg Thr Gly
            180                 185                 190

Asn Ala Val Ile His Asp Ala Ala Arg Ala Gly Phe Leu Asp Thr Leu
        195                 200                 205

Gln Thr Leu Leu Glu Phe Gln Ala Asp Val Asn Ile Glu Asp Asn Glu
    210                 215                 220

Gly Asn Leu Pro Leu His Leu Ala Ala Lys Glu Gly His Leu Arg Val
225                 230                 235                 240

Val Glu Phe Leu Val Lys His Thr Ala Ser Asn Val Gly His Arg Asn
                245                 250                 255

His Lys Gly Asp Thr Ala Cys Asp Leu Ala Arg Leu Tyr Gly Arg Asn
            260                 265                 270

Glu Val Val Ser Leu Met Gln Ala Asn Gly Ala Gly Gly Ala Thr Asn
        275                 280                 285

Leu Gln Lys Lys Lys Arg Lys
    290                 295
```

<210> SEQ ID NO 95
<211> LENGTH: 917
<212> TYPE: DNA
<213> ORGANISM: Artificial Sequence
<220> FEATURE:
<223> OTHER INFORMATION: Synthetic

<400> SEQUENCE: 95

```
catatgagag gatcgcatca ccatcaccat cacgattacg atatcccaac gaccgaaaac      60

ctgtattttc agggatccgg tagtggaagc atgcagattt tcgtgagaac ccttacgggg     120

aggaccatca ccctcgaagt tgaaccctcg gatacgatag aaaatgtaag ggccagaatc     180

caggataggg aaggaatacc tcctgatcag cagagactga tctttgctgg caggcagctg     240

gaagatggac gtactttgtc tgactacaat attcaaaggg agtctactct tcatcttgtg     300

ttgagacttc gtggtggtga attcgaaaca ttttcagacc tatggaaact acttcctgaa     360

aacaagctta tggccgagcc ttgggggaac gagttggcgt ccgcagctgc caggggggac     420

ctagagcaac ttactagttt gttgcaaaat aatgtaaacg tcaatgcaca aaatggattt     480

ggaaggactg cgctgcaggt tatgaaactt ggaaatcccg agattgccag gagactgcta     540
```

```
cttagaggtg ctaatcccga tttgaaagac cgaactggta atgctgtcat tcatgatgcg    600

gccagagcag gtttcctgga cactttacag actttgctgg agtttcaagc tgatgttaac    660

atcgaggata atgaagggaa cctgcccttg cacttggctg ccaaagaagg ccacctccgg    720

gtggtggagt tcctggtgaa gcacacggcc agcaatgtgg ggcatcggaa ccataagggg    780

gacaccgcct gtgatttggc caggctctat gggaggaatg aggttgttag cctgatgcag    840

gcaaacgggg ctgggggagc cacaaatctt caaaaaaaga agagaaagta actcgagcac    900

caccaccacc accactg                                                   917
```

<210> SEQ ID NO 96
<211> LENGTH: 312
<212> TYPE: PRT
<213> ORGANISM: Artificial Sequence
<220> FEATURE:
<223> OTHER INFORMATION: Synthetic

<400> SEQUENCE: 96

```
Met Arg Gly Ser His His His His His His Asp Tyr Asp Ile Pro Thr
1               5                   10                  15

Thr Glu Asn Leu Tyr Phe Gln Gly Ser Gly Ser Gly Ser Met Gln Ile
            20                  25                  30

Phe Val Arg Thr Leu Thr Gly Arg Thr Ile Thr Leu Glu Val Glu Pro
        35                  40                  45

Ser Asp Thr Ile Glu Asn Val Arg Ala Arg Ile Gln Asp Arg Glu Gly
    50                  55                  60

Ile Pro Pro Asp Gln Gln Arg Leu Ile Phe Ala Gly Arg Gln Leu Glu
65                  70                  75                  80

Asp Gly Arg Thr Leu Ser Asp Tyr Asn Ile Gln Arg Glu Ser Thr Leu
                85                  90                  95

His Leu Val Leu Arg Leu Arg Gly Gly Glu Phe Glu Thr Phe Ser Asp
            100                 105                 110

Leu Trp Lys Leu Leu Pro Glu Asn Lys Leu Met Ala Glu Pro Trp Gly
        115                 120                 125

Asn Glu Leu Ala Ser Ala Ala Ala Arg Gly Asp Leu Glu Gln Leu Thr
    130                 135                 140

Ser Leu Leu Gln Asn Asn Val Asn Val Asn Ala Gln Asn Gly Phe Gly
145                 150                 155                 160

Arg Thr Ala Leu Gln Val Met Lys Leu Gly Asn Pro Glu Ile Ala Arg
                165                 170                 175

Arg Leu Leu Leu Arg Gly Ala Asn Pro Asp Leu Lys Asp Arg Thr Gly
            180                 185                 190

Asn Ala Val Ile His Asp Ala Ala Arg Ala Gly Phe Leu Asp Thr Leu
        195                 200                 205

Gln Thr Leu Leu Glu Phe Gln Ala Asp Val Asn Ile Glu Asp Asn Glu
    210                 215                 220

Gly Asn Leu Pro Leu His Leu Ala Ala Lys Glu Gly His Leu Arg Val
225                 230                 235                 240

Val Glu Phe Leu Val Lys His Thr Ala Ser Asn Val Gly His Arg Asn
                245                 250                 255

His Lys Gly Asp Thr Ala Cys Asp Leu Ala Arg Leu Tyr Gly Arg Asn
            260                 265                 270

Glu Val Val Ser Leu Met Gln Ala Asn Gly Ala Gly Gly Ala Thr Asn
        275                 280                 285
```

```
Leu Gln Lys Lys Lys Arg Lys Gly Gly Gly Ser Asp Ile Cys Leu Pro
    290                 295                 300

Arg Trp Gly Cys Leu Trp Glu Asp
305                 310


<210> SEQ ID NO 97
<211> LENGTH: 968
<212> TYPE: DNA
<213> ORGANISM: Artificial Sequence
<220> FEATURE:
<223> OTHER INFORMATION: Synthetic

<400> SEQUENCE: 97

catatgagag gatcgcatca ccatcaccat cacgattacg atatcccaac gaccgaaaac      60

ctgtattttc agggatccgg tagtggaagc atgcagattt tcgtgagaac ccttacgggg     120

aggaccatca ccctcgaagt tgaaccctcg gatacgatag aaaatgtaag ggccagaatc     180

caggataggg aaggaatacc tcctgatcag cagagactga tctttgctgg caggcagctg     240

gaagatggac gtactttgtc tgactacaat attcaaaggg agtctactct tcatcttgtg     300

ttgagacttc gtggtggtga attcgaaaca ttttcagacc tatggaaact acttcctgaa     360

aacaagctta tggccgagcc ttgggggaac gagttggcgt ccgcagctgc caggggggac     420

ctagagcaac ttactagttt gttgcaaaat aatgtaaacg tcaatgcaca aaatggattt     480

ggaaggactg cgctgcaggt tatgaaactt ggaaatcccg agattgccag gagactgcta     540

cttagaggtg ctaatcccga tttgaaagac cgaactggta atgctgtcat tcatgatgcg     600

gccagagcag gtttcctgga cactttacag actttgctgg agtttcaagc tgatgttaac     660

atcgaggata atgaagggaa cctgcccttg cacttggctg ccaaagaagg ccacctccgg     720

gtggtggagt tcctggtgaa gcacacggcc agcaatgtgg ggcatcggaa ccataagggg     780

gacaccgcct gtgatttggc caggctctat gggaggaatg aggttgttag cctgatgcag     840

gcaaacgggg ctgggggagc cacaaatctt caaaaaaaga agagaaaggg tggaggtagt     900

gatatctgtc tgcctcgttg ggttgtctg tgggaagatt aactcgagca ccaccaccac      960

caccactg                                                              968


<210> SEQ ID NO 98
<211> LENGTH: 15
<212> TYPE: PRT
<213> ORGANISM: Artificial Sequence
<220> FEATURE:
<223> OTHER INFORMATION: Synthetic

<400> SEQUENCE: 98

Val Thr Val Leu Ala Leu Gly Ala Leu Ala Gly Val Gly Val Gly
1               5                   10                  15


<210> SEQ ID NO 99
<211> LENGTH: 11
<212> TYPE: PRT
<213> ORGANISM: Artificial Sequence
<220> FEATURE:
<223> OTHER INFORMATION: Synthetic

<400> SEQUENCE: 99

Tyr Gly Arg Lys Lys Arg Arg Gln Arg Arg Arg
1               5                   10


<210> SEQ ID NO 100
<211> LENGTH: 11
```

-continued

```
<212> TYPE: PRT
<213> ORGANISM: Artificial Sequence
<220> FEATURE:
<223> OTHER INFORMATION: Synthetic

<400> SEQUENCE: 100

Tyr Ala Arg Val Arg Arg Arg Gly Pro Arg Arg
1               5                   10


<210> SEQ ID NO 101
<211> LENGTH: 11
<212> TYPE: PRT
<213> ORGANISM: Artificial Sequence
<220> FEATURE:
<223> OTHER INFORMATION: Synthetic

<400> SEQUENCE: 101

Arg Arg Arg Arg Arg Arg Arg Arg Arg Arg Arg
1               5                   10


<210> SEQ ID NO 102
<211> LENGTH: 21
<212> TYPE: PRT
<213> ORGANISM: Artificial Sequence
<220> FEATURE:
<223> OTHER INFORMATION: Synthetic

<400> SEQUENCE: 102

Lys Glu Thr Trp Trp Glu Thr Trp Trp Thr Glu Trp Ser Gln Pro Lys
1               5                   10                  15

Lys Lys Arg Lys Val
            20


<210> SEQ ID NO 103
<211> LENGTH: 16
<212> TYPE: PRT
<213> ORGANISM: Artificial Sequence
<220> FEATURE:
<223> OTHER INFORMATION: Synthetic

<400> SEQUENCE: 103

Arg Gln Ile Lys Ile Trp Phe Gln Asn Arg Arg Met Lys Trp Lys Lys
1               5                   10                  15
```

PROTEIN COMPLEX FOR INTRACELLULAR DELIVERY AND USES THEREOF

CROSS-REFERENCE TO RELATED APPLICATIONS

This application claims the benefit of Korean Patent Application No. 10-2011-0081160, filed on Aug. 16, 2011 in the Korean Intellectual Property Office, the disclosures of which are incorporated herein in their entirety by reference.

INCORPORATION BY REFERENCE OF MATERIAL ELECTRONICALLY FILED

Incorporated by reference in its entirety herein is a computer-readable nucleotide/amino acid sequence listing submitted concurrently herewith and identified as follows: One 206,551 byte ASCII (Text) file named "2ndReplacement710893_ST25.txt", created on Jan. 21, 2013.

BACKGROUND

1. Field

The present disclosure relates to protein complexes for intracellular delivery and uses thereof.

2. Description of the Related Art

Many human diseases develop due to abnormal activities of intracellular proteins. Accordingly, number of efforts has been made to develop novel medicines for treating various human diseases by controlling the abnormal activities of such intracellular proteins over the world. In particular, peptide, peptidergic material or protein-type material based on an enzyme-protein or protein-protein interaction that specifically controls biological activities have been rapidly developed. Although a peptide, a polypeptide, and a protein have much better physiological selectivity and efficacy than any other compounds, they cannot easily pass through a cell membrane due to their sizes and biochemical characteristics. Thus, they are not practically used as an effective therapeutic agent and a study material.

Also, control of biological activity by delivering a macromolecule, such as DNA, RNA, protein, oligonucleotide, and peptide, to a cell is very limited due to a cell membrane that constitutes a non-permeable barrier to these molecules. Biologically active macromolecules have very low delivery efficiency into tissues or cells, lack cell-specific targeting ability, and in many cases, decompose in vivo. Due to such obstacles, it is difficult to realize the efficacy of biologically active macromolecules.

Thus, many efforts such as developing various intracellular delivery platforms have been made. For example, recently developed delivery systems using short peptides have been studied. These peptides are cell-permeable and easy to introduce into cells, which characteristics have attracted the attention of researchers. However, the development of a system using delivery peptides has been at a standstill due to lack of commercial-level manufacture, in vitro and in vivo stability issues, and other such obstacles.

Accordingly, even with the availability of such conventional techniques, there remains a need for new compositions and methods for intracellular delivery of biologically active molecules.

SUMMARY

Provided are protein complexes for intracellular delivery, the protein complexes including an in vitro stabilization protein, a membrane translocation sequence domain, a biologically active molecule, and an in vivo stabilization protein.

Also, provided are methods of delivering a biologically active molecule into a cell by using the protein complex, a method for preparing a protein complex, and related methods and compositions.

BRIEF DESCRIPTION OF THE DRAWINGS

These and/or other aspects will become apparent and more readily appreciated from the following description of the embodiments, taken in conjunction with the accompanying drawings in which:

In FIG. 2A, protein complex #12-1 is Ub7KR(G76A)-MTS-NLS-SABP; protein complex #12-5 is Ub7KR(G76A)-MTS-p53-NLS-SABP; protein complex #12-6 is Ub7KR(G76A)-p53-NLS-SABP; protein complex #12-7 is Ub7KR(G76A)-MTS-p18-NLS-SABP; and protein complex #12-8 is Ub7KR (G76A)-p18-NLS-SABP. In FIG. 2B, protein complex #44 is Ub7KR(G76A)-MTS-p53-p18-NLS; protein complex #52 is Ub7KR (G76A)-MTS-p53-18-NLS-SABP; protein complex #54 is Ub7KR-MTS-p53-p18-NLS-SABP; protein complex #66 is Ub7KR(G76A)-p53-p18-NLS; protein complex #56 is Ub7KR(G76A)-p53-p18-NLS-SABP; and protein complex #57 is Ub7KR-p53-p18-NLS. M refers to a size marker;

DETAILED DESCRIPTION

Figure 1:
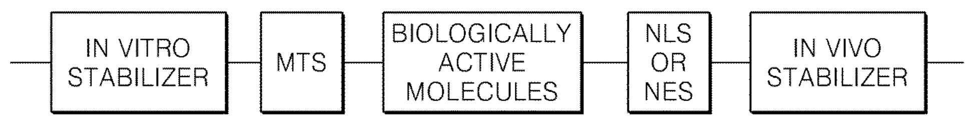
FIG. 1 is a schematic view of a protein complex for intracellular delivery.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

An aspect of the present invention provides a protein complex for cell delivery, including an in vitro stabilization protein, a membrane translocation sequence domain, a biologically active molecule, and an in vivo stabilization protein.

The protein complex for cell delivery may include an in vitro stabilization protein.

The term "in vitro stabilization protein" used herein refers to a protein for increasing solubility and stability of the protein complex when the protein complex is experimentally purified in vitro. In other words, the in vitro stabilization protein can be any protein that, when complexed with or otherwise attached to a cargo molecule (e.g., any of the biologically active molecules described herein) fused with a hydrophobic cell penetrating peptide (CPP) or membrane translocation sequence domain (MTS), provides a complex with increased water solubility as compared to the cargo molecule fused to the CPP/MTS without the in vitro stabilization protein. The in vitro stabilization protein is part of the protein complex and does not induce immunogenicity in vivo.

According to an embodiment of the present invention, the in vitro stabilization protein may be a ubiquitin (Ub), a Ub-like protein, an ankyrin repeat motif-including protein, or a transferrin protein.

Ub is the most conserved protein in nature that consists of 76 amino acids (SEQ ID No. 19), shows complete homogeny among evolutionarily various species including insects, trout, and humans, and is water-soluble. Also, Ub is known as a protein that has stability with respect to pH change, is not easily denatured even at high temperature, and has stability with respect to a protease. An ankyrin repeat motif is a 33-residue motif in proteins consisting of two alpha helices separated by loops. The ankyrin repeat motif mediates protein-protein interactions and is among the most common structural motif in known proteins. Transferrins are iron-binding glycoproteins that control the level of free iron in biological fluids. The Ub, Ub-like protein, the ankyrin repeat motif-including protein, or the transferrin protein may improve insolubility of the protein complex.

The Ub or Ub-like protein may be at least one selected from the group consisting of wild-type Ub, wild-type Ub-like protein, mutant Ub, and mutant Ub-like protein. In an embodiment, the wild-type Ub may have an amino acid sequence with SEQ ID No. 19. The mutant Ub refers to that an amino acid sequence of the wild-type Ub is substituted with another amino acid sequence. Examples of the mutant Ub are Ub formed by substituting Lys of a wild-type Ub with Arg, and Ub formed by substituting RGG at the C-terminus of a wild-type Ub with RGA. According to an embodiment of the present invention, in a mutant-type Ub formed by substituting Lys of a wild-type Ub with Arg, the substitution may occur with at least one Lys present at locations 6, 11, 27, 29, 33, 48 and/or 63 of the wild-type Ub with SEQ ID No. 19, and the substitution may occur in the Lys positions independently or in combination. According to an embodiment of the present invention, the mutant-type Ub may be a mutant Ub obtained by substituting Gly at location 76 in a wild-type Ub polypeptide with another amino acid, for example, with alanine (Ala).

According to an embodiment of the present invention, the Ub-like protein is a protein that has characteristics (e.g., stability characteristics) similar to those of Ub, and, for example, may be Nedd8 (e.g., UniProtKB/Swiss-Prot: Q15843), SUMO-1 (e.g., UniProtKB/Swiss-Prot: P63165), SUMO-2 (e.g., UniProtKB/Swiss-Prot: P61956), NUB1 (e.g., UniProtKB/Swiss-Prot: Q9Y5A7), PIC1, UBL3 (e.g., UniProtKB/Swiss-Prot: O95164), UBL5 (e.g., UniProtKB/Swiss-Prot: Q9BZL1), or ISG15 (e.g., UniProtKB/Swiss-Prot: P05161).

According to an embodiment of the present invention, an ankyrin repeat motif-including protein or a transferrin protein may be wild type or mutant type thereof. For example, mutant type of an ankyrin repeat motif-including protein or a transferrin protein may be wild type may be genetically engineered.

According to an embodiment of the present invention, the Ub, Ub-like protein, ankyrin repeat motif-including protein, or transferrin protein may include at its C-terminus an amino acid sequence that is cleavable by a protease, or an amino acid sequence that is not cleavable by a protease. The amino acid sequence that is cleavable by a protease may be obtained from data base known in the art. For example, proteases and amino acid sequences that are cleavable by the proteases can be determined using available tools, such as the PeptideCutter™ database maintained by the Swiss Institute of Bioinformatics, Quartier Sorge—Batiment Genopode, 1015 Lausanne, Switzerland. When the cleavable amino acid sequence is included, once the protein complex is transferred into a cell, the Ub, Ub-like protein, ankyrin repeat motif-including protein, or transferring protein is cleaved by an intracellular protease, thereby enabling the biologically active molecule to perform its intracellular function. Even after the cleavage, the biologically active molecule still includes a membrane translocation sequence domain. Since the length of a polypeptide of the membrane translocation sequence domain is very short, the membrane translocation sequence domain does not affect the function of the biologically active molecule. In embodiments where the Ub or Ub-like protein is not cleaved by the intracellular protease, the biologically active molecule is selected such that it will still perform its intracellular function.

The term "membrane transfer" used herein refers to a capability of delivering a biologically active molecule of a subject to be carried into a cell or nucleus in vitro and/or in vivo. Also, the term "membrane translocation sequence domain (MTS)" or "cell-penetrating peptide" used herein refers to a polypeptide having an amino acid sequence that is permeable through a cell membrane of a phospholipid bilayer (i.e., a polypeptide that will permeate a cell membrane, regardless of mechanism). In an embodiment, the membrane translocation sequence domain may have a single hydrophobic region at its N-terminal, form a helical structure, show flexibility, and/or have a relatively short amino acid sequence (e.g., about 7 to 17 amino acids). The membrane translocation sequence domain may have hydrophobic properties. According to an embodiment of the present invention, the membrane translocation sequence domain may be any one of various polypeptides that have amino acid sequences that are permeable through a cell membrane of a phospholipid bilayer. For example, the membrane translocation sequence domain may be selected from the group consisting of SEQ ID NO: 1 to SEQ ID NO: 15, or SEQ ID NOs: 98-103, or full length VP22 protein or N-terminal truncated VP22 comprising amino acids 159-301 of the full length protein.

The protein complex for intracellular delivery may include a biologically active molecule.

The term "biologically active molecule" used herein refers to a molecule that is linked to the membrane translocation sequence domain to be delivered into a cell and shows activity in vivo.

According to an embodiment of the present invention, the biologically active molecule may be selected from the group consisting of a nucleic acid molecule (for example, shRNA, siRNA, DNA, or the like), a chemical compound (for example, an anticancer drug, such as Taxol or the like), and a polypeptide.

According to an embodiment of the present invention, the biologically active molecule may be a polymer of amino acids that consist of two or more residuals and examples thereof are a polypeptide and a protein. The polypeptide may be, for example, a protein, such as SV40 large T antigen and telomerase, that is engaged in cell immortalization, an anti-apoptotic protein, such as mutant p53 and Bcl[−]xL, an antibody, an oncogene, such as ras, myc, HPV E6/E7, or adenovirus Ela, a cell cycle control protein, such as cyclin and cyclin-dependent kinase, a green fluorescence protein, or an enzyme, such as beta-galactosidase and chloramphenicol acetyl transferase.

The biologically active molecule is not limited to any particular physiochemical properties. For instance, the biologically active molecule may comprise a hydrophobic or a hydrophilic protein. Also, examples of the biologically active molecule are a hormone, a hormone analogue, an enzyme, an enzyme inhibitor, a signal transduction protein or a part thereof, an antibody or a part thereof, a single-chain antibody, a binding protein or a binding domain thereof, an antigen, an attachment protein, a structure protein, a regulatory protein, a toxoprotein, cytokine, a transcription factor, or a blood coagulation factor.

Also, the biologically active molecule may be p53, p18, a protein complex formed by linking p53 and p18 (p53-p18), p21, p25, p57, p16, p15, NIP71, neuroregulin 1, PTEN tumor suppressor, ARF tumor suppressor, APC, CD95, Folliculin, MEN1, BRCA1, Von Hippel-Lindau tumor suppressor, RKIP, nm23, endostatin, insulin, insulin-like growth factor 1 (IGF-1), growth hormone, erythropoietin, granulocyte-colony stimulating factors (G-CSFs), granulocyte/macrophage-colony stimulating factors (GM-CSFs), interferon alpha, interferon beta, interferon gamma, interleukin-1 alpha and beta, interleukin-3, interleukin-4, interleukin-6, interleukin-2, epidermal growth factors (EGFs), calcitonin, adrenocorticotropic hormone (ACTH), tumor necrosis factor (TNF), atobisban, buserelin, cetrorelix, deslorelin, desmopressin, dynorphin A (1-13), elcatonin, eleidosin, eptifibatide, growth hormone releasing hormone-II (GHRH-II), gonadorelin, goserelin, histrelin, leuprorelin, lypressin, octreotide, oxytocin, pitressin, secretin, sincalide, terlipressin, thymopentin, thymosine $\alpha 1$, triptorelin, bivalirudin, carbetocin, cyclosporine, exedine, lanreotide, luteinizing hormone-releasing hormone (LHRH), nafarelin, parathyroid hormone, pramlintide, enfuvirtide (T-20), thymalfasin, or ziconotide.

The protein complex for intracellular delivery may include an in vivo stabilization protein.

The term "in vivo stabilization protein" used herein refers to a protein that provides stability to the protein complex so that the protein complex stably exists in vivo where the protein complex substantially acts. The in vivo stabilization protein is part of the protein complex, and does not cause immunogenicity in vivo. The in vivo stabilization protein may be any one of various proteins that, when administered to a subject, confer stability to the complex when in the blood of a subject or other physiological environment, as appropriate for the desired end use. In other words, the in vivo stabilization protein can be any protein that, when complexed with, or otherwise attached to, a cargo molecule (e.g., any of the biologically active molecules described herein) fused with a hydrophobic cell penetrating peptide (CPP) or membrane translocation sequence domain (MTS), provides a complex with increased half life under physiological conditions (e.g., in blood or in the bloodstream of a subject) or increased resistance to renal clearance as compared to the cargo molecule fused to the CPP/MTS without the in vivo stabilization protein. According to an embodiment of the present invention, the in vivo stabilization protein may be a serum albumin binding peptide, a Fc region of antibody, or alpha antitrypsin (AAT) (e.g., GenBank Accession ABV21360.1 GI:157086955) or a fragment thereof sufficient to provide in vivo stabilization.

The protein complex for intracellular delivery may further include a nucleus-cytoplasm signal domain.

The term "nucleus-cytoplasm signal domain" used herein refers to a polypeptide sequence included in the protein complex for intracellular delivery which is to transfer the biologically active molecule into or from a nucleus. According to an embodiment of the present invention, the nucleus-cytoplasm signal domain may be a nucleus location sequence (NLS) domain or a nucleus export sequence (NES) domain. That is, NLS may be included in the protein complex for intracellular delivery to transfer the protein complex into a nucleus, and NES may be included in the protein complex for intracellular delivery to retain the biologically active molecule present in the cytoplasm.

An NLS domain is included in proteins that are transferred from cytoplasm to a nucleus, and an NES domain is included in proteins that are transferred from a nucleus to cytoplasm. The NES domain refers to a polypeptide having an amino acid sequence that is permeable through a nuclear membrane, and the amino acid sequence is not particularly limited. Non-limiting examples of the amino acid sequence of the NES domain are KKKRK (SEQ ID NO: 16), PKKKRKV (SEQ ID NO: 17), and KRPAATKKAGQAKKKK (SEQ ID NO: 18). Also, the nucleus-cytoplasm location domain may be located between the biologically active molecule and the in vivo stabilization protein in the protein complex for intracellular delivery. In this structure, the protein complex may have the maximum intracellular delivery efficiency.

In the protein complex, the nucleus-cytoplasm location domain may increase solubility of the protein complex. The closer the nucleus-cytoplasm location domain is located to the C-terminus of the protein complex, the solubility of the protein complex is further increased. When the nucleus-cytoplasm location domain has a basic property, it may be susceptible to a C-terminus peptidase. However, if the in vivo stabilization protein (for example, serum albumin or the like) is present, the in vivo stabilization protein may protect the nucleus-cytoplasm location domain from the C-terminus peptidase, thereby enabling the nucleus-cytoplasm location domain to retain its function.

The protein complex for intracellular delivery may include an in vitro stabilization protein, a membrane translocation sequence domain, a biologically active molecule, and an in vivo stabilization protein in any order. In some embodiments, the protein complex for intracellular delivery may include an in vitro stabilization protein, a membrane translocation sequence domain, a biologically active molecule, and an in vivo stabilization protein in sequence from an N-terminus thereof. The protein complex for intracellular delivery may include an in vitro stabilization protein, a membrane translocation sequence domain, a biologically active molecule, a nucleus-cytoplasm signal domain, and an in vivo stabilization protein in sequence from an N-terminus thereof.

The protein complex can comprise more than one in vitro stabilization protein, membrane translocation sequence domain, biologically active molecule, in vivo stabilization protein, and/or nucleus-cytoplasm signal domain, or the protein complex can comprise only one of each of these elements.

The elements of the protein complex may be part of a single amino acid polymer or protein. Furthermore, the elements of the protein complex may be joined by linker moieties. The linker moieties may comprise or consist of linking amino acid sequences. Any linker may be used, provided that it does not substantially interfere with the activity of the protein complex.

The protein complex may further include other elements needed or desired for the production, recovery, or use of the protein complex. For instance, the protein complex may comprise one or more tags to facilitate detection, isolation, and/or immobilization of the protein (e.g., fluorescent tags or affinity tags, such as a polyhistidine sequence). The protein complex may also include cleavable moieties or sequences to remove any such tags.

Also provided is a nucleic acid encoding a protein complex as described herein. The nucleic acid may comprise (i) a nucleotide sequence encoding an in vitro stabilization protein; (ii) a nucleotide sequence encoding a membrane translocation sequence domain; (iii) a nucleotide sequence encoding a biologically active molecule; and (iv) a nucleotide sequence encoding an in vivo stabilization protein. The nucleic acid may further comprising nucleic acid sequence(s) encoding one or more additional elements described herein with respect to the protein complex (e.g., a nucleus-cytoplasm signal domain).

The nucleic acid may be part of a vector (e.g., an expression vector). Any suitable expression vector may be used.

The nucleic acid and/or vector may further comprise and/or one or more non-coding (e.g., regulatory sequences, tags, restriction sites, etc.) as may be needed or desired for the expression or recovery of the protein complex, or other purpose.

The protein complex can be produced by any suitable method, for instance, by transforming a host cell with a nucleic acid encoding the protein complex. If the host cell is in vivo, the protein complex can be recovered (isolated) from the host cell and, optionally, purified to any degree necessary depending upon the intended end use. If the host cell is in vivo, the protein complex may be produced and have a biological effect in vivo. Alternatively, or in addition, the protein complex may be synthetically produced in whole or in part. An example of a method for producing a protein complex is described in the Examples provided herein.

Also provided herein is a composition comprising the protein complex or nucleic acid encoding the protein complex and a carrier. Any carrier suitable for storing or delivering the protein complex or nucleic acid, as applicable, may be used. The carrier can be any of those conventionally used and is limited only by physio-chemical considerations, such as solubility and lack of reactivity with the nucleic acid or protein complex, and by the intended end use or route of administration. The carriers may include any of a variety of well know vehicles, adjuvants, excipients, and diluents, particularly those which are pharmaceutically acceptable.

Another aspect of the present invention provides a method of intracellular protein delivery, the method including a protein complex-cell contact.

The method may allow a protein complex to come into contact with a cell, wherein the protein complex includes an in vitro stabilization protein; a membrane translocation sequence; a biologically active molecule; and an in vivo stabilization protein. The protein complex for cell delivery is as described above.

According to an embodiment of the present invention, the method may comprise administering the protein complex to a cell by contacting the cell with the protein complex or a nucleic acid encoding the protein complex, optionally in a vector, such that the cell expresses the protein complex. The contacting or other administration may be performed in vitro or in vivo. When administration or contacting is performed in vivo, the method may include administering the protein complex or nucleic acid encoding same to a subject (e.g., animal, particularly mammal, or human).

Furthermore, whether in vivo or in vitro, the cell may be in or part of a tissue, an organ, or other system. Also, for the administering, the protein complex or nucleic acid may be dissolved in an appropriate buffer solution and then the protein complex solution is directly brought into contact with a cell, a tissue, or an organ. Alternatively, the protein complex may be non-orally administered to a subject together with a pharmaceutically acceptable support. If the administering is a non-oral administration, intravenous infusion, subcutaneous infusion, intramuscular infusion, intraperitoneal infusion, endothelium administration, topical administration, intranasal administration, intrapulmonary administration, and intrarectal administration, or the like may be used. Because the administered protein complex includes the membrane translocation sequence domain, the biologically active molecule may be delivered to a cell corresponding to a body site where the administration methods are applied.

Hereinafter, one or more embodiments of the present invention will be described in detail. However, these examples are presented herein for illustrative purpose only and the present invention is not limited thereto.

EXAMPLE 1

Preparation of Expression Vector for Protein Complex

This experiment was performed to manufacture expression vectors for protein complexes for intracellular delivery and manufacture the protein complexes, wherein the protein complexes each included a Ub wild-type protein or Ub mutant-type protein, which are hydrophilic polypeptides, a membrane translocation sequence domain (MTS), p53-p18, a nucleus localization signal domain (NLS), and a serum albumin binding peptide (SABP) were linked in a combination as listed in the following table. Hereinafter, the wild-type Ub will be referred to as Ub7KR and a mutant-type Ub formed substituting Lys of the wild-type Ub with Arg and substituting RGG of the wild-type Ub C-terminus with RGA will be referred to as Ub7KR(G76A).

A total of 11 kinds of expression vectors were manufactured by Genotech Research Co., Ltd, and pET-21b(+) (Novagen) was used as a vector for over-expression of the protein complex. The general configuration of the protein complexes are provided in Table 1.

TABLE 1

| | Protein complex | | | | | | Amino |
|---|---|---|---|---|---|---|---|
| No. | Ub | MTS | Biologically active molecule | NLS | SABP | DNA (SEQ ID) | Acid (SEQ ID) |
| #12-1 | Ub7KR(G76A) | ○ | X | ○ | ○ | 20 | 54 |
| #12-5 | Ub7KR(G76A) | ○ | P53 | ○ | ○ | 21 | 58 |
| #12-6 | Ub7KR(G76A) | X | P53 | ○ | ○ | 22 | 59 |
| #12-7 | Ub7KR(G76A) | ○ | P18 | ○ | ○ | 23 | 60 |
| #12-8 | Ub7KR(G76A) | X | P18 | ○ | ○ | 24 | 61 |
| #44 | Ub7KR(G76A) | ○ | p53-p18 | ○ | X | 25, 83 | 82 |
| #52 | Ub7KR(G76A) | ○ | p53-p18 | ○ | ○ | 26, 85 | 84 |
| #53 | Ub7KR | ○ | p53-p18 | ○ | X | 87 | 86 |
| #54 | Ub7KR | ○ | p53-p18 | ○ | ○ | 27, 89 | 88 |
| #56 | Ub7KR(G76A) | X | p53-p18 | ○ | ○ | 28, 93 | 92 |

TABLE 1-continued

| | Protein complex | | | | | | Amino |
|---|---|---|---|---|---|---|---|
| No. | Ub | MTS | Biologically active molecule | NLS | SABP | DNA (SEQ ID) | Acid (SEQ ID) |
| #57 | Ub7KR | X | p53-p18 | ○ | X | 29, 95 | 94 |
| #58 | Ub7KR | X | p53-p18 | ○ | ○ | 97 | 96 |
| #66 | Ub7KR(G76A) | X | p53-p18 | ○ | X | 30, 91 | 90 |

"X" indicates moiety not present; "○" indicates moiety present.

Also, the respective insert DNA fragments may include a nucleotide sequence that is cleavable by NdeI at their 5' end and a nucleotide sequence that is cleavable by XhoI at their 3' end, and thus may be inserted into a NdeI-XhoI cleavage sequence of the pET21b(+) vector.

FIG. 1 shows a schematic view illustrating a primary structure of a protein complex for intracellular delivery (#52) according to an embodiment of the present invention.

EXAMPLE 2

Expression and Purification of Protein Complex

To over-express protein complex using each of 11 vectors prepared in Example 1, *E. coli* BL21 (DE3) transformed with each of vectors was used to express each of protein complexes. In this case, YT medium was used as a culture solution, and when an O.D. value was 0.5 at an absorption wavelength of 600 nm, 0.5 mM IPTG was added thereto and incubation was further performed at 18° C. for 16 hours. Cells obtained by the incubation were lysed by ultrasonic waves in buffer supplemented with 50 mM Tris-HCl pH8.0, 5% glycerol, 5 mM β-mercaptoethanol, 0.2% TRITON™ X-100, and 0.2 M NaCl, and then centrifuged using an centrifuger (10, 000×g) to clarify the cell lysate. The supernatant solution was applied to an $Ni^{2+}$-NTA superflow column (Qiagen) equilibrated in buffer, and then the result column was washed with five column volume (CV) of a washing buffer solution (50 mM Tris-HCl, pH 8.0, 5% glycerol, 5 mM β-mercaptoethanol, 0.2% TRITON™ X-100 and 1 M NaCl), followed by elution of bound protein with a buffer supplemented with 50 mM Tris-HCl, pH 8.0, 5% glycerol, 5 mM β-mercaptoethanol, 0.2% TRITON™ X-100 and 0.2 M NaCl. Fractions including the protein complexes were collected and a salt was removed therefrom using AMICON™ Ultra-15 Centrifugal Filter (Milipore), followed by concentration. The purified protein concentration was measured using bovine serum albumin (BSA) as a reference material.

Figure 2:
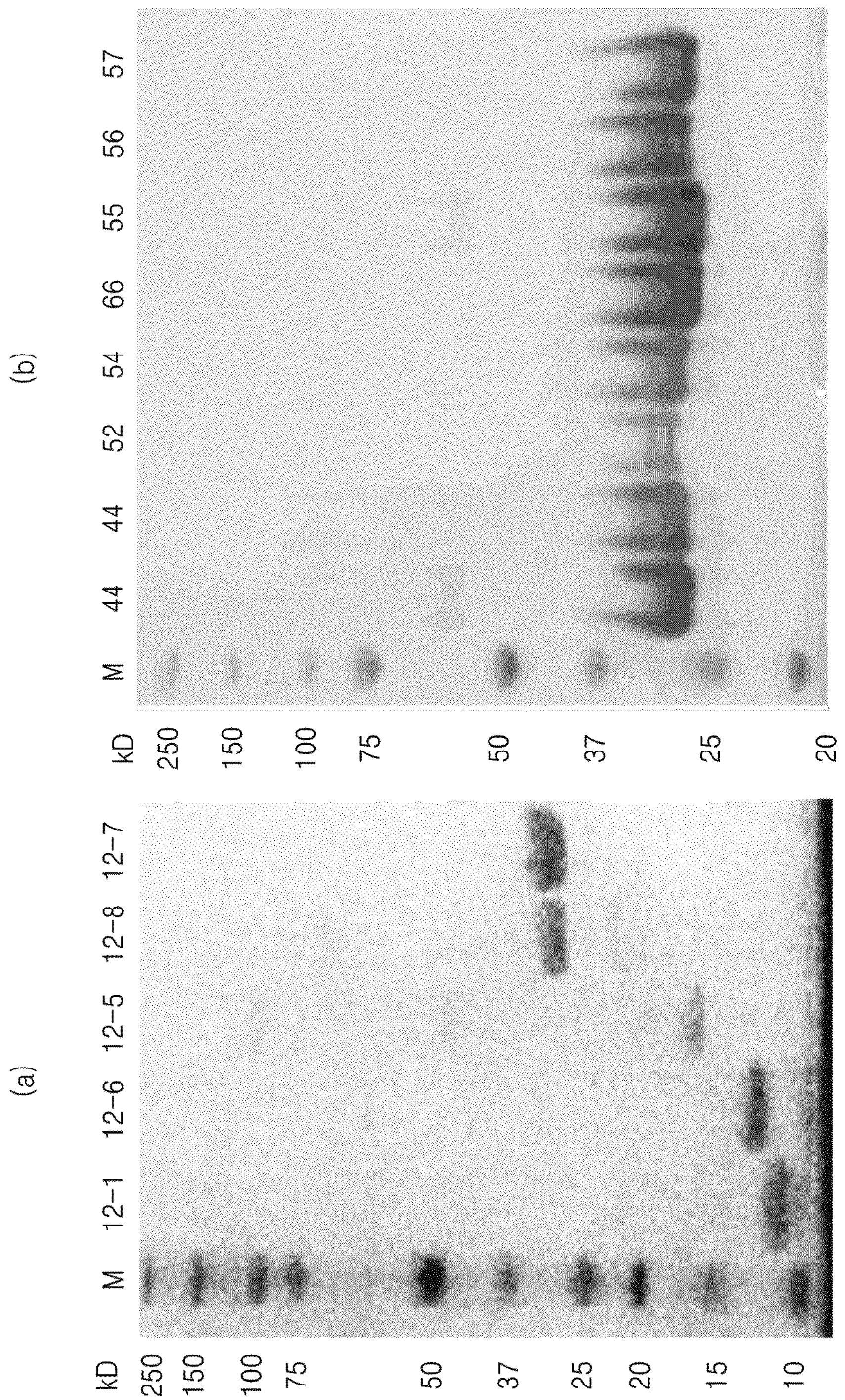
FIGS. 2A and 2B show sodium dodecyl sulfate polyacrylamide gel electrophoresis (SDS-PAGE) results of purified products of a protein complexes as described herein.

FIG. 2 shows SDS-PAGE results of the purified protein complexes expressed from the vectors prepared according to Example 1. In FIG. 2A, a protein complex #12-1 is a protein complex having a sequence of Ub7KR(G76A)-MTS-NLS-SABP, a protein complex #12-5 is a protein complex having a sequence of Ub7KR(G76A)-MTS-p53-NLS-SABP, a protein complex #12-6 is a protein complex having a sequence of Ub7KR(G76A)-p53-NLS-SABP, a protein complex #12-7 is a protein complex having a sequence of Ub7KR(G76A)-MTS-p18-NLS-SABP, and a protein complex #12-8 is a protein complex having a sequence of Ub7KR(G76A)-p18-NLS-SABP. In FIG. 2B, a protein complex #44 is a protein complex having a sequence of Ub7KR(G76A)-MTS-p53-p18-NLS, a protein complex #52 is a protein complex having a sequence of Ub7KR(G76A)-MTS-p53-p18-NLS-SABP, a protein complex #54 is a protein complex having a sequence of Ub7KR-MTS-p53-p18-NLS-SABP, a protein complex #66 is a protein complex having a sequence of Ub7KR (G76A)-p53-p18-NLS, a protein complex #56 is a protein complex having a sequence of Ub7KR(G76A)-p53-p18-NLS-SABP, and a protein complex #57 is a protein complex having a sequence of Ub7KR-p53-p18-NLS. M means a size marker.

EXAMPLE 3

Confirmation of in vivo Stability of Protein Complex including in vivo Stabilization Protein Whether the protein complexes prepared according to Example 2 stably exist in vivo was confirmed by identifying a binding between the protein complexes and serum albumin as a protein that exists in vivo.

First, from among the protein complexes purified according to Example 2, 500 ug of each of the #56 protein complex that includes SABP and the protein complex #66 that does not include SABP and 1500 ug of BSA were left in 1000 ul of a PBS buffer solution (1×PBS, 0.2% TWEEN™ 20, 100 mM arginine, 0.2% reduced glutathione) at 18° C. for 120 minutes to provide a sufficient binding time, and then, the reaction product was loaded to an HILOAD™ SUPERDEX™ S-75 16/60 column (GE healthcare), followed by elution. In this regard, elution conditions were a flow rate of 1 ml/min and a PBS buffer solution (1×PBS, 0.2% TWEEN™ 20, 100 mM arginine, 0.2% reduced glutathione). The elution was performed using 2 ml of each fraction for 120 minutes. Thereafter, the eluent was applied to an $Ni^{2+}$-NTA Superflow column (Qiagen) that had been equilibrated with a 50 mM Tris buffer solution (50 mM Tris-HCl, pH 8.0, 5% glycerol, 5 mM β-mercaptoethanol, 0.2% TRITON™ X-100 and 1 M NaCl), followed by elution using the same method as in Example 2 to complete the purification of the protein complexes.

Figure 3:
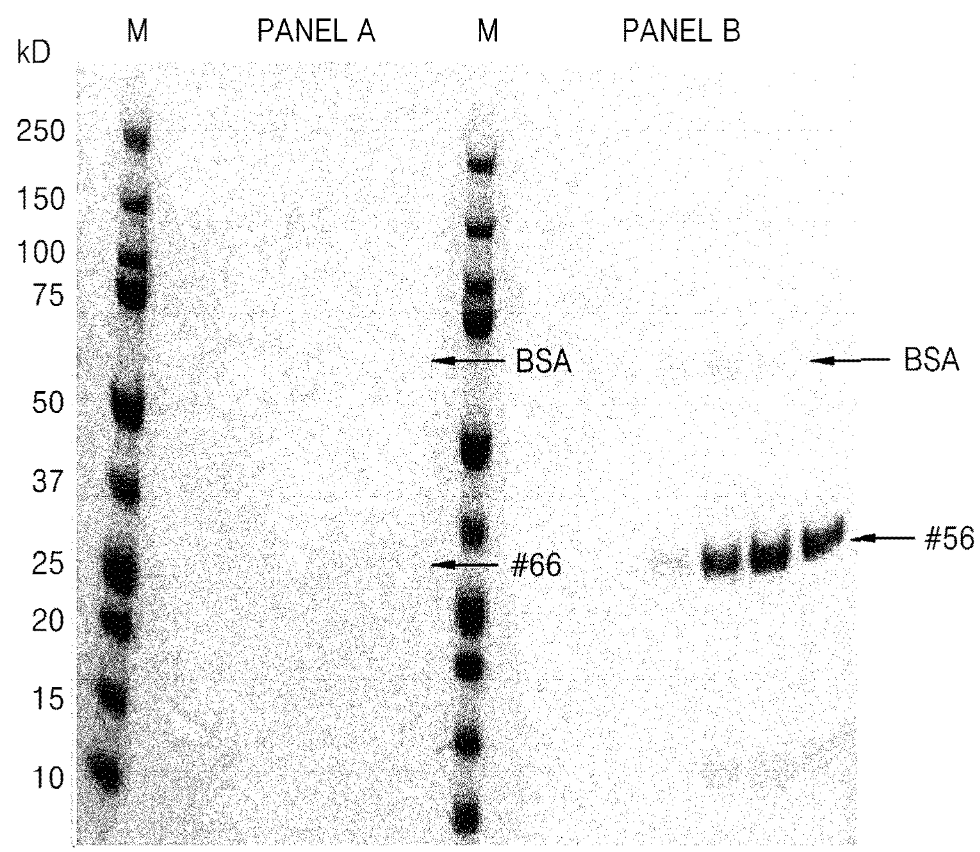
FIG. 3 shows SDS-PAGE results of serum albumin binding of a protein complex that does not include SABP (A panel), and of a protein complex that includes SABP (B panel)
Figure 4A:
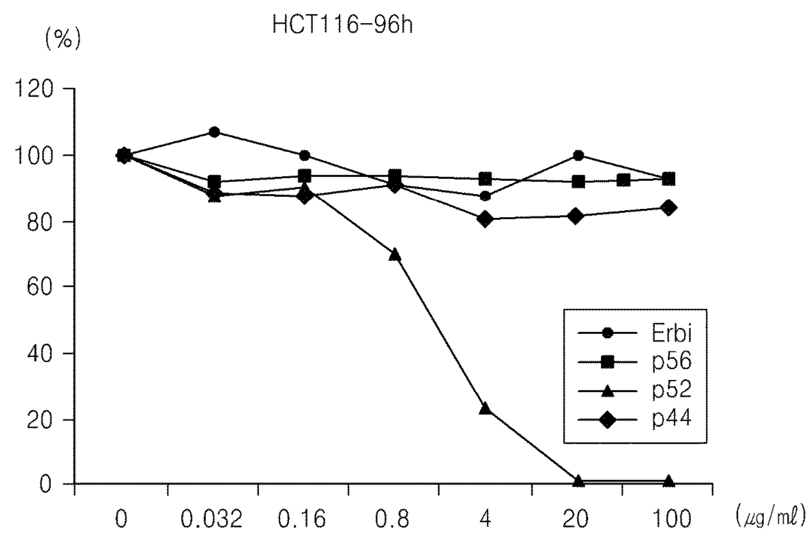
FIGS. 4A to 4E show cell growth suppression efficacy of a p53-p18 protein evaluated by administering a protein complex described herein to colorectal cancer cell lines [HCT116 (FIG. 4A), SW48 (FIG. 4B), LoVo (FIG. 4C) and LSI174T (FIG. 4D)) and a skin carcinoma cell line (A431 (FIG. 4E), Korean Cell Line Bank].
Figure 4B:
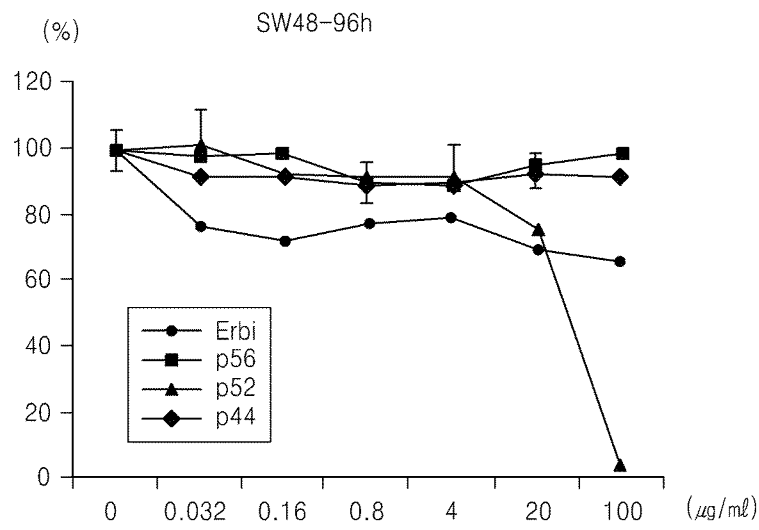
Figure 4C:
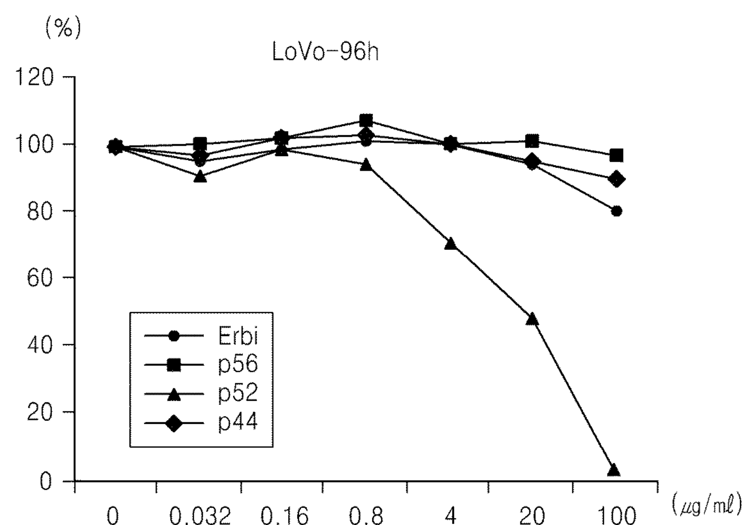
Figure 4D:
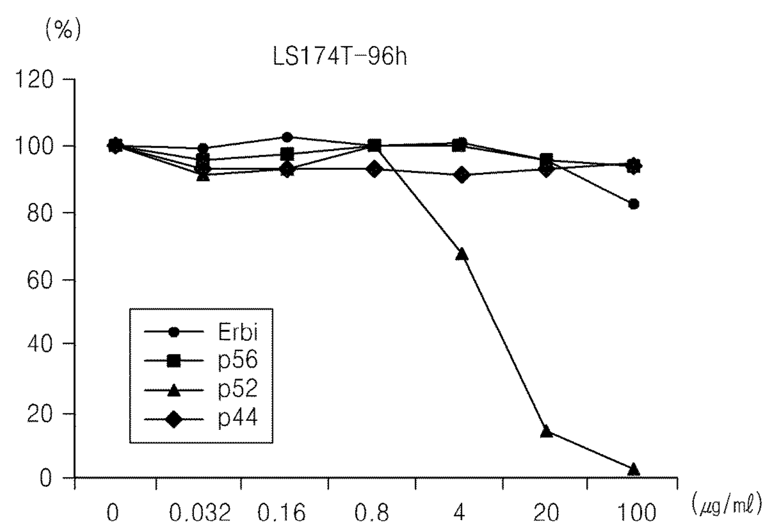
Figure 4E:
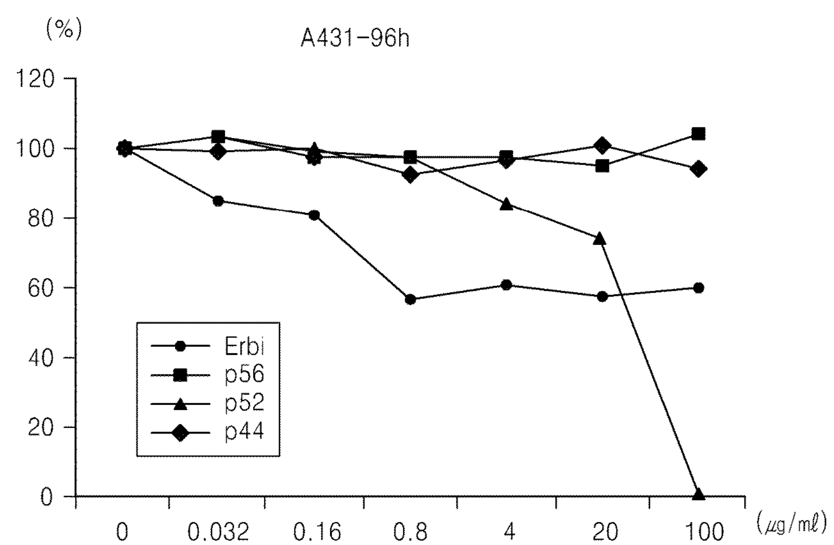

FIG. 3 shows SDS-PAGE results of the eluted protein complexes as described above. Referring to FIG. 3, it was confirmed that only the protein complex #56 including a serum albumin binding peptide binds to BSA. If the size of a protein complex is small, renal clearance may occur in vivo or the protein complex may be degraded by a protease. However, serum albumin is stable in blood and is not subjected to renal clearance. Thus, a protein complex that includes a serum albumin binding peptide is stable in vivo.

EXAMPLE 4

Confirmation on Anticancer Effect of Protein Complex by using Various Cancer Cell Lines The intracellular delivery and cancer cell therapeutic efficacy of the protein complexes prepared according to Example 2 were confirmed as follows: an anticancer effect of p53-p18 protein was confirmed by administering the protein complexes to colorectal cancer cell lines (HCT116, SW48, LoVo and LSI174T, Korean Cell Line Bank) and a skin carcinoma cell line (A431, Korean Cell Line Bank).

The respective cells were added to 10% FBS-including RPMI medium (Gibco BL) such that each well included $1 \times 10^4$ cells, and then treated with 0, 0.032, 0.16, 0.8, 4, 20, or 100 ug/ml of the protein complexes #56, #52 and #44 and incubated in a $CO_2$ incubator for 96 hours at 37° C. under a humidity of 85% and $CO_2$ of 5%. As a comparative example, ERBITUX™, an anti-cancer therapeutic antibody, was used instead of the protein complexes at the same concentrations and the treated cells were incubated under the same conditions. Also, as a control, cell lines that were not treated with the protein complexes or ERBITUX™ were used.

As a result, as shown in FIGS. 4A to 4E, it was confirmed that a protein complex including both the NLS and the in vivo SABP substantially suppressed cell growth of all the cell lines at a concentration of 20 ug/ml, and at 100 ug/ml, all of the cell lines were completely suppressed.

As described above, a protein complex for cell delivery and a method of delivering a biologically active molecule into a cell by using the protein complex, according to the one or more of the above embodiments of the present invention, enable an effective delivery of a biologically active molecule.

EXAMPLE 5

Illustrative Further Embodiments

Additional examples of protein complex constructs are provided in Tables 2 and 3.

The Examples of protein complexes described herein may contain elements other than those listed in the table, such as polyhistidine tags, TEV cleavage sites, and intervening linking sequences between the various elements.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated

TABLE 2

| | Protein complex | | | | | | Amino |
|---|---|---|---|---|---|---|---|
| No. | Ub | MTS | Biologically active molecule | NLS | SABP | DNA (SEQ ID) | Acid (SEQ ID) |
| #12-2 | Ub7KR(G76A) | X | ○ | ○ | ○ | 31 | 55 |
| #12-3 | Ub7KR(G76A) | ○ | p53-p18 | ○ | ○ | 32 | 56 |
| #12-4 | Ub7KR(G76A) | X | p53-p18 | ○ | ○ | 33 | 57 |
| #12-9 | Ub7KR(G76A) | ○ | pDIQ-p18 | ○ | ○ | 34 | 62 |
| #12-10 | Ub7KR(G76A) | ○ | pDIQ | ○ | ○ | 35 | 63 |
| #12-11 | Ub7KR(G76A) | ○ | pMI-p18 | ○ | ○ | 36 | 64 |
| #12-12 | Ub7KR(G76A) | ○ | pMI | ○ | ○ | 37 | 65 |
| #12-13 | Ub7KR(G76A) | ○ | p53m-p18 | ○ | ○ | 38 | 66 |
| #12-14 | Ub7KR(G76A) | ○ | p53m | ○ | ○ | 39 | 67 |

TABLE 3

| | Protein complex | | | | | | Amino |
|---|---|---|---|---|---|---|---|
| No. | Ub | Biologically active molecule | AAT | MTS | NLS | DNA (SEQ ID) | Acid (SEQ ID) |
| #12-21 | Ub7KR(G76A) | X | ○ | ○ | ○ | 40 | 68 |
| #12-22 | Ub7KR(G76A) | X | ○ | X | ○ | 41 | 69 |
| #12-23 | Ub7KR(G76A) | p53 | ○ | ○ | ○ | 42 | 70 |
| #12-24 | Ub7KR(G76A) | p53 | ○ | X | ○ | 43 | 71 |
| #12-25 | Ub7KR(G76A) | p18 | ○ | ○ | ○ | 44 | 72 |
| #12-26 | Ub7KR(G76A) | p18 | ○ | X | ○ | 45 | 73 |
| #12-27 | Ub7KR(G76A) | p53-p18 | ○ | ○ | ○ | 46 | 74 |
| #12-28 | Ub7KR(G76A) | p53-p18 | ○ | X | ○ | 47 | 75 |
| #12-29 | Ub7KR(G76A) | pDIQ-p18 | ○ | ○ | ○ | 48 | 76 |
| #12-30 | Ub7KR(G76A) | pDIQ | ○ | ○ | ○ | 49 | 77 |
| #12-31 | Ub7KR(G76A) | pMI-p18 | ○ | ○ | ○ | 50 | 78 |
| #12-32 | Ub7KR(G76A) | pMI | ○ | ○ | ○ | 51 | 79 |
| #12-33 | Ub7KR(G76A) | p53m-p18 | ○ | ○ | ○ | 52 | 80 |
| #12-34 | Ub7KR(G76A) | p53m | ○ | ○ | ○ | 53 | 81 |

"○" indicates the presence of a moiety, and "X" indicates that no moiety was used.

herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A protein comprising an in vitro stabilization protein, a membrane translocation sequence domain, a biologically active molecule, and an in vivo stabilization protein, wherein the protein comprises the amino acid sequence of SEQ ID NO: 56, 58, 62, 63, 64, 65, 66, 67, 70, 72, 74, 76-82, 84, or 88.

2. A composition comprising the protein of claim 1 and a pharmaceutically acceptable carrier.

3. A method of delivering a biologically active molecule to a cell, the method comprising administering the protein of claim 1 to the cell.

4. The method of claim 3, wherein the protein is administered to the cell by contacting the cell with the protein.

5. The method of claim 3, wherein the cell is in vitro.

6. The method of claim 4, wherein the cell is in vivo in a subject, and the protein is administered to the cell by administering the protein to the subject.

7. A method of producing the protein of claim 1 comprising administering a nucleic acid encoding the protein to a cell, wherein the cell expresses the protein.

* * * * *